(12) United States Patent
Weiss

(10) Patent No.: US 10,995,129 B2
(45) Date of Patent: *May 4, 2021

(54) NON-STANDARD INSULIN ANALOGUES

(71) Applicant: Case Western Reserve University, Cleveland, OH (US)

(72) Inventor: Michael A. Weiss, Indianapolis, IN (US)

(73) Assignee: Case Western Reserve University, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/523,266

(22) Filed: Jul. 26, 2019

(65) Prior Publication Data

US 2019/0382463 A1 Dec. 19, 2019

Related U.S. Application Data

(63) Continuation-in-part of application No. 16/198,815, filed on Nov. 22, 2018, now Pat. No. 10,745,458, which is a continuation of application No. 15/277,319, filed on Sep. 27, 2016, now Pat. No. 10,138,284, which is a continuation of application No. 14/232,496, filed as application No. PCT/US2012/046575 on Jul. 13, 2012, now Pat. No. 9,487,572, application No. 16/523,266, which is a continuation-in-part of application No. 14/774,109, filed as application No. PCT/US2014/030387 on Mar. 17, 2014, now abandoned.

(60) Provisional application No. 61/798,165, filed on Mar. 15, 2013, provisional application No. 61/507,324, filed on Jul. 13, 2011.

(51) Int. Cl.
*C07K 14/62* (2006.01)
*A61K 38/28* (2006.01)
*A61P 3/08* (2006.01)
*C07K 14/65* (2006.01)

(52) U.S. Cl.
CPC .............. *C07K 14/65* (2013.01); *A61K 38/28* (2013.01); *A61P 3/08* (2018.01)

(58) Field of Classification Search
CPC ............ C07K 14/62; A61P 3/08; A61K 38/28
See application file for complete search history.

(56) References Cited

U.S. PATENT DOCUMENTS 6,221,633 B1* 4/2001 Ertl ..................... C07K 14/62
435/69.4
2011/0195896 A1* 8/2011 Weiss .................... A61K 38/28
514/5.9

FOREIGN PATENT DOCUMENTS

WO WO-2010014946 A2 * 2/2010 ............. C07K 14/62

* cited by examiner

*Primary Examiner* — James H Alstrum-Acevedo
*Assistant Examiner* — Erinne R Dabkowski
(74) *Attorney, Agent, or Firm* — Hahn Loeser & Parks, LLP; John J. Cunniff

(57) ABSTRACT

An insulin analogue comprises an insulin A-chain polypeptide and an insulin B-chain polypeptide. The A-chain polypeptide contains a Glu substitution at a position corresponding to position A8, and an Ala, Glu, Gln, His, Tyr, Phe or Trp substitution at a position A13, relative to wild type insulin. The B-chain polypeptide contains a cyclohexanylalanine substitution at position B24, relative to wild type insulin. The analogue may be an analogue of a mammalian insulin, such as human insulin. A nucleic acid encoding such an insulin analogue is also provided. A method of lowering the blood sugar of a patient comprises administering a physiologically effective amount of the insulin analogue or a physiologically acceptable salt thereof to a patient.

12 Claims, 23 Drawing Sheets

Specification includes a Sequence Listing.

Fig. 4A 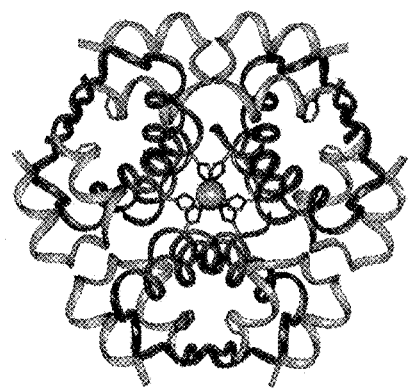 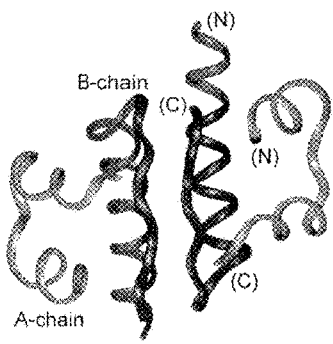 Fig. 4B
Fig. 4C 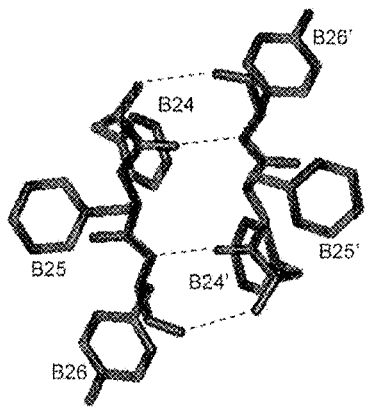 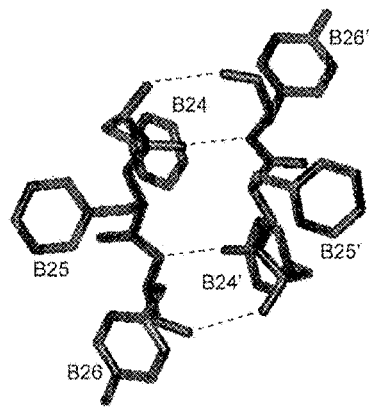
Fig. 4D 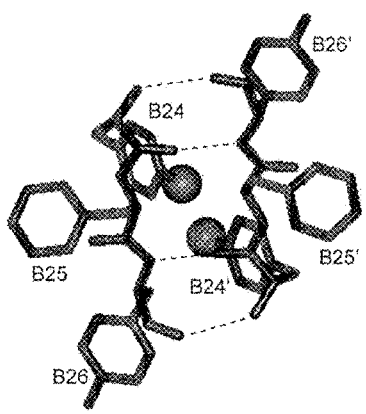 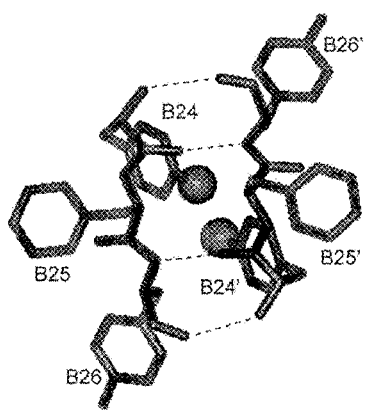

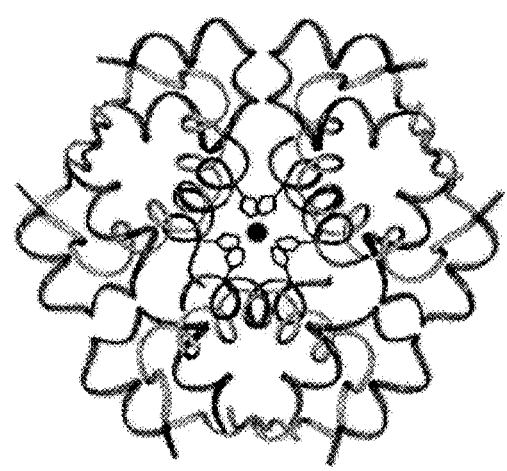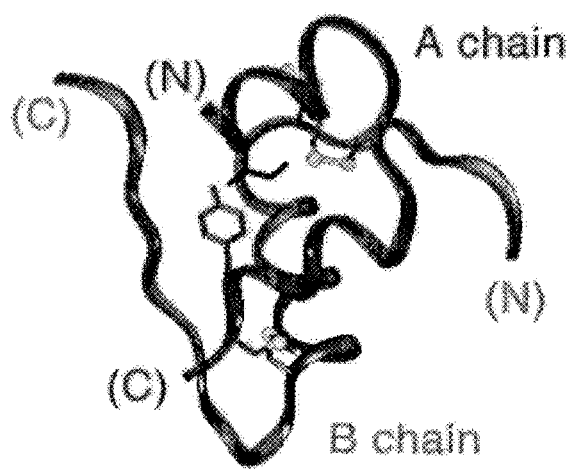
Fig. 5A                     Fig. 5B

SEQUENCE LISTING

<160> NUMBER OF SEQ ID NOS: 51

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (10)..(10)
<223> OTHER INFORMATION: Xaa is His or Asp
<220> FEATURE:
<221> NAME/KEY: MISC_FEATURE
<222> LOCATION: (24)..(24)
<223> OTHER INFORMATION: Xaa is Cyclohexanylalanine
<220> FEATURE:
<221> NAME/KEY: MISC_FEATURE
<222> LOCATION: (28)..(28)
<223> OTHER INFORMATION: Xaa is Asp, Pro, Lys, or Arg
<220> FEATURE:
<221> NAME/KEY: MISC_FEATURE
<222> LOCATION: (29)..(29)
<223> OTHER INFORMATION: Xaa is Lys, Pro, or Ala

<400> SEQUENCE: 4

Phe Val Asn Gln His Leu Cys Gly Ser Xaa Leu Val Glu Ala Leu Tyr
1               5                   10                  15

Leu Val Cys Gly Glu Arg Gly Xaa Phe Tyr Thr Xaa Xaa Thr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (10)..(10)
<223> OTHER INFORMATION: Xaa is His or Asp
<220> FEATURE:
<221> NAME/KEY: MISC_FEATURE
<222> LOCATION: (24)..(24)
<223> OTHER INFORMATION: Xaa is Cyclohexanylalanine
<220> FEATURE:
<221> NAME/KEY: MISC_FEATURE
<222> LOCATION: (29)..(29)
<223> OTHER INFORMATION: Xaa is Asp, Pro, Ornithine, Diaminobutyric
      acid, Diaminoproprionic acid, Norleucine, Aminobutric acid, or
      Aminoproprionic acid

<400> SEQUENCE: 5

Phe Val Asn Gln His Leu Cys Gly Ser Xaa Leu Val Glu Ala Leu Tyr
1               5                   10                  15

Leu Val Cys Gly Glu Arg Gly Xaa Phe Tyr Thr Pro Xaa Thr
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Asp Lys Thr
            20                  25                  30

```
<210> SEQ ID NO 8
<211> LENGTH: 86
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (1)..(1)
<223> OTHER INFORMATION: Xaa is His or Phe
<220> FEATURE:
<221> NAME/KEY: MISC_FEATURE
<222> LOCATION: (24)..(24)
<223> OTHER INFORMATION: Xaa is Cha
<220> FEATURE:
<221> NAME/KEY: MISC_FEATURE
<222> LOCATION: (26)..(26)
<223> OTHER INFORMATION: Xaa is Tyr or Phe
<220> FEATURE:
<221> NAME/KEY: MISC_FEATURE
<222> LOCATION: (28)..(28)
<223> OTHER INFORMATION: Xaa is Pro, Lys, or Asp
<220> FEATURE:
<221> NAME/KEY: MISC_FEATURE
<222> LOCATION: (29)..(29)
<223> OTHER INFORMATION: Xaa is Lys or Pro
<220> FEATURE:
<221> NAME/KEY: MISC_FEATURE
<222> LOCATION: (31)..(65)
<223> OTHER INFORMATION: Xaa is 0-35 of any amino acid or a break in the
      amino acid chain
<220> FEATURE:
<221> NAME/KEY: MISC_FEATURE
<222> LOCATION: (69)..(69)
<223> OTHER INFORMATION: Xaa is His or Glu
<220> FEATURE:
<221> NAME/KEY: MISC_FEATURE
<222> LOCATION: (73)..(73)
<223> OTHER INFORMATION: Xaa is His or Thr

<400> SEQUENCE: 8

Xaa Val Asn Gln His Leu Cys Gly Ser His Leu Val Glu Ala Leu Tyr
1               5                   10                  15

Leu Val Cys Gly Glu Arg Gly Xaa Phe Xaa Thr Xaa Xaa Thr Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Gly Ile Val Xaa Gln Cys Cys Xaa Ser Ile Cys Ser Leu Tyr Gln
65                  70                  75                  80

Leu Glu Asn Tyr Cys Asn
                85

<210> SEQ ID NO 9
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 9

Phe Val Lys Gln His Leu Cys Gly Ser His Leu Val Glu Ala Leu Tyr
1               5                   10                  15

Leu Val Cys Gly Glu Arg Gly Xaa Phe Tyr Thr Pro Glu Thr
```

```
                    20                  25                  30
```

<210> SEQ ID NO 10
<211> LENGTH: 22
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (10)..(10)
<223> OTHER INFORMATION: Xaa is His or Asp

<400> SEQUENCE: 10

```
Phe Val Asn Gln His Leu Cys Gly Ser Xaa Leu Val Glu Ala Leu Tyr
1               5                   10                  15

Leu Val Cys Gly Glu Arg
            20
```

<210> SEQ ID NO 11
<211> LENGTH: 8
<212> TYPE: PRT
<213> ORGANISM: Artificial Sequence
<220> FEATURE:
<223> OTHER INFORMATION: SYNTHETIC CONSTRUCT

<400> SEQUENCE: 11

```
Gly Phe Phe Tyr Thr Pro Lys Thr
1               5
```

<210> SEQ ID NO 12
<211> LENGTH: 8
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (2)..(2)
<223> OTHER INFORMATION: Xaa is Phe or Cyclohexanylalanine

<400> SEQUENCE: 12

```
Gly Xaa Phe Tyr Thr Lys Pro Thr
1               5
```

<210> SEQ ID NO 13
<211> LENGTH: 8
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (2)..(2)
<223> OTHER INFORMATION: Xaa is Phe or Cyclohexanylalanine
<220> FEATURE:
<221> NAME/KEY: MISC_FEATURE
<222> LOCATION: (7)..(7)
<223> OTHER INFORMATION: Xaa is Ornithine

<400> SEQUENCE: 13

```
Gly Xaa Phe Tyr Thr Pro Xaa Thr
1               5
```

<210> SEQ ID NO 14
<211> LENGTH: 8
<212> TYPE: PRT
<213> ORGANISM: Artificial Sequence
<220> FEATURE:

```
<223> OTHER INFORMATION: SYNTHETIC CONSTRUCT
<220> FEATURE:
<221> NAME/KEY: MISC_FEATURE
<222> LOCATION: (2)..(2)
<223> OTHER INFORMATION: Xaa is Phe or Cyclohexanylalanine
<220> FEATURE:
<221> NAME/KEY: MISC_FEATURE
<222> LOCATION: (7)..(7)
<223> OTHER INFORMATION: Xaa is Norleucine

<400> SEQUENCE: 14

Gly Xaa Phe Tyr Thr Pro Xaa Thr
 1               5

<210> SEQ ID NO 15
<211> LENGTH: 90
<212> TYPE: DNA
<213> ORGANISM: Artificial Sequence
<220> FEATURE:
<223> OTHER INFORMATION: SYNTHETIC CONSTRUCT

<400> SEQUENCE: 15
tttgtgaacc aacacctgtg cggctcacac ctggtggaag ctctctacct agtgtgcggg    60
gaacgaggct agttctacac acccaagacc                                    90

<210> SEQ ID NO 16
<211> LENGTH: 90
<212> TYPE: DNA
<213> ORGANISM: Artificial Sequence
<220> FEATURE:
<223> OTHER INFORMATION: SYNTHETIC CONSTRUCT

<400> SEQUENCE: 16
tttgttaacc aacatttgtg tggttctcat ttggttgaag ctttgtactt ggtttgtggt    60
gaaagaggtt agttttacac tccaaagact                                    90

<210> SEQ ID NO 17
<211> LENGTH: 261
<212> TYPE: DNA
<213> ORGANISM: Artificial Sequence
<220> FEATURE:
<223> OTHER INFORMATION: SYNTHETIC CONSTRUCT

<400> SEQUENCE: 17
tttgtgaacc aacacctgtg cggctcacac ctggtggaag ctctctacct agtgtgcggg    60
gaacgaggct agttctacac acccaagacc cgccgggagg cagaggacct gcaggtgggg   120
caggtggagc tgggcggcgg ccctggtgca ggcagcctgc agcccttggc cctggagggg   180
tccctgcaga agcgtggcat tgtggaacaa tgctgtacca gcatctgctc cctctaccag   240
ctggagaact actgcaacta g                                            261

<210> SEQ ID NO 18
<211> LENGTH: 261
<212> TYPE: DNA
<213> ORGANISM: Artificial Sequence
<220> FEATURE:
<223> OTHER INFORMATION: SYNTHETIC CONSTRUCT

<400> SEQUENCE: 18
tttgttaacc aacatttgtg tggttctcat ttggttgaag ctttgtactt ggtttgtggt    60
gaaagaggtt agttttacac tccaaagact agaagagaag ctgaagattt gcaagttggt   120
caagttgaat tgggtggtgg tccaggtgct ggttctttgc aaccattggc tttggaaggt   180
```

```
tctttgcaaa agagaggtat tgttgaacaa tgttgtactt ctatttgttc tttgtaccaa      240
ttggaaaact actgtaacta a                                                261
```

<210> SEQ ID NO 19
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 19

Gly Ile Val Glu Gln Cys Cys Glu Ser Ile Cys Ser Leu Tyr Gln Leu
1               5                   10                  15

Glu Asn Tyr Cys Asn
            20

<210> SEQ ID NO 20
<211> LENGTH: 30
<212> TYPE: PRT
<213> ORGANISM: Artificial Sequence
<220> FEATURE:
<223> OTHER INFORMATION: SYNTHETIC CONSTRUCT

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is Cyclohexanylalanine

<400> SEQUENCE: 21

Phe Val Asn Gln His Leu Cys Gly Ser Asp Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (25)..(25)
<223> OTHER INFORMATION: Xaa is Cyclohexanylalanine

<400> SEQUENCE: 22

Phe Val Asn Gln His Leu Cys Gly Ser Asp Leu Val Glu Ala Leu Tyr
1               5                   10                  15

Leu Val Cys Gly Glu Arg Gly Phe Xaa Tyr Thr Lys Pro Thr
            20                  25                  30

<210> SEQ ID NO 23
<211> LENGTH: 8

```
<212> TYPE: PRT
<213> ORGANISM: Artificial Sequence
<220> FEATURE:
<223> OTHER INFORMATION: SYNTHETIC CONSTRUCT

<400> SEQUENCE: 23

Asp Tyr Lys Asp Asp Asp Asp Lys
1               5

<210> SEQ ID NO 24
<211> LENGTH: 21
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (12)..(12)
<223> OTHER INFORMATION: Xaa is Ala, Thr, Asp, Asn, Glu, Gln, His or Tyr

<400> SEQUENCE: 24

Gly Ile Val Glu Gln Cys Cys Thr Ser Ile Cys Xaa Leu Tyr Gln Leu
1               5                   10                  15

Glu Asn Tyr Cys Asn
            20

<210> SEQ ID NO 25
<211> LENGTH: 21
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (13)..(13)
<223> OTHER INFORMATION: Xaa is Ala, Glu, Gln, His, Tyr or Trp

<400> SEQUENCE: 25

Gly Ile Val Glu Gln Cys Cys Thr Ser Ile Cys Ser Xaa Tyr Gln Leu
1               5                   10                  15

Glu Asn Tyr Cys Asn
            20

<210> SEQ ID NO 26
<211> LENGTH: 21
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (17)..(17)
<223> OTHER INFORMATION: Xaa is Ala, Gln, His, Trp, or Tyr.

<400> SEQUENCE: 26

Gly Ile Val Glu Gln Cys Cys Thr Ser Ile Cys Ser Leu Tyr Gln Leu
1               5                   10                  15

Xaa Asn Tyr Cys Asn
            20

<210> SEQ ID NO 27
<211> LENGTH: 21
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
```

```
<222> LOCATION: (12)..(12)
<223> OTHER INFORMATION: Xaa is Ser, Ala, Thr, Asp, Asn, Glu, Gln, His
      or Tyr
<220> FEATURE:
<221> NAME/KEY: MISC_FEATURE
<222> LOCATION: (13)..(13)
<223> OTHER INFORMATION: Xaa is Leu, Ala, Glu, Gln, His, or Trp
<220> FEATURE:
<221> NAME/KEY: MISC_FEATURE
<222> LOCATION: (17)..(17)
<223> OTHER INFORMATION: Xaa is Glu, Ala, Gln, His, Trp, or Tyr

<400> SEQUENCE: 27

Gly Ile Val Glu Gln Cys Cys Thr Ser Ile Cys Xaa Xaa Tyr Gln Leu
1               5                   10                  15

Xaa Asn Tyr Cys Asn
            20

<210> SEQ ID NO 28
<211> LENGTH: 21
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa is His, Glu, Gln, Arg, or Lys
<220> FEATURE:
<221> NAME/KEY: MISC_FEATURE
<222> LOCATION: (12)..(12)
<223> OTHER INFORMATION: Xaa is Ser, Ala, Thr, Asp, Asn, Glu, Gln, His
      or Tyr
<220> FEATURE:
<221> NAME/KEY: MISC_FEATURE
<222> LOCATION: (13)..(13)
<223> OTHER INFORMATION: Xaa is Leu, Ala, Glu, Gln, His, or Trp
<220> FEATURE:
<221> NAME/KEY: MISC_FEATURE
<222> LOCATION: (17)..(17)
<223> OTHER INFORMATION: Xaa is Glu, Ala, Gln, His, Trp, or Tyr

<400> SEQUENCE: 28

Gly Ile Val Glu Gln Cys Cys Xaa Ser Ile Cys Xaa Xaa Tyr Gln Leu
1               5                   10                  15

Xaa Asn Tyr Cys Asn
            20

<210> SEQ ID NO 29
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (13)..(13)
<223> OTHER INFORMATION: Xaa is Ala, Asp, His, or Leu
<220> FEATURE:
<221> NAME/KEY: MISC_FEATURE
<222> LOCATION: (28)..(28)
<223> OTHER INFORMATION: Xaa is any amino acid excluding Glycine,
      Tryptophan, Phenylalanine, Tyrosine, and Cysteine
<220> FEATURE:
<221> NAME/KEY: MISC_FEATURE
<222> LOCATION: (29)..(29)
<223> OTHER INFORMATION: Xaa is Pro, Glu or Lys

<400> SEQUENCE: 29

Phe Val Asn Gln His Leu Cys Gly Ser His Leu Val Xaa Ala Leu Tyr
1               5                   10                  15
```

Leu Val Cys Gly Glu Arg Gly Phe Phe Tyr Thr Xaa Xaa Thr
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (17)..(17)
<223> OTHER INFORMATION: Xaa is Glu, Gln, Ala, His, Trp, or Tyr
<220> FEATURE:
<221> NAME/KEY: MISC_FEATURE
<222> LOCATION: (28)..(28)
<223> OTHER INFORMATION: Xaa is any amino acid excluding Glycine,
      Tryptophan, Phenylalanine, Tyrosine, and Cysteine
<220> FEATURE:
<221> NAME/KEY: MISC_FEATURE
<222> LOCATION: (29)..(29)
<223> OTHER INFORMATION: Xaa is Pro, Glu, or Lys

<400> SEQUENCE: 30

Phe Val Asn Gln His Leu Cys Gly Ser His Leu Val Glu Ala Leu Tyr
1               5                   10                  15

Xaa Val Cys Gly Glu Arg Gly Phe Phe Tyr Thr Xaa Xaa Thr
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (13)..(13)
<223> OTHER INFORMATION: Xaa is Ala, Asp, His, or Leu
<220> FEATURE:
<221> NAME/KEY: MISC_FEATURE
<222> LOCATION: (17)..(17)
<223> OTHER INFORMATION: Xaa is Gln, Glu, Ala, His, Trp, or Tyr
<220> FEATURE:
<221> NAME/KEY: MISC_FEATURE
<222> LOCATION: (28)..(28)
<223> OTHER INFORMATION: Xaa is any amino acid excluding Glycine,
      Tryptophan, Phenylalanine, Tyrosine, and Cysteine
<220> FEATURE:
<221> NAME/KEY: MISC_FEATURE
<222> LOCATION: (29)..(29)
<223> OTHER INFORMATION: Xaa is Pro, Glu, or Lys

<400> SEQUENCE: 31

Phe Val Asn Gln His Leu Cys Gly Ser His Leu Val Xaa Ala Leu Tyr
1               5                   10                  15

Xaa Val Cys Gly Glu Arg Gly Phe Phe Tyr Thr Xaa Xaa Thr
            20                  25                  30

<210> SEQ ID NO 32
<211> LENGTH: 62
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (10)..(10)
<223> OTHER INFORMATION: Xaa is His or Asp
<220> FEATURE:
<221> NAME/KEY: MISC_FEATURE
<222> LOCATION: (13)..(13)

```
<223> OTHER INFORMATION: Xaa is Glu, Ala, Asp, His, or Leu
<220> FEATURE:
<221> NAME/KEY: MISC_FEATURE
<222> LOCATION: (17)..(17)
<223> OTHER INFORMATION: Xaa is Leu, Glu, Gln, Ala, His, Trp, or Tyr
<220> FEATURE:
<221> NAME/KEY: MISC_FEATURE
<222> LOCATION: (28)..(28)
<223> OTHER INFORMATION: Xaa is any amino acid excluding Glycine,
      Tryptophan, Phenylalanine, Tyrosine, and Cysteine
<220> FEATURE:
<221> NAME/KEY: MISC_FEATURE
<222> LOCATION: (29)..(29)
<223> OTHER INFORMATION: Xaa is Pro or Lys
<220> FEATURE:
<221> NAME/KEY: MISC_FEATURE
<222> LOCATION: (32)..(39)
<223> OTHER INFORMATION: Xaa is 3-8 of any amino acids
<220> FEATURE:
<221> NAME/KEY: MISC_FEATURE
<222> LOCATION: (49)..(49)
<223> OTHER INFORMATION: Xaa is Glu, Gln, His, Arg, Lys or Ornithine
<220> FEATURE:
<221> NAME/KEY: MISC_FEATURE
<222> LOCATION: (53)..(53)
<223> OTHER INFORMATION: Xaa is Ser, Ala, Thr, Asp, Asn, Glu, Gln, Tyr
      or His
<220> FEATURE:
<221> NAME/KEY: MISC_FEATURE
<222> LOCATION: (54)..(54)
<223> OTHER INFORMATION: Xaa is Leu, Ala, Glu, Gln, His, Tyr or Trp
<220> FEATURE:
<221> NAME/KEY: MISC_FEATURE
<222> LOCATION: (55)..(55)
<223> OTHER INFORMATION: Xaa is Tyr or Glu
<220> FEATURE:
<221> NAME/KEY: MISC_FEATURE
<222> LOCATION: (58)..(58)
<223> OTHER INFORMATION: Xaa is Glu, Gln, Ala, His, Trp, Tyr or Leu

<400> SEQUENCE: 32

Phe Val Asn Gln His Leu Cys Gly Ser Xaa Leu Val Xaa Ala Leu Tyr
1               5                   10                  15

Xaa Val Cys Gly Glu Arg Gly Phe Phe Tyr Thr Xaa Xaa Thr Gly Xaa
            20                  25                  30

Xaa Xaa Xaa Xaa Xaa Xaa Xaa Arg Arg Gly Ile Val Glu Gln Cys Cys
        35                  40                  45

Xaa Ser Ile Cys Xaa Xaa Xaa Gln Leu Xaa Asn Tyr Cys Asn
    50                  55                  60

<210> SEQ ID NO 33
<211> LENGTH: 62
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (10)..(10)
<223> OTHER INFORMATION: Xaa is His or Asp
<220> FEATURE:
<221> NAME/KEY: MISC_FEATURE
<222> LOCATION: (13)..(13)
<223> OTHER INFORMATION: Xaa is Glu, Ala, Asp, His or Leu
<220> FEATURE:
<221> NAME/KEY: MISC_FEATURE
<222> LOCATION: (17)..(17)
<223> OTHER INFORMATION: Xaa is Leu, Glu, Gln, Ala, His, Trp or Tyr
<220> FEATURE:
<221> NAME/KEY: MISC_FEATURE
<222> LOCATION: (28)..(28)
<223> OTHER INFORMATION: Xaa is any amino acid excluding Glycine,
      Tryptophan, Phenylalanine, Tyrosine, and Cysteine
<220> FEATURE:
```

```
<221> NAME/KEY: MISC_FEATURE
<222> LOCATION: (29)..(29)
<223> OTHER INFORMATION: Xaa is Pro or Lys
<220> FEATURE:
<221> NAME/KEY: MISC_FEATURE
<222> LOCATION: (32)..(39)
<223> OTHER INFORMATION: Xaa is 2-7 of any amino acids
<220> FEATURE:
<221> NAME/KEY: MISC_FEATURE
<222> LOCATION: (49)..(49)
<223> OTHER INFORMATION: Xaa is Glu, Gln, His, Arg, Lys or Ornithine
<220> FEATURE:
<221> NAME/KEY: MISC_FEATURE
<222> LOCATION: (53)..(53)
<223> OTHER INFORMATION: Xaa is Ser, Ala, Thr, Asp, Asn, Glu, Gln, Tyr
    or His
<220> FEATURE:
<221> NAME/KEY: MISC_FEATURE
<222> LOCATION: (54)..(54)
<223> OTHER INFORMATION: Xaa is Leu, Ala, Glu, Gln, His, Tyr or Trp
<220> FEATURE:
<221> NAME/KEY: MISC_FEATURE
<222> LOCATION: (55)..(55)
<223> OTHER INFORMATION: Xaa is Tyr or Glu
<220> FEATURE:
<221> NAME/KEY: MISC_FEATURE
<222> LOCATION: (58)..(58)
<223> OTHER INFORMATION: Xaa is Glu, Gln, Ala, His, Trp, Tyr or Leu

<400> SEQUENCE: 33

Phe Val Asn Gln His Leu Cys Gly Ser Xaa Leu Val Xaa Ala Leu Tyr
1               5                   10                  15

Xaa Val Cys Gly Glu Arg Gly Phe Phe Tyr Thr Xaa Xaa Thr Glu Glu
                20                  25                  30

Xaa Xaa Xaa Xaa Xaa Xaa Xaa Arg Arg Gly Ile Val Glu Gln Cys Cys
            35                  40                  45

Xaa Ser Ile Cys Xaa Xaa Xaa Gln Leu Xaa Asn Tyr Cys Asn
        50                  55                  60

<210> SEQ ID NO 34
<211> LENGTH: 62
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (10)..(10)
<223> OTHER INFORMATION: Xaa is His or Asp
<220> FEATURE:
<221> NAME/KEY: MISC_FEATURE
<222> LOCATION: (13)..(13)
<223> OTHER INFORMATION: Xaa is Glu, Ala, Asp, His, or Leu
<220> FEATURE:
<221> NAME/KEY: MISC_FEATURE
<222> LOCATION: (17)..(17)
<223> OTHER INFORMATION: Xaa is Leu, Glu, Gln, Ala, His, Trp or Tyr
<220> FEATURE:
<221> NAME/KEY: MISC_FEATURE
<222> LOCATION: (28)..(28)
<223> OTHER INFORMATION: Xaa is any amino acid excluding Glycine,
    Tryptophan, Phenylalanine, Tyrosine, and Cysteine
<220> FEATURE:
<221> NAME/KEY: MISC_FEATURE
<222> LOCATION: (29)..(29)
<223> OTHER INFORMATION: Xaa is Pro or Lys
<220> FEATURE:
<221> NAME/KEY: MISC_FEATURE
<222> LOCATION: (32)..(39)
<223> OTHER INFORMATION: Xaa is 3-8 of any amino acids
<220> FEATURE:
<221> NAME/KEY: MISC_FEATURE
<222> LOCATION: (49)..(49)
<223> OTHER INFORMATION: Xaa is Glu, Gln, His, Arg, Lys or Ornithine
```

```
<220> FEATURE:
<221> NAME/KEY: MISC_FEATURE
<222> LOCATION: (53)..(53)
<223> OTHER INFORMATION: Xaa is Ser, Ala, Thr, Asp, Asn, Glu, Gln, Tyr
      or His
<220> FEATURE:
<221> NAME/KEY: MISC_FEATURE
<222> LOCATION: (54)..(54)
<223> OTHER INFORMATION: Xaa is Leu, Ala, Glu, Gln, His, Tyr or Trp
<220> FEATURE:
<221> NAME/KEY: MISC_FEATURE
<222> LOCATION: (55)..(55)
<223> OTHER INFORMATION: Xaa is Tyr or Glu
<220> FEATURE:
<221> NAME/KEY: MISC_FEATURE
<222> LOCATION: (58)..(58)
<223> OTHER INFORMATION: Xaa is Glu, Gln, Ala, His, Trp, Tyr or Leu

<400> SEQUENCE: 34

Phe Val Asn Gln His Leu Cys Gly Ser Xaa Leu Val Xaa Ala Leu Tyr
1               5                   10                  15

Xaa Val Cys Gly Glu Arg Gly Phe Phe Tyr Thr Xaa Xaa Thr Glu Xaa
            20                  25                  30

Xaa Xaa Xaa Xaa Xaa Xaa Xaa Ser Arg Gly Ile Val Glu Gln Cys Cys
        35                  40                  45

Xaa Ser Ile Cys Xaa Xaa Xaa Gln Leu Xaa Asn Tyr Cys Asn
    50                  55                  60

<210> SEQ ID NO 35
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 35

Gly Ile Val Glu Gln Cys Cys Thr Ser Ile Cys Ser Glu Tyr Gln Leu
1               5                   10                  15

Glu Asn Tyr Cys Asn
            20

<210> SEQ ID NO 36
<211> LENGTH: 30
<212> TYPE: PRT
<213> ORGANISM: Artificial Sequence
<220> FEATURE:
<223> OTHER INFORMATION: SYNTHETIC CONSTRUCT

<400> SEQUENCE: 36

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is para-chloro-phenylalanine

<400> SEQUENCE: 37

Phe Val Asn Gln His Leu Cys Gly Ser His Leu Val Glu Ala Leu Tyr
```

```
                1               5                  10                  15
Leu Val Cys Gly Glu Arg Gly Xaa Phe Tyr Thr Lys Pro Thr
            20                  25                  30

<210> SEQ ID NO 38
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 38

Gly Ile Val Glu Gln Cys Cys Thr Ser Ile Cys Ser His Tyr Gln Leu
1               5                   10                  15

Glu Asn Tyr Cys Asn
            20

<210> SEQ ID NO 39
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 39

Gly Ile Val Glu Gln Cys Cys Thr Ser Ile Cys Ser Trp Tyr Gln Leu
1               5                   10                  15

Glu Asn Tyr Cys Asn
            20

<210> SEQ ID NO 40
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is ortho-fluoro-phenylalanine

<400> SEQUENCE: 40

Phe Val Asn Gln His Leu Cys Gly Ser Asp Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 41
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 41

Gly Ile Val Glu Gln Cys Cys Gln Ser Ile Cys Ser Trp Tyr Gln Leu
1               5                   10                  15

Glu Asn Tyr Cys Asn
            20

<210> SEQ ID NO 42
<211> LENGTH: 21
<212> TYPE: PRT
<213> ORGANISM: Artificial Sequence
<220> FEATURE:
```

<223> OTHER INFORMATION: SYNTHETIC CONSTRUCT

<400> SEQUENCE: 42

Gly Ile Val Glu Gln Cys Cys Thr Ser Ile Cys Ser Tyr Tyr Gln Leu
1               5                   10                  15

Glu Asn Tyr Cys Asn
            20

<210> SEQ ID NO 43
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is ortho-chloro-phenylalanine

<400> SEQUENCE: 43

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is cyclohexylalanine

<400> SEQUENCE: 44

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 45
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 45

Gly Ile Val Glu Gln Cys Cys Thr Ser Ile Cys Ser Ala Tyr Gln Leu
1               5                   10                  15

Glu Asn Tyr Cys Asn
            20

<210> SEQ ID NO 46
<211> LENGTH: 30
<212> TYPE: PRT
<213> ORGANISM: Artificial Sequence
<220> FEATURE:
<223> OTHER INFORMATION: SYNTHETIC CONSTRUCT

<400> SEQUENCE: 46

Phe Val Asn Gln His Leu Cys Gly Ser His Leu Val Glu Ala Leu Tyr
1               5                   10                  15

```
Glu Val Cys Gly Glu Arg Gly Phe Phe Tyr Thr Lys Pro Thr
            20                  25                  30
```

<210> SEQ ID NO 47
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 47

```
Gly Ile Val Glu Gln Cys Cys Thr Ser Ile Cys Ser Phe Tyr Gln Leu
1               5                   10                  15

Glu Asn Tyr Cys Asn
            20
```

<210> SEQ ID NO 48
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 48

```
Gly Ile Val Glu Gln Cys Cys Gln Ser Ile Cys Ser Trp Tyr Gln Leu
1               5                   10                  15

Glu Asn Tyr Cys Asn
            20
```

<210> SEQ ID NO 49
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (24)..(24)
<223> OTHER INFORMATION: Xaa is para-chloro-phenylalanine

<400> SEQUENCE: 49

```
Phe Val Asn Gln His Leu Cys Gly Ser His Leu Val Gln Ala Leu Tyr
1               5                   10                  15

Leu Val Cys Gly Glu Arg Gly Xaa Phe Tyr Thr Lys Pro Thr
            20                  25                  30
```

<210> SEQ ID NO 50
<211> LENGTH: 21
<212> TYPE: PRT
<213> ORGANISM: Artificial Sequence
<220> FEATURE:
<223> OTHER INFORMATION: SYNTHETIC CONSTRUCT

<400> SEQUENCE: 50

```
Gly Ile Val Glu Gln Cys Cys Glu Ser Ile Cys Ser Trp Tyr Gln Leu
1               5                   10                  15

Glu Asn Tyr Cys Asn
            20
```

<210> SEQ ID NO 51
<211> LENGTH: 30
<212> TYPE: PRT
<213> ORGANISM: Artificial Sequence
<220> FEATURE:
<223> OTHER INFORMATION: SYNTHETIC CONSTRUCT
<220> FEATURE:

```
<221> NAME/KEY: MISC_FEATURE
<222> LOCATION: (24)..(24)
<223> OTHER INFORMATION: Xaa1 is Cha

<400> SEQUENCE: 51

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Pro Lys Thr
            20                  25                  30
```

NON-STANDARD INSULIN ANALOGUES

CROSS REFERENCE TO RELATED APPLICATIONS

This application is a continuation-in-part application of co-pending U.S. application Ser. No. 16/198,815, filed Nov. 22, 2018, which is a continuation of U.S. application Ser. No. 15/277,319, filed Sep. 27, 2016 and issued as U.S. Pat. No. 10,138,284 on Nov. 27, 2018, which is a continuation of U.S. application Ser. No. 14/232,496, filed Jan. 13, 2014 and issued as U.S. Pat. No. 9,487,572 on Nov. 8, 2016, which is a national stage application of PCT/US2012/046575, filed Jul. 13, 2012, which claims the benefit of U.S. Provisional Application No. 61/507,324 filed on Jul. 13, 2011. This application is also a continuation-in-part of co-pending U.S. application Ser. No. 14/774,109 filed on Sep. 9, 2015, which is a national stage application of PCT/US14/30387, filed on Mar. 17, 2014, which claims benefit of U.S. Provisional Application No. 61/798,165, filed on Mar. 15, 2013. The disclosures of the above-referenced applications are incorporated herein by reference.

STATEMENT REGARDING FEDERALLY SPONSORED RESEARCH OR DEVELOPMENT

This invention was made with government support under grants DK040949 and DK074176 awarded by the National Institutes of Health (NIH). The government has certain rights in the invention.

BACKGROUND OF THE INVENTION

This invention relates to polypeptide hormone analogues that exhibits enhanced pharmaceutical properties, such as target-organ specificity. More particularly, this invention relates to insulin analogues that are modified by the incorporation of non-standard amino acids. Even more particularly, this invention relates to insulin analogues additionally containing one or more amino-acid substitutions in its "Site-2 receptor-binding surface." Such insulin analogues may optionally contain standard amino-acid substitutions at other sites in the A or B chains of an insulin analogue.

Administration of insulin has long been established as a treatment for diabetes mellitus. Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). Although the structure of proinsulin has not been determined, a variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). The sequence of insulin is shown in schematic form in FIG. 1C. Individual residues are indicated by the identity of the amino acid (typically using a standard three-letter code), the chain and sequence position (typically as a superscript).

Aromatic side chains in insulin, as in globular proteins in general, may engage in a variety of hydrophobic and weakly polar interactions, involving not only neighboring aromatic rings but also other sources of positive- or negative electrostatic potential. Examples include main-chain carbonyl- and amide groups in peptide bonds. Hydrophobic packing of aromatic side chains can occur within the core of proteins and at non-polar interfaces between proteins. Such aromatic side chains can be conserved among vertebrate proteins, reflecting their key contributions to structure or function. An example of a natural aromatic amino acid is phenylalanine. Its aromatic ring system contains six carbons arranged as a planar hexagon. Aromaticity is a collective property of the binding arrangement among these six carbons, leading to π electronic orbitals above and below the plane of the ring. These faces exhibit a partial negative electrostatic potential whereas the edge of the ring, containing five C—H moieties, exhibits a partial positive electrostatic potential. This asymmetric distribution of partial charges gives rise to a quadrapole electrostatic moment and may participate in weakly polar interactions with other formal or partial charges in a protein. An additional characteristic feature of an aromatic side chains is its volume. Determinants of this volume include the topographic contours of its five C—H moieties at the edges of the planar ring. Substitution of an aromatic ring system by a corresponding aliphatic ring system would increase side-chain volume with loss of planarity and gain of one additional hydrogen atom at each carbon site (e.g., substitution of each C—H element with trigonal hybridization by $CH_2$ with tetrahedral hybridization).

An example of a conserved aromatic residue in a therapeutic protein is provided by phenylalanine at position B24 of the B chain of insulin (designated $Phe^{B24}$). This is one of three phenylalanine residues in insulin (positions B1, B24, and B25). A structurally similar tyrosine is at position B26. The structural environment of $Phe^{B24}$ in an insulin monomer is shown in a ribbon model (FIG. 1D) and in a space-filling model (FIG. 1E). Conserved among vertebrate insulins and insulin-like growth factors, the aromatic ring of $Phe^{B24}$ packs against (but not within) the hydrophobic core to stabilize the super-secondary structure of the B-chain. $Phe^{B24}$ lies at the classical receptor-binding surface and has been proposed to direct a change in conformation on receptor binding.

It is known in the art that modifications or substitutions within the classical receptor-binding surface of insulin may impair the in vitro affinity of the hormone for its receptor by up to ca. fivefold (e.g., from a dissociation constant of 0.05 nM to a dissociation constant of 0.25 nM) without significant effect on in vivo potency as assessment by the ability of the variant insulin, when injected subcutaneously or intravenously, to cause a reduction in blood glucose concentration. Such robustness is, at least in part, attributed to a compensating relationship between affinity and rate of clearance of the hormone from the bloodstream. Because binding to the IR mediates both insulin action and, to a large extent, insulin clearance, a reduction in affinity leads to a proportionate increase in the circulatory half-life and hence opportunity to effect biological signaling. Examples of such compensation have been disclosed in relation to insulin analogues in which the Phenylalanine at position B24 is substituted by Cyclohexanylalanine (Cha), disclosed in U.S. Pat. Nos. 9,487,572 and 9,725,493 the disclosures of which are incorporated by reference herein. The non-planar aliphatic ring of Cha at position B24 (illustrated in FIG. 8) impairs receptor-binding affinity by ca. threefold but has no effect on the potency or pharmacodynamics properties of KP-insulin as tested in diabetic Sprague-Dawley rats (FIG. 3A). Additional examples have been provided by modified by fluoro-aromatic and chloro-aromatic substitutions at position B24 as illustrated in FIG. 4A and FIG. 4B; (in relation to the wild-type dimer interface) and as disclosed in U.S. Pat. Nos. 9,079,975; 8,921,313; 9,200,053; 9,079,975; and International Application No. PCT/US2012/62423, which are incorporated by reference herein. Modification of $Phe^{B24}$ in insulin Lispro ([$Lys^{B28}$, $Pro^{B29}$]-insulin, also designated KP-insulin (the active component of Humalog®); Eli Lilly and Co.) by a single chloro-substitution at the ortho position of the aromatic ring (2-Cl-$Phe^{B24)}$ thus impairs the biochemical affinity of the variant hormone for the isolated IR in vitro by ca. threefold without change in its in vivo potency as assessed in Sprague-Dawley rats rendered diabetic by streptozotocin or as assessed in anesthetized non-diabetic adolescent Yorkshire pigs in which endogenous insulin secretion was suppressed by intravenous octreotide (data not shown). Even more dramatically, whereas a derivative of [$Asp^{B10}$, $Lys^{B28}$, $Pro^{B29}$]-insulin (DKP-insulin) containing 2-F-$Phe^{B24}$ (ortho-monofluoro-phenylalalanine at position B24) exhibits a similar decrement in receptor-binding affinity (ca. 35(±5)% relative to KP-insulin), its potency and duration of signaling are enhanced in diabetic Sprague-Dawley rats (FIG. 9B) as disclosed in in U.S. Pat. No. 8,921,313 (which is incorporated by reference herein). It would be expected, therefore, that modifications or substitutions generally in the insulin molecule that introduce moderate perturbations to IR binding as evaluated in vitro would be well tolerated in vivo and be indistinguishable from wild-type insulin with respect to potency or (in the absence of effects on self-assembly) other pharmacological properties—or even more potent and prolonged as in the case of the 2-F-$Phe^{B24}$-DKP-insulin. It was therefore unexpected to discover that substitutions or modifications within Site 2 can markedly foreshorten the duration of insulin action in vivo (an alteration of pharmacodynamics) despite conferring perturbations to the biochemical affinity of the variant insulin for the IR of less than fivefold. Although side chains at positions B13, B17, A12, A13, and A17 are not thought to be engaged at the primary hormone-binding surface of the insulin receptor, alanine scanning mutagenesis has shown that single Alanine substitutions at Site-2-related positions affect relative receptor-binding affinities as follows: (position B13) 12(±3)%, (B17) 62(±14)%, (A12) 108(±28)%, (A13) 30(±7)%, and (A17) 56(±20)%.

The engineering of non-standard proteins, including therapeutic agents and vaccines, may have broad medical and societal benefits. Naturally occurring proteins—as encoded in the genomes of human beings, other mammals, vertebrate organisms, invertebrate organisms, or eukaryotic cells in general—often contain two or more functional surfaces. A benefit of protein analogues would be to achieve selective modification of one or the other of these functional surfaces, such as to provide fine-tuning of biological activity. An example of a therapeutic protein is provided by insulin. The three-dimensional structure of wild-type insulin has been well characterized as a zinc hexamer, as a zinc-free dimer, and as an isolated monomer in solution (FIGS. 5A, 5B and 6). Wild-type human insulin and insulin molecules encoded in the genomes of other mammals bind to insulin receptors (IRs), each of which containing multiple domains and associated domain surfaces. The IR is a dimer of αβ half-receptors (designated $(\alpha\beta)_2$) wherein the α chain and β chain are the post-translational products of a single precursor polypeptide. The hormone-binding surfaces of the $(\alpha\beta)_2$ dimer has been classified as Site 1 and Site 2 in relation to the non-linear binding and kinetic properties of the receptor. This binding scheme is shown in schematic form in FIG. 7. Recent advances in structural and biochemical analysis of fragments of the IR ectodomain have shown that Site 1 consists of a trans-binding element formed by both a subunits in the $(\alpha\beta)_2$ dimer: the N-terminal L1 domain of one subunit and the C-terminal α-helix (αCT) of the other (Whittaker J, Whittaker L J, Roberts C T Jr, Phillips N B, Ismail-Beigi F, Lawrence M C, and Weiss M A. α-Helical element at the hormone-binding surface of the insulin receptor functions as a signaling element to activate its tyrosine kinase. *Proc. Natl. Acad. Sci. USA* 109, 1116-71 (2012)). The location of Site 2 is not well characterized but is proposed to comprise parts of the first and second fibronectin-homology domains.

Presumptive Site 2-related residues may be defined either based on kinetic effects of mutations or based on positions that are extrinsic to site 1 wherein mutations nonetheless impair binding. These criteria highlight the potential importance of non-classical residues A12, A13, A17, B13 and B17. Respective Site-1-related and Site-2-related surfaces are shown in relation to the surface of an insulin monomer in FIG. 8. Whereas substitutions known in the art to accelerate the absorption of insulin from a subcutaneous depot are ordinarily within and adjacent to the Site-1-binding surface of the hormone (such as at residues B24, B28 or B29), we envisaged that modification of the Site-2-binding surface could modulate the cellular duration of signaling by the hormone-receptor complex once engaged at the surface of a target cell or tissue. Although not wishing to be restricted by theory, we further envisioned that such foreshortening of the cellular duration of signaling would confer "fast-off" pharmacokinetic properties to a rapid-acting insulin analogue ("fast-on") whose disassembly in the subcutaneous depot had been accelerated by substitutions within or adjacent to the Site-1-binding surface as known in the art (see FIG. 9 for rationale). Thus, such a novel combination of Site-1/Site-2-related substitutions would together confer the desirable combination of fast-on/fast-off pharmacokinetic properties of novel utility in the treatment of diabetes mellitus.

The present invention pertains to the use of a particular class of non-standard amino acids—an aliphatic ring system as exemplified by Cyclohexanylalanine (Cha)—to modify and improve distinct properties of insulin. During the past decade, specific chemical modifications to the insulin molecule have been described that selectively modify one or another particular property of the protein to facilitate an application of interest. Whereas at the beginning of the recombinant DNA era (1980) wild-type human insulin was envisaged as being optimal for use in diverse therapeutic contexts, the broad clinical use of insulin analogues in the past decade suggests that a suite of non-standard analogs, each tailored to address a specific unmet need, would provide significant medical and societal benefits. Substitution of one natural amino acid at a specific position in a protein by another natural amino acid is well known in the art and is herein designated a standard substitution. Non-standard substitutions in insulin offer the prospect of accelerated absorption without worsening of the resistance to degradation.

Protein engineering and the mechanism of insulin absorption. The major structural interface of the insulin hexamer is provided by an anti-parallel β-sheet at the dimerization surface. The component β-strands comprise residues B24-B28 and dimer-related residues B24'-B28'; this segment has the amino-acid sequence FFYTP. The core of the β-sheet is provided by the three aromatic side chains $Phe^{B24}$, $Phe^{B25}$, and $Tyr^{B26}$, which in the active insulin monomer also contact the insulin receptor. Substitutions known in the art to provide rapid-acting and active insulin analogues occur at positions B28 ($Pro^{B28}$ in wild-type insulin) and flanking site B29 ($Lys^{B29}$ in wild-type insulin). Standard amino-acid substitutions at core sites B24, B25, and B26 have not been employed in past design of insulin analogues intended for the treatment of patients with diabetes mellitus since such substitutions, as known in the art, typically impair biological activity. Substitution of $Phe^{B24}$ by Tyr, for example, impairs activity by more than twentyfold despite its seemingly conservative character. The importance of these invariant aromatic residues has been highlighted by the finding of genetic (germ-line) mutations at positions B24 and B25 that cause diabetes mellitus in human patients.

While not wishing to condition patentability on theory, it is believed that prolonged residence time for insulin in the insulin-insulin receptor complex is associated with enhanced risk of carcinogenesis. It is further believed that the mitogenic effect is more closely associated with the A-isoform of the insulin receptor (IR-A) than the B-isoform (IR-B). It is further believed that a change in relative affinity of an insulin analogue for IR-A and IR-B could affect target organ specificity.

There is a need, therefore for an insulin analogue that exhibits altered properties with respect to target-organ specificity. There is a further need for an insulin analogue with decreased hepatic insulin signaling, for example for patients with fatty liver syndrome.

SUMMARY OF THE INVENTION

It is, therefore, an aspect of the present invention to provide insulin analogues that provide altered properties with respect to target-organ specificity. There is a specific need for an insulin analogue with decreased hepatic insulin signaling that could be of clinical interest for patients with fatty liver syndrome. The claimed invention circumvents previous design restrictions, including those regarding substitution of $Phe^{B24}$, through the incorporation of a non-standard amino-acid substitution at position B24 together with a modification in the Site-2 bonding surface. The insulin analogue contains a non-standard amino-acid side chain and a substitution at a Site-2 related amino acid with a Glu A8 substitution. Site-2-related substitutions are modifications at one or more of the following positions: B13, B17, A12, A13, and A17. This is achieved by substitution of an aromatic amino-acid side chain at $Phe^{B24}$ by a non-aromatic analogue, Cyclohexanylalanine ($Cha^{B24}$), with a substitution at a Site-2 related residue and a Glu A8 substitution. Cyclohexanylalanine is non-planar but of approximately similar size and shape to Phenylalanine. The analogue then maintains at least a portion of biological activity of the corresponding insulin or insulin analogue containing the native aromatic side chain.

In general, the present invention provides an insulin analogue comprising an insulin B-chain polypeptide containing a cyclohexanylalanine substitution at position B24, a substitution at a site-2 related amino acid selected from substitutions at one or more of the following positions: B13, B17, A12, A13, and A17, and a Glu substitution at position A8. In one embodiment, the substitution at a Site-2 related residue is selected from the group consisting of substitutions at one or more of the following positions, relative to the corresponding position in wild-type insulin: B13, B17, A12, A13, and A17. In one embodiment, the Site-2 related substitution is located at position A13 relative to the corresponding position of wild-type insulin. In another embodiment, the Site-2 related substitution is Trp A13. In addition or in the alternative, the insulin analogue is a mammalian insulin analogue, such as an analogue of human insulin.

Also provided is a nucleic acid encoding an insulin analogue polypeptide that incorporates a non-standard amino acid at position B24, a substitution at a Site-2 related amino acid selected from substitutions at one or more of the following positions: B13, B17, A12, A13, and A17, and a Glu substitution at position A8. In one example, the non-standard amino acid is encoded by a stop codon, such as the nucleic acid sequence TAG. An expression vector may comprise such a nucleic acid and a host cell may contain such an expression vector.

The invention also provides a method of lowering the blood sugar a patient. The method comprises administering a physiologically effective amount of an insulin analogue or a physiologically acceptable salt thereof to the patient, wherein the insulin analogue or a physiologically acceptable salt thereof contains a B-chain polypeptide incorporating a Cyclohexanylalanine at B24, a substitution at a Site-2 related amino acid, and a Glu substitution at position A8. In one embodiment, the substitution at a Site-2 related residue is selected from the group consisting of substitutions at one or more of the following positions, relative to the corresponding position in wild-type insulin: B13, B17, A12, A13, and A17. In one embodiment, the Site-2 related substitution is located at position A13 relative to the corresponding position of wild-type insulin. In another embodiment, the Site-2 related substitution is Trp A13. In still another embodiment, the insulin analogue is a mammalian insulin analogue, such as an analogue of human insulin. In one particular set of embodiments, the B-chain polypeptide comprises an amino-acid sequence selected from the group consisting of SEQ. ID. NOS: 50 and 51 and polypeptides having three or fewer additional amino-acid substitutions thereof.

BRIEF DESCRIPTION OF THE SEVERAL VIEWS OF THE DRAWINGS

FIG. 4A is a ribbon model of wild-type $R_6$ zinc insulin hexamer. The A- and B chains are shown in light and dark gray, the axial zinc ions (overlaid) as spheres, and $Phe^{B24}$ side chains in medium gray.

FIG. 4B is a ribbon model of insulin dimer; the anti-parallel B24-B28 β-sheet is in middle. Coloring scheme as in FIG. 4A.

FIG. 4C is a stereo pair showing the aromatic cluster within the dimer interface of FIG. 4B; residues B24 and B24', B25 and B25', and B26 and B26'.

FIG. 4D is a predicted model of modified dimer interface; the para-chloro atoms at B24 (aromatic ring position 2) are shown as spheres (50% of van der Waals radii).

FIG. 5A is a representation of the structure of insulin as a phenol-stabilized $R_6$ zinc hexamer as in a typical pharmaceutical formulation. Axial zinc ions (overlaid) are shown as coincident black spheres coordinated by histidine side chains. The A-chain is shown in dark gray, and B-chain in medium gray (residues B1-B8) and light gray (B9-B30).

FIG. 5B is a representation of the structure of insulin as an isolated monomer in the bloodstream. The A chain is shown in dark gray, and B chain in medium gray; disulfide brides are depicted as balls and sticks.

FIG. 10A depicts wild-type insulin monomer (FIG. 3A). FIG. 10B depicts wild-type insulin dimer as extracted from the crystal structure of the $T_6$ zinc insulin hexamer (Protein Databank accession code 4INS). A corresponding model predicting the fit of Cyclohexanylalanine in the variant monomer is shown in FIG. 10C and the variant dimer in FIG. 10D.

DETAILED DESCRIPTION OF THE INVENTION

The present invention is directed an insulin analogue that provides altered properties with respect to target-organ specificity where the analogue maintains at least a portion of biological activity of the corresponding insulin or insulin analogue.

Figure 2A:
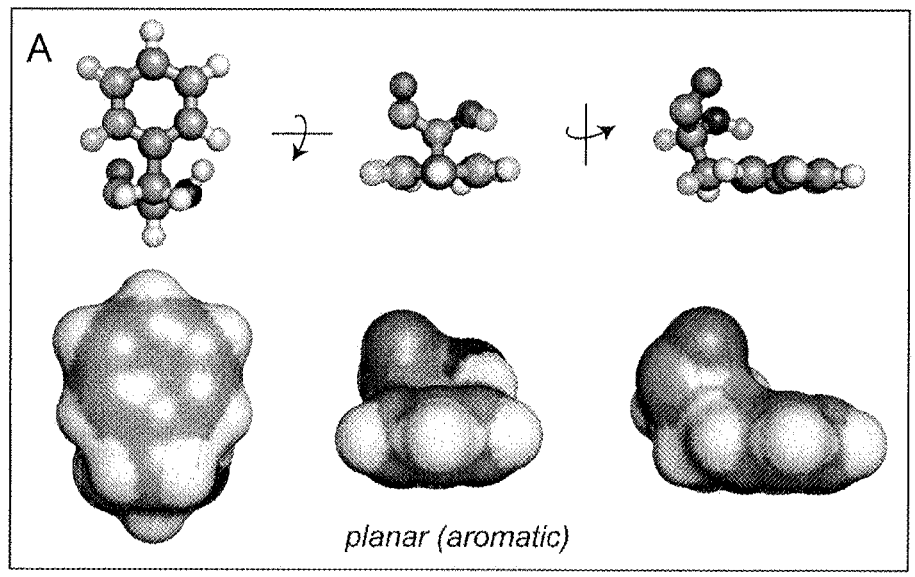
FIG. 2A is representation of Phenylalanine (Phe), in ball-and-stick models (top) and molecular surface models (bottom). Carbon and hydrogen atoms are medium and light gray, respectively, whereas oxygen (nitrogen) atoms are dark gray and nitrogen atoms are black.

The present invention pertains to non-standard modifications at position B24 and accompanying substitutions at positions A8 and A13 to differentially alter the insulin analogue's affinity for the A- and B-isoforms of the Insulin Receptor. In one embodiment, the ratio binding to the receptor is skewed toward the B-isoform of the insulin receptor (IR-B) and away from the more mitogenic A-isoform of the insulin receptor (IR-A). In one instance the non-standard amino acid lacks aromaticity and its associated asymmetric distribution of partial positive and negative charges as demonstrated by substitution of the non-planar aliphatic ring system of cyclohexanylalanine. Loss of planarity in a non-aromatic ring system is associated with a change in its topographical contours and an increase in side-chain volume (FIG. 2B) relative to phenylalanine (FIG. 2A).

In one embodiment, the present invention provides an insulin analogue that provides altered affinity to the A- and B-isoforms of the Insulin Receptor by substitution of phenylalanine at position B24, relative to wild-type insulin, by a non-standard amino acid. In one particular embodiment the substitution at position B24 is a cyclohexanylalanine substitution. The present invention is not limited, however, to human insulin and its analogues. It is also envisioned that these substitutions may also be made in animal insulins such as porcine, bovine, equine, and canine insulins, by way of non-limiting examples.

It has also been discovered that Cha$^{B24}$-KP-insulin, when formulated in Lilly Diluent and following subcutaneous injection in a male Lewis rat rendered diabetic by streptozotocin, will direct a reduction in blood glucose concentration with a potency similar to that of KP-insulin in the same formulation.

In addition or in the alternative, the insulin analogue of the present invention may contain a non-standard amino-acid substitution at position 29 of the B chain, which is lysine (Lys) in wild-type insulin. In one particular example, the non-standard amino acid at B29 is norleucine (Nle). In another particular example, the non-standard amino acid at B29 is ornithine (Orn).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids.

Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

In one example, the insulin analogue of the present invention contains three or fewer conservative substitutions other than the cyclic aliphatic substitution of the present invention.

As used in this specification and the claims, various amino acids in insulin or an insulin analogue may be noted by the amino-acid residue in question, followed by the position of the amino acid, optionally in superscript. The position of the amino acid in question includes the A- or B-chain of insulin where the substitution is located. Thus, Phe$^{B24}$ denotes a phenylalanine at the twenty-fourth amino acid of the B chain of insulin. Unless noted otherwise or wherever obvious from the context, the location of substitutions should be understood to be relative to and in the context of human insulin. Thus, the positions in insulin may be denoted without regard to any additional alterations that may be present such as a deletion at the amino terminal end. For example, in a B-chain polypeptide that included a deletion of the B1 amino acid, the first amino acid in the chain would still be denoted as "B2" as corresponding to the second amino acid of wild type insulin.

Figure 2B:
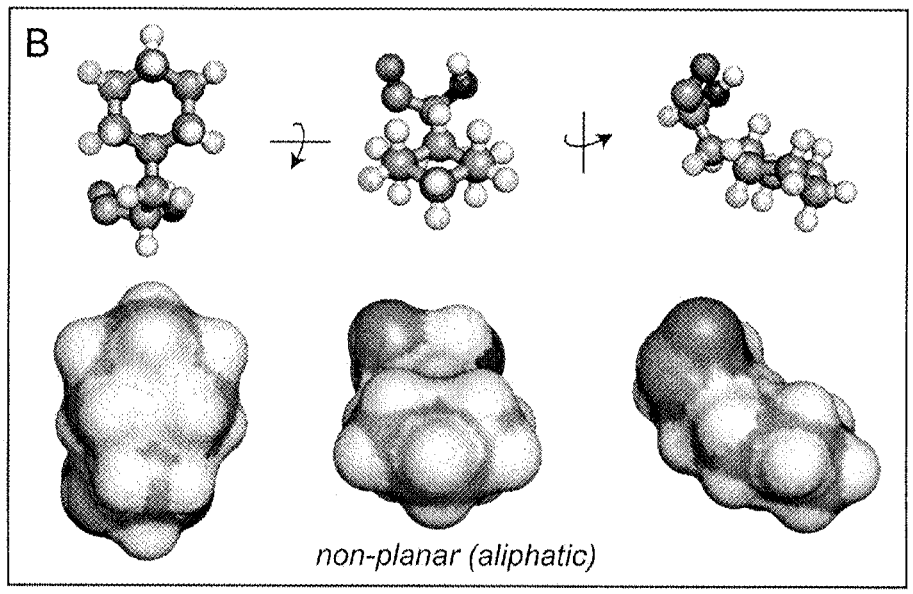
FIG. 2B is representation of Cyclohexanylalanine (Cha), in ball-and-stick models (top) and molecular surface models (bottom). Carbon and hydrogen atoms are medium and light gray, respectively, whereas oxygen (nitrogen) atoms are dark gray and nitrogen atoms are black.
Figure 3A:
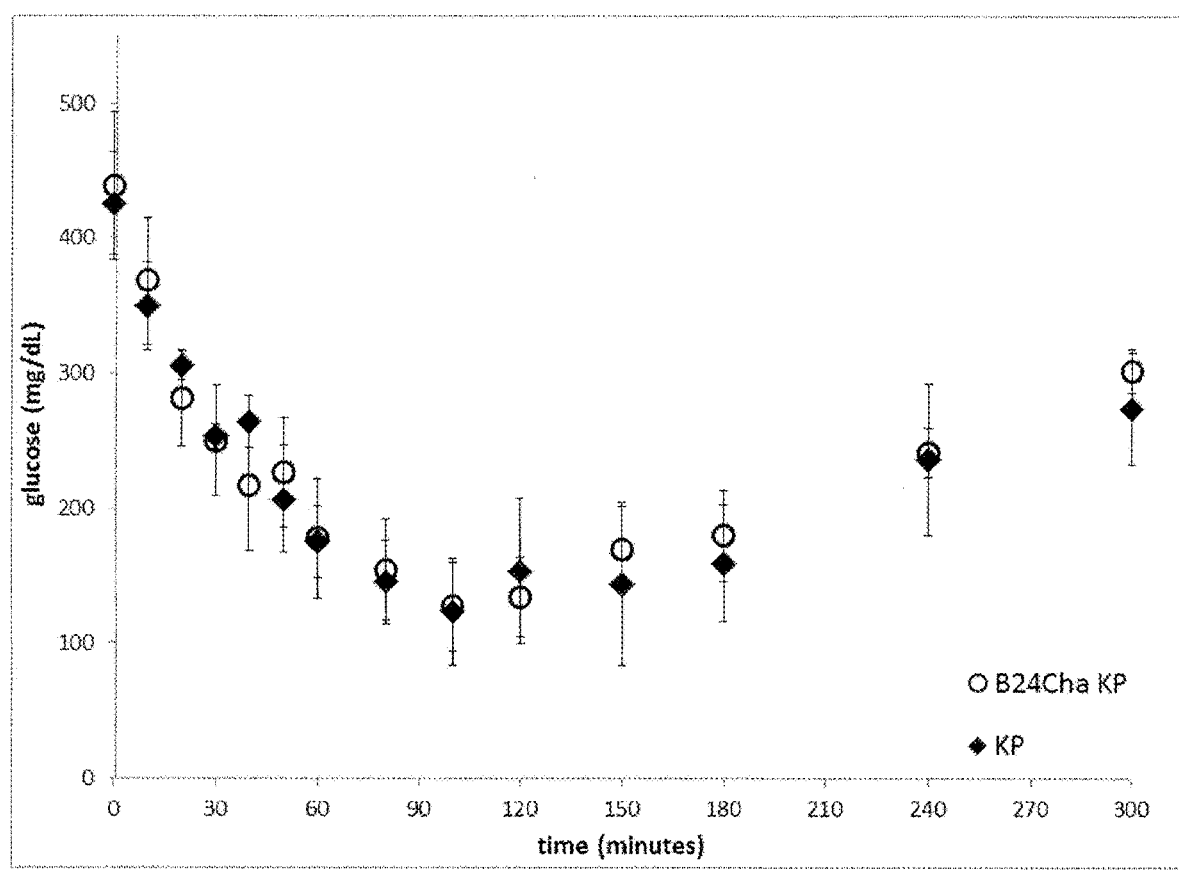
FIG. 3A is a graph showing the results of studies of glycemic response to subcutaneous injection of insulin Lispro (KP-insulin) (solid diamonds) and $Cha^{B24}$-DKP-insulin (B24Cha KP, open squares) in Sprague-Dawley rats rendered diabetic by streptozotocin, at a dose of 20 μg per rat. The relative affinity of $Cha^{B24}$-DKP-insulin is ca. 30(±5)%.
Figure 3B:
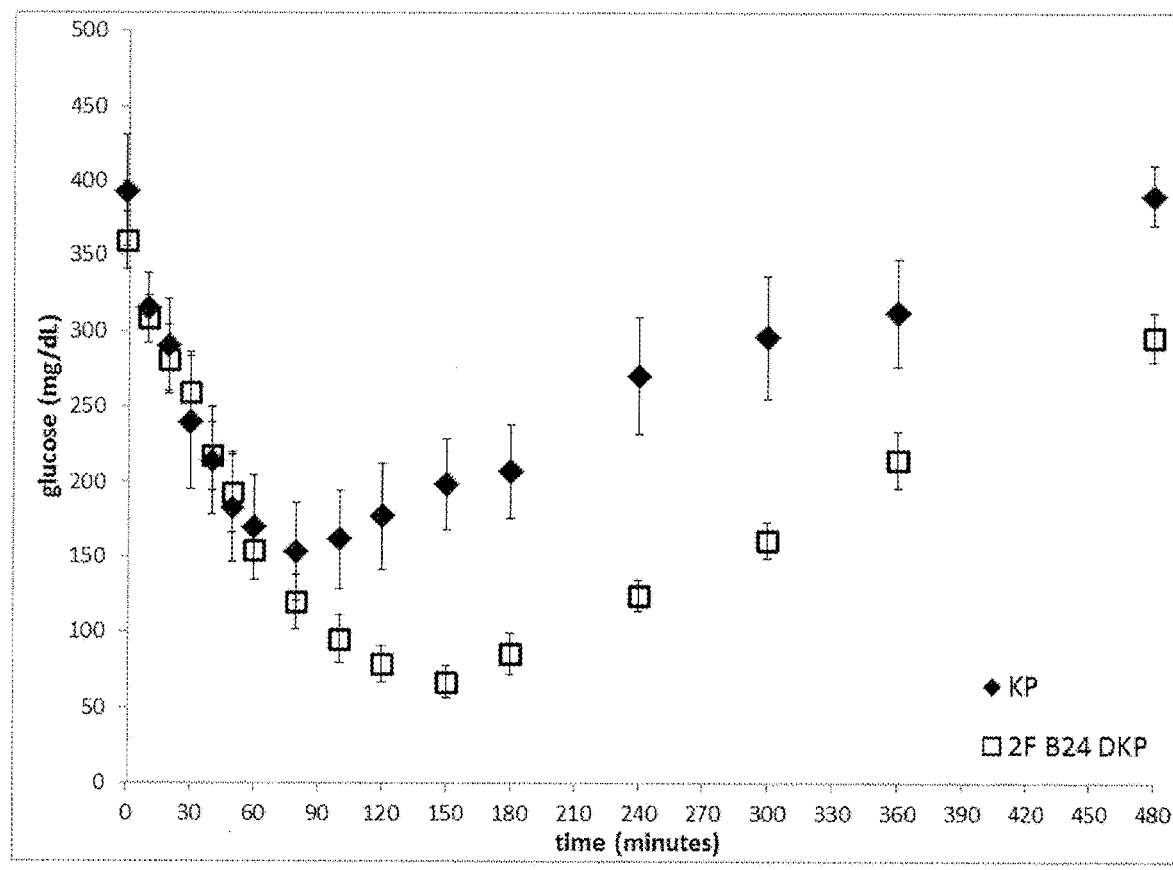
FIG. 3B is a graph showing the results of studies of glycemic response to subcutaneous injection of insulin Lispro (KP-insulin) and ortho-monofluoro-$Phe^{B24}$-DKP-insulin (2F B24 DKP, open squares) in Sprague-Dawley rats rendered diabetic by streptozotocin, at a dose of 50 μg per rat. The relative affinity of 2-F-$Phe^{B24}$-DKP-insulin is ca. 35(±5) %.
Figure 6:
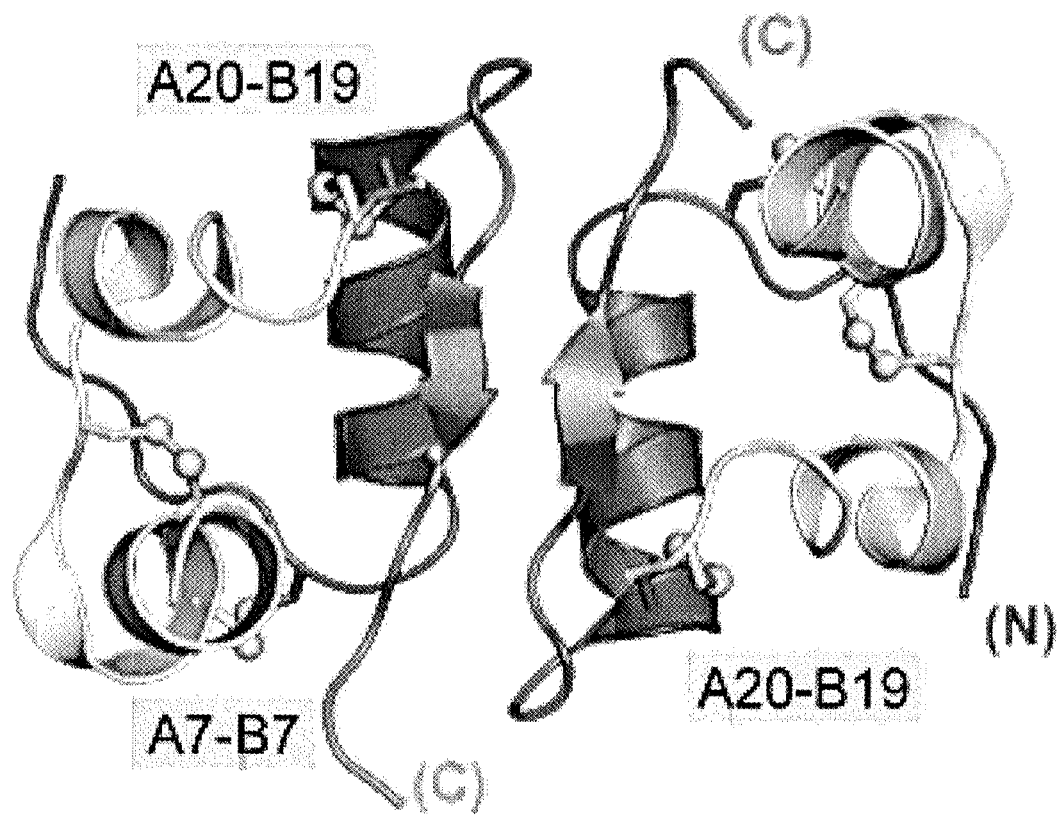
FIG. 6 is a representation of the structure of insulin dimer and core Beta-sheet. Residues B24-B28 (medium gray) for an anti-parallel Beta-sheet, repeated three times in the hexamer by symmetry. The A- and B chains are otherwise shown in light and dark gray, respectively. The position of $Phe^{B24}$ is highlighted in the arrow in dark gray. Cystines are identified by sulfur atoms that are shown as spheres. Coordinates were obtained from $T_6$ hexamer (PDB 4INS).
Figure 7:
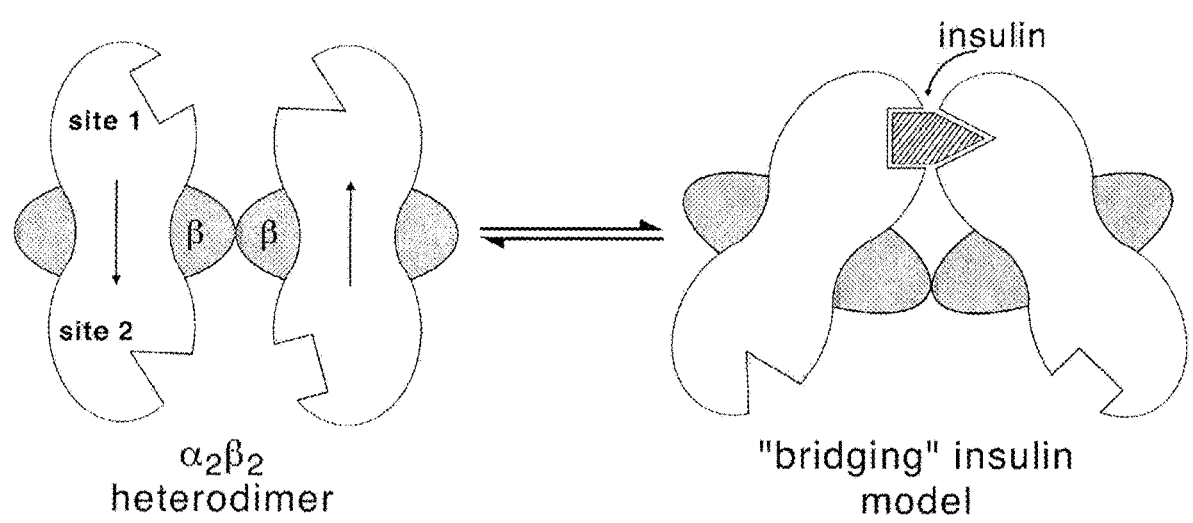
FIG. 7 is a representation of a model of the interaction of Insulin Receptor (IR) with insulin, where each a subunit of the receptor contains two distinct insulin-binding sites: Site 1 (high affinity) and Site 2 (low affinity but critical to signal propagation). Specific insulin binding bridges the two a subunits, in turn altering the orientation between β subunits, communicating a signal to the intracellular tyrosine kinase (TK) domain.
Figure 8:
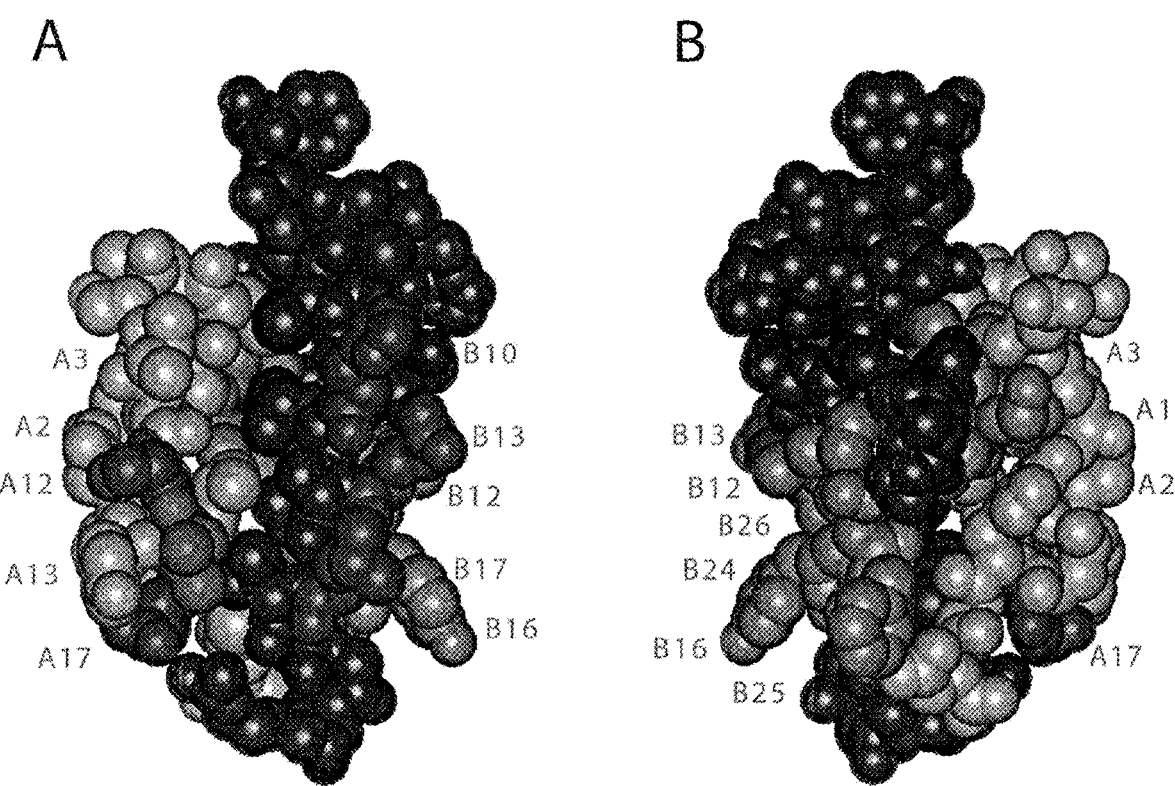
FIG. 8 is a representation of the functional surfaces of insulin including the classical receptor-binding surface of insulin which is believed to engage IR Site 1 (B12, B16, B24-B26), and its Site 2-related surface which includes hexamer contacts $Val^{B17}$ and $Leu^{A13}$; proposed Site 2 residues are shown (B13, B17, A12, A13, and A17) with addition of neighboring residue B10, which may contribute to both Sites 1 and 2. The A- and B chains are otherwise shown in light gray and dark gray, respectively.
Figure 9:
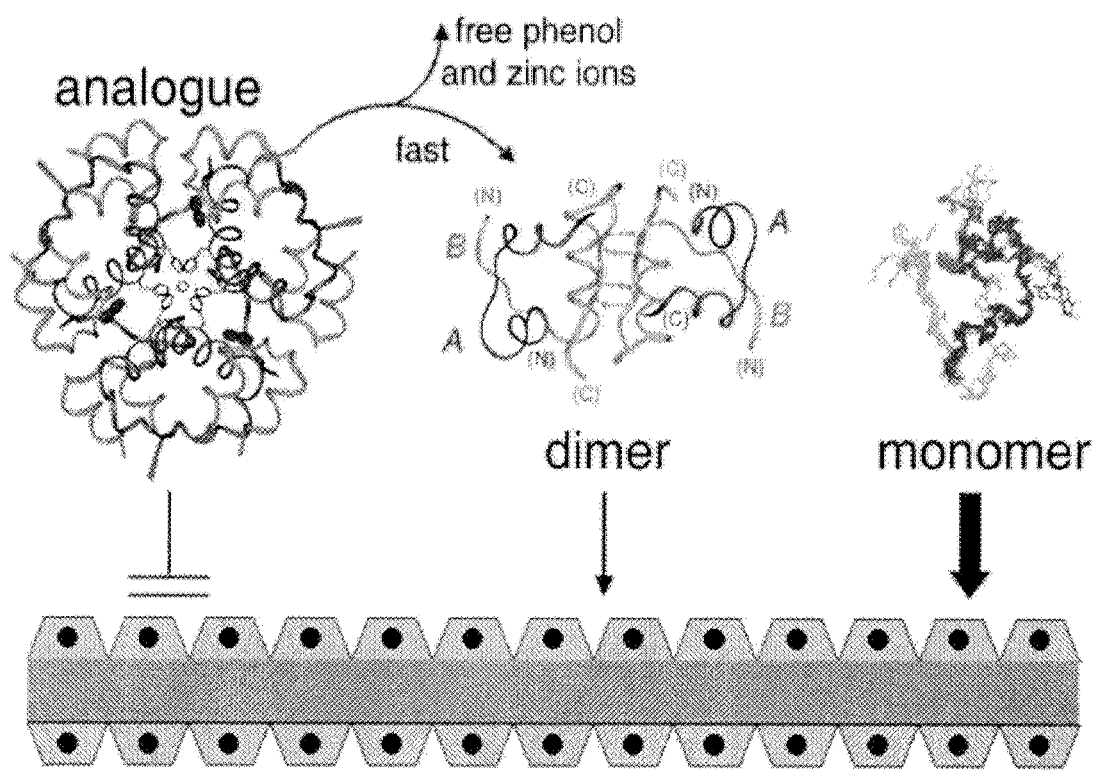
FIG. 9 is a representation of a model rationale for the design and formulation of mealtime insulin analogues. Rapid dissociation of the zinc hexamer yields dimers and monomers able to enter the capillaries. Current mealtime insulin analogs contain standard substitutions at the edge of the core Beta-sheet.
Figure 10:
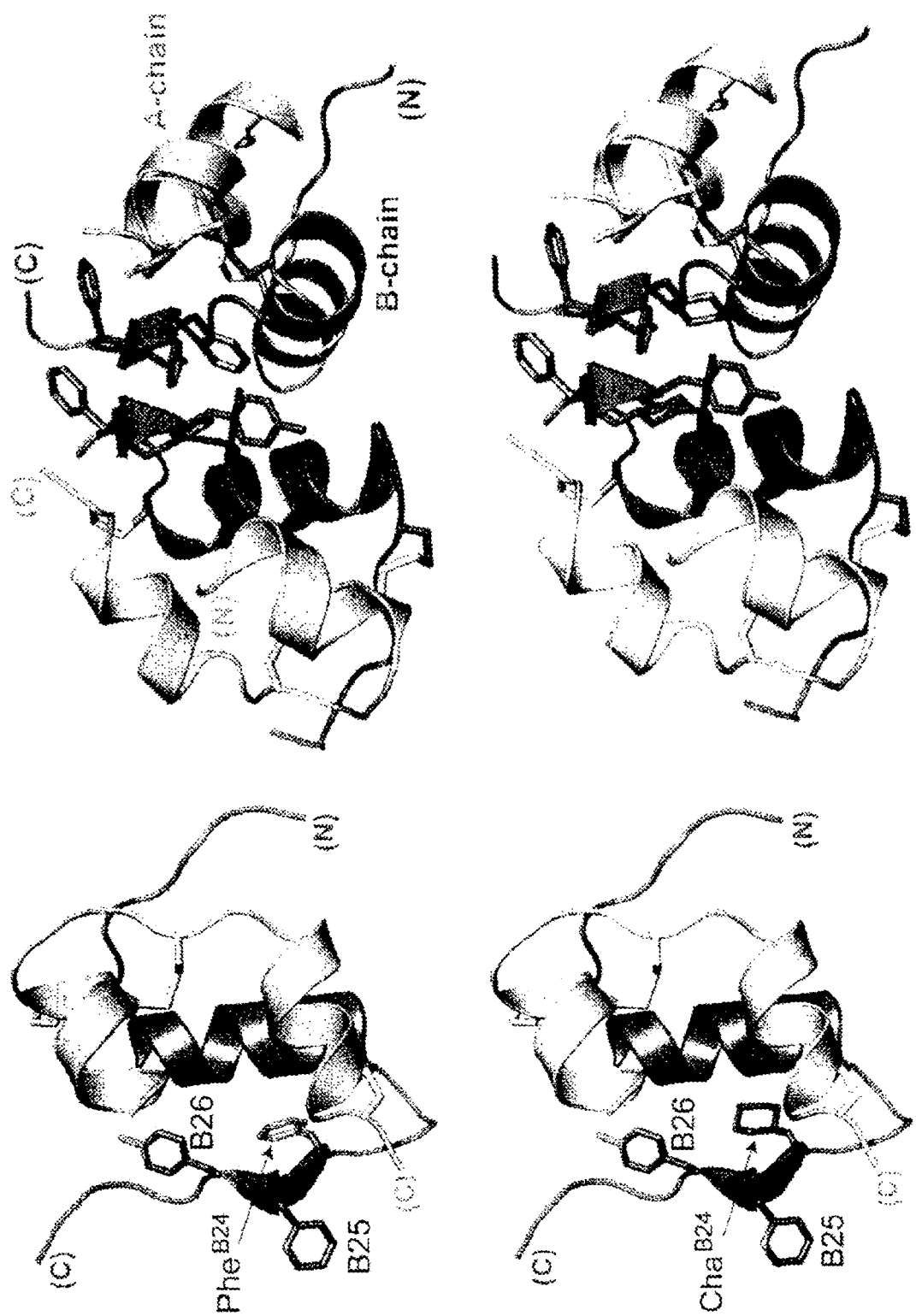
FIG. 10 is a series of views of a structural model depicting the fit of $Phe^{B24}$ and $Cha^{B24}$ within the structure of wild-type insulin.

Aromatic and non-aromatic rings differ in planarity, reflecting the presence (Phe) or absence (Cha) of π electrons as illustrated in front and side views of Phenylalanine (FIG. 2A) relative to Cyclohexanylalanine (FIG. 2B). Although not wishing to be constrained by theory, the present invention envisions that modifications at B24 that alter the weakly polar character of the ring system and/or enlarge its topographical contours would more readily be accommodated in the insulin monomer than at the dimer interface and so be associated with accelerated disassembly. In particular, because the dimer interface is characterized by multiple aromatic-aromatic interactions involving $Phe^{B24}$ and six other aromatic rings ($Tyr^{B16}$, $Phe^{B25}$, $Tyr^{B26}$, and their symmetry-related partners), the present invention further envisions that loss of aromaticity at position B24 would in general accelerate the disassembly of insulin hexamers and further accelerate the disassembly of variant hexamers containing destabilizing mutations elsewhere in the dimer- or trimer interface. Although the three-dimensional structure of a $Cha^{B24}$ variant of human insulin has not been determined, insight may be gained from rigid-body modeling based on the crystal structure of wild-type insulin (FIG. 10). A molecular model depicting the packing of $Cha^{B24}$ within an insulin monomer is shown in FIG. 10C relative to the wild-type $Phe^{B24}$ as shown in FIG. 10A. A molecular model depicting the packing of $Cha^{B24}$ within an insulin dimer interface is shown in FIG. 3D relative to the wild-type $Phe^{B24}$ as shown in FIG. 3A.

Figure 1A:
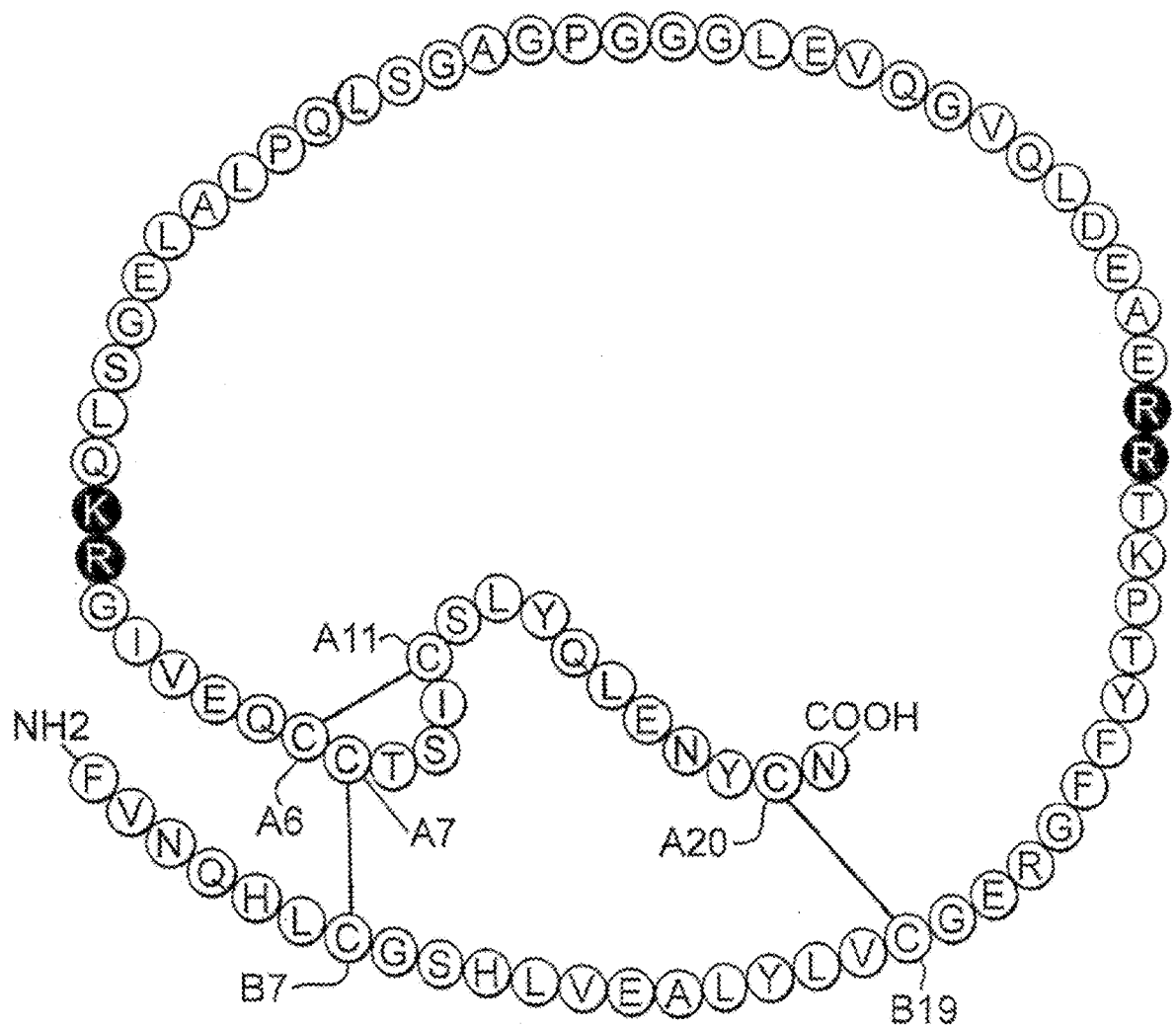
FIG. 1A is a schematic representation of the sequence of human proinsulin including the A- and B-chains and the connecting region shown with flanking dibasic cleavage sites (filled circles) and C-peptide (open circles).
Figure 1B:
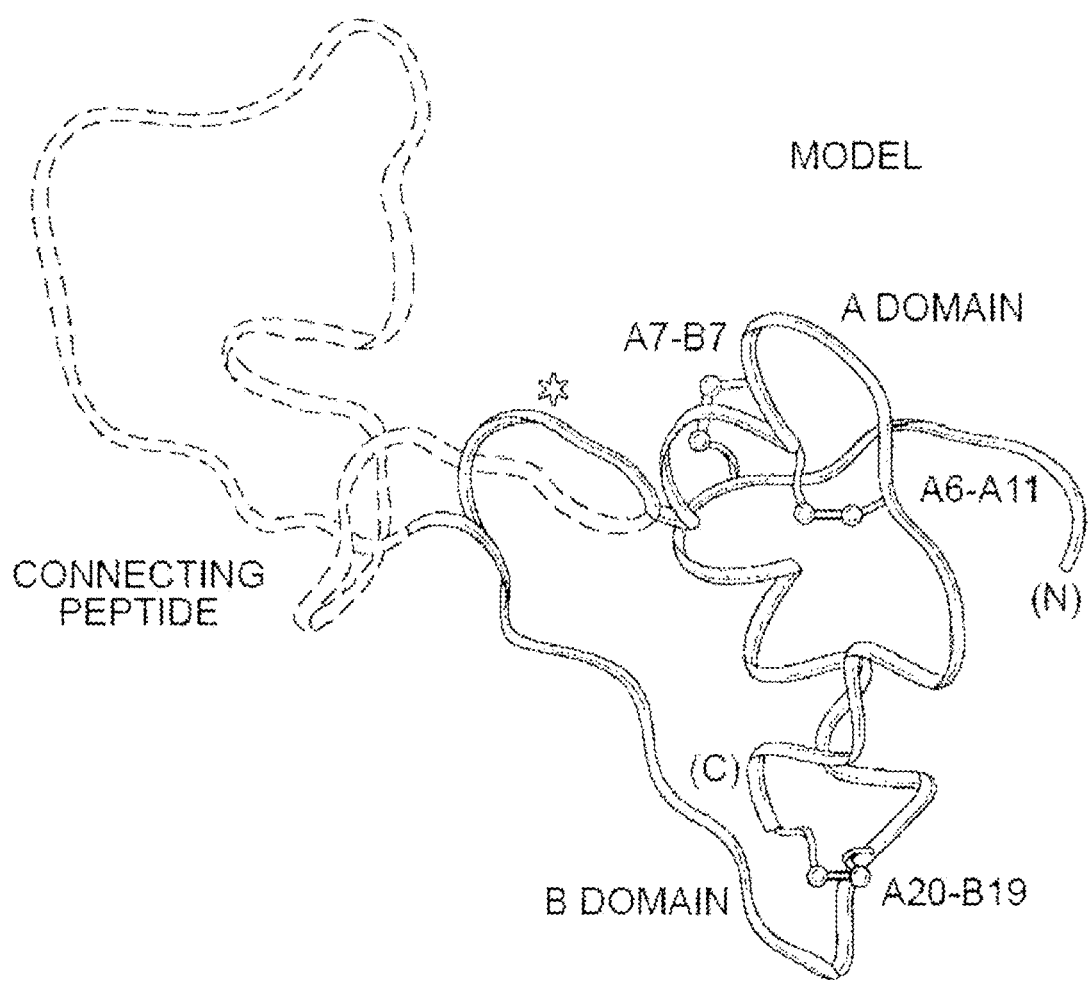
FIG. 1B is a structural model of proinsulin, consisting of an insulin-like moiety and a disordered connecting peptide (dashed line).
Figure 1C:
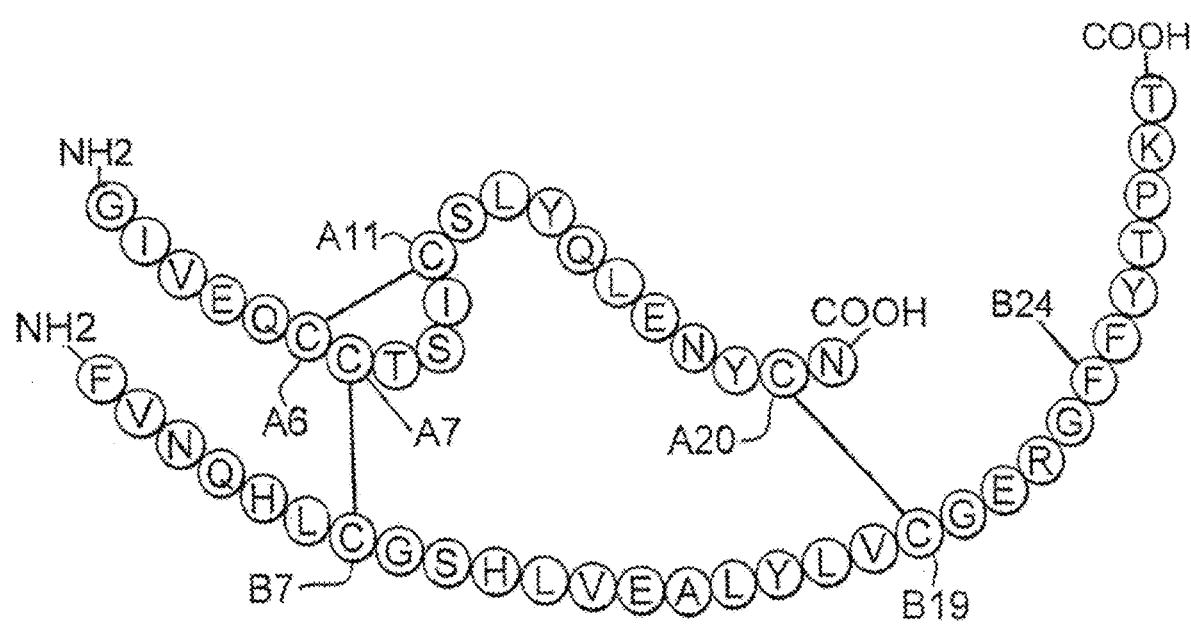
FIG. 1C is a schematic representation of the sequence of human insulin indicating the position of residue B24 in the B-chain. The top sequence is insulin A-chain which is SEQ ID NO: 2 and the bottom sequence is insulin B-chain which is SEQ ID NO: 3.
Figure 1D:
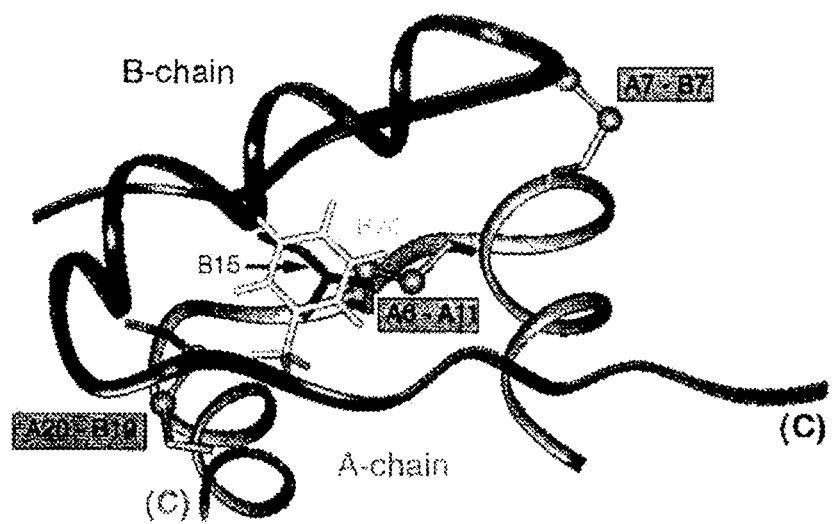
FIG. 1D is a ribbon model of an insulin monomer showing aromatic residue of $Phe^{B24}$ in relation to the three disulfide bridges. The adjoining side chains of $Leu^{B15}$ (arrow) and $Phe^{B24}$ are shown. The A- and B-chain chains are otherwise shown in light and dark gray, respectively, and the sulfur atoms of cysteines as circles.
Figure 1E:
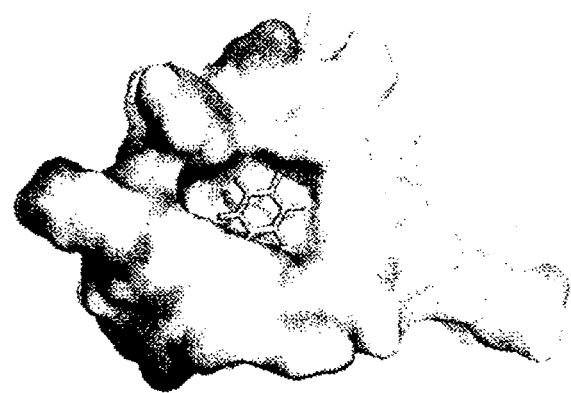
FIG. 1E is a space-filling model of insulin showing the $Phe^{B24}$ side chain within a pocket at the edge of the hydrophobic core.

The phenylalanine at B24 is an invariant amino acid in functional insulin and contains an aromatic side chain. The biological importance of $Phe^{B24}$ in insulin is indicated by a clinical mutation ($Ser^{B24}$) causing human diabetes mellitus. As illustrated in FIGS. 1D and 1E, and while not wishing to be bound by theory, $Phe^{B24}$ is believed to pack at the edge of a hydrophobic core at the classical receptor binding surface. The models are based on a crystallographic protomer (2-Zn molecule 1; Protein Databank identifier 4INS). Lying within the C-terminal β-strand of the B-chain (residues B24-B28), $Phe^{B24}$ adjoins the central α-helix (residues B9-B19). In the insulin monomer one face and edge of the aromatic ring sit within a shallow pocket defined by $Leu^{B15}$ and $Cys^{B19}$; the other face and edge are exposed to solvent (FIG. 1E). This pocket is in part surrounded by main-chain carbonyl and amide groups and so creates a complex and asymmetric electrostatic environment with irregular and loose steric borders. In the insulin dimer, and within each of the three dimer interfaces of the insulin hexamer, the side chain of $Phe^{B24}$ packs within a more tightly contained spatial environment as part of a cluster of eight aromatic rings per dimer interface ($Tyr^{B16}$, $Phe^{B24}$, $Phe^{B25}$, $Tyr^{B26}$ and their dimer-related mates). Irrespective of theory, substitution of the aromatic ring of $Phe^{B24}$ by a cyclic aliphatic ring of the same number of carbon atoms, but differing in its volume, stereo-electronic properties, and lack of planarity, provides an opportunity to preserve general hydrophobic packing within the dimer interface of the insulin hexamer while imposing distinct spatial packing constraints and perturbing the asymmetric electrostatic environment of the wild-type aromatic ring.

The present invention pertains to a non-standard modification at position B24 to improve the properties of insulin or insulin analogues with respect to rapidity of absorption following subcutaneous injection. In one instance the non-standard amino acid lacks aromaticity and its associated asymmetric distribution of partial positive and negative charges as demonstrated by substitution of the non-planar aliphatic ring system of Cyclohexanylalanine. Loss of planarity in a non-aromatic ring system is associated with a change in topographical contours and an increase in side-chain volume (FIG. 2B) relative to phenylalanine (FIG. 2A). In other instances the non-standard amino-acid substitution at B24 is accompanied by a non-standard substitution at position B29 or by three or fewer standard substitutions elsewhere in the A- or B chains.

It is envisioned that the substitutions of the present invention may be made in any of a number of existing insulin analogues. For example, the cyclic aliphatic side chain (Cha) substitution at position B24 provided herein may be made in insulin analogues such as insulin Lispro ([$Lys^{B28}$, $Pro^{B29}$]-insulin, herein abbreviated KP-insulin), insulin Aspart ($Asp^{B28}$-insulin), other modified insulins or insulin analogues, or within various pharmaceutical formulations, such as regular insulin, NPH insulin, lente insulin or ultralente insulin, in addition to human insulin. Insulin Aspart contains an $Asp^{B28}$ substitution and is sold as Novalog® whereas insulin Lispro contains $Lys^{B28}$ and $Pro^{B29}$ substitutions and is known as and sold under the name Humalog®. These analogues are described in U.S. Pat. Nos. 5,149,777 and 5,474,978, the disclosures of which are hereby incorporated by reference herein. These analogues are each known as fast-acting insulins.

In further examples, the cyclic aliphatic side chain (Cha) substitution at position B24 provided herein may be made in insulin analogues additionally comprising a TrpA13 and a Glu A8 substitution.

The amino-acid sequence of human proinsulin is provided, for comparative purposes, as SEQ ID NO: 1.

(human proinsulin)
SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn The amino-acid sequence of the A chain of human insulin is provided as SEQ ID NO: 2.

(human A chain)
SEQ ID NO: 2
Gly-Ile-Val-Glu-Gln-Cys-Cys-Thr-Ser-Ile-Cys-Ser-
Leu-Tyr-Gln-Leu-Glu-Asn-Tyr-Cys-Asn The amino-acid sequence of the B chain of human insulin is provided as SEQ ID NO: 3.

(human B chain)
SEQ ID NO: 3
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The amino-acid sequence of a B chain of human insulin may be modified with a substitution of a Cyclohexanylalanine (Cha) at position B24. An example of such a sequence is provided as SEQ. ID. NO 4.

SEQ ID NO: 4
Phe-Val-Asn-Gln-His-Leu-Cys-Gly-Ser-Xaa₄-Leu-

Val-Glu-Ala-Leu-Tyr-Leu-Val-Cys-Gly-Glu-Arg-

Gly-Xaa₁-Phe-Tyr-Thr-Xaa₂-Xaa₃-Thr
[Xaa₁ is Cha; Xaa₂ is Asp, Pro, Lys, or Arg;
Xaa₃ is Lys, Pro, or Ala; and Xaa₄ is His
or Asp]

Substitution of a Cha at position B24 may optionally be combined with non-standard substitutions at position B29 as provided in SEQ. ID. NO 5.

SEQ ID NO: 5
Phe-Val-Asn-Gln-His-Leu-Cys-Gly-Ser-Xaa₃-Leu-Val-

Glu-Ala-Leu-Tyr-Leu-Val-Cys-Gly-Glu-Arg-Gly-Xaa₁-

Phe-Tyr-Thr-Pro-Xaa₂-Thr

[Xaa₁ is Cha; Xaa₂ is Asp, Pro; Xaa₂ is
Ornithine, Diaminobutyric acid, Diaminoproprionic
acid, Norleucine, Aminobutric acid, or
Aminoproprionic acid; and Xaa₃ is His or Asp]

Further combinations of other substitutions are also within the scope of the present invention. It is also envisioned that the substitutions and/or additions of the present invention may also be combined with substitutions of prior known insulin analogues. For example, the amino-acid sequence of an analogue of the B chain of human insulin containing the Lys$^{B28}$ and Pro$^{B29}$ substitutions of insulin Lispro, in which the Cha$^{B24}$ substitution may also be introduced, is provided as SEQ ID NO: 6.

SEQ ID NO: 6
Phe-Val-Asn-Gln-His-Leu-Cys-Gly-Ser-His-Leu-

Val-Glu-Ala-Leu-Tyr-Leu-Val-Cys-Gly-Glu-Arg-

Gly-Xaa₁-Phe-Tyr-Thr-Lys-Pro-Thr
[Xaa₁ is Cha]

Similarly, the amino-acid sequence of an analogue of the B chain of human insulin containing the Asp$^{B28}$ substitution of insulin Aspart, in which the Cha$^{B24}$ substitution may also be introduced, is provided as SEQ ID NO: 7.

SEQ ID NO: 7
Phe-Val-Asn-Gln-His-Leu-Cys-Gly-Ser-His-Leu-

Val-Glu-Ala-Leu-Tyr-Leu-Val-Cys-Gly-Glu-Arg-

Gly-Xaa₁-Phe-Tyr-Thr-Asp-Lys-Thr
[Xaa₁ is Cha]

A Cha$^{B24}$ substitution may also be introduced in combination with other insulin analogue substitutions such as analogues of human insulin containing His substitutions at residues A4, A8 and/or B1 as described more fully in U.S. Pat. No. 8,343,914, the disclosure of which is incorporated by reference herein. For example, the Cha$^{B24}$ substitution may be present with His$^{A8}$ and/or His$^{B1}$ substitutions in a single-chain insulin analogue or proinsulin analogue having the amino-acid sequence represented by SEQ ID NO: 8, SEQ ID NO: 8
Xaa₁-Val-Asn-Gln-His-Leu-Cys-Gly-Ser-His-Leu- Val-Glu-Ala-Leu-Tyr-Leu-Val-Cys-Gly-Glu-Arg- Gly-Xaa₈-Phe-Xaa₂-Thr-Xaa₃-Xaa₄-Thr-Xaa₅-Gly- Ile-Val-Xaa₆-Gln-Cys-Cys-Xaa₇-Ser-Ile-Cys-Ser- Leu-Tyr-Gln-Leu-Glu-Asn-Tyr-Cys-Asn;

wherein Xaa₁ is His or Phe; wherein Xaa₂ is Tyr or Phe, Xaa₃ is Pro, Lys, or Asp; wherein Xaa₄ is Lys or Pro; wherein Xaa₆ is His or Glu; wherein Xaa₇ is His or Thr; wherein Xaa₅ is 0-35 of any amino acid or a break in the amino-acid chain; and wherein Xaa₈ is Cha; and further wherein at least one substitution selected from the group of the following amino-acid substitutions is present:
Xaa₁ is His; and
Xaa₇ is His; and
Xaa₆ and Xaa₇ together are His.

A Cyclohexanylalanine substitution at B24 and/or two amino acid addition may also be introduced into a single-chain insulin analogue as disclosed in U.S. Pat. No. 8,192, 957, the disclosure of which is incorporated by reference herein.

In still another embodiment, the B-chain insulin analogue polypeptide contains a Lysine at position B3, Glutamic acid at position B29, and Cyclohexanylalanine at position B24 as provided as SEQ ID NO: 9.

SEQ ID NO: 9
Phe-Val-<u>Lys</u>-Gln-His-Leu-Cys-Gly-Ser-His-Leu-

Val-Glu-Ala-Leu-Tyr-Leu-Val-Cys-Gly-Glu-Arg-

Gly-Xaa₁-Phe-Tyr-Thr-Pro-<u>Glu</u>-Thr.

Wherein Xaa₁ is Cyclohexanylalanine.

Cyclohexanylalanine was introduced within an engineered insulin monomer of native activity, designated KP-insulin, which contains the substitutions Lys$^{B28}$ (K) and Pro$^{B29}$ (P). These two substitutions on the surface of the B-chain are believed to impede formation of dimers and hexamers but be compatible with hexamer assembly in the presence of zinc ions and a phenolic preservative. KP-insulin is the active ingredient of Humalog®, currently in clinical use as a rapid-acting insulin analogue formulation. The sequence of the B-chain polypeptide for this variant of KP-insulin is provided as SEQ ID NO: 6. Cyclohexanylalanine was also introduced at position B24 (SEQ ID NO: 21), and separately at position B25 (SEQ ID NO: 22) as a control analogue, within an engineered insulin monomer of enhanced activity, designated DKP-insulin, which contains the substitution Asp$^{B10}$ (D) in addition to the KP substitutions Lys$^{B28}$ (K) and Pro$^{B29}$ (P) in accordance with the general scheme provided in SEQ. ID. NO 4. Cha$^{B24}$ was also introduced into non-standard human insulin analogues containing either Ornithine or Norleucine at position B29 in accordance with the general scheme provided in SEQ. ID. NO 5.

Analogues of KP-insulin and DKP-insulin were prepared by trypsin-catalyzed semi-synthesis and purified by high-performance liquid chromatography (Mirmira, R. G., and Tager, H. S., 1989. *J. Biol. Chem.* 264: 6349-6354.) This protocol employs (i) a synthetic octapeptide representing residues (N)-GF*FYT<u>K</u>PT (including modified residue (F*) and "KP" substitutions (underlined); SEQ ID NO: 12) and (ii) truncated analogue des-octapeptide[B23-B30]-insulin or, in the case of DKP-insulin analogues, Asp$^{B10}$-des-octapeptide[B23-B30]-insulin (SEQ ID NO: 10). Because the octapeptide differs from the wild-type B23-B30 sequence (GF*FYTPKT; SEQ ID NO: 11) by interchange of Pro$^{B28}$ and Lys$^{B29}$ (italics), protection of the lysine ε-amino group is not required during trypsin treatment. In brief, des-octapeptide (15 mg) and octapeptide (15 mg) were dissolved in a mixture of dimethylacetamide/1,4-butandiol/0.2 M Tris acetate (pH 8) containing 10 mM calcium acetate and 1 mM ethylene diamine tetra-acetic acid (EDTA) (35:35:30, v/v, 0.4 mL). The final pH was adjusted to 7.0 with 10 µL of N-methylmorpholine. The solution was cooled to 12° C., and 1.5 mg of TPCK-trypsin was added and incubated for 2 days at 12° C. An additional 1.5 mg of trypsin was added after 24 hr. The reaction was acidified with 0.1% trifluoroacetic acid and purified by preparative reverse-phase HPLC (C4). Mass spectrometry using matrix-assisted laser desorption/ionization time-of-flight (MALDI-TOF; Applied Biosystems, Foster City, Calif.) in each case gave expected values (not shown). The general protocol for solid-phase synthesis is as described (Merrifield et al., 1982. *Biochemistry* 21: 5020-5031). 9-fluoren-9-yl-methoxy-carbonyl (F-moc)-protected phenylalanine analogues were purchased from Chem-Impex International (Wood Dale, Ill.).

The above protocol was also employed to prepare analogues of human insulin containing Ornithine or Norleucine at position B29 and to introduce Cha$^{B24}$ in these respective contexts. The method of preparation of these analogues exploits non-standard amino-acid substitutions at position 29 to eliminate the tryptic site ordinarily present within the C-terminal octapeptide of the B chain (i.e., between Lys$^{B29}$ and Thr$^{B30}$) while maintaining a Proline at position 28. Pro$^{B28}$ contributes to the stability of the dimer interface within the insulin hexamer, and so this method of preparation provides near-isosteric models of wild-type insulin in which other modifications may conveniently be incorporated without the need for cumbersome side-chain protection.

Circular dichroism (CD) spectra were obtained at 4° C. and/or 25° C. using an Aviv spectropolarimeter (Weiss et al., *Biochemistry* 39: 15429-15440). Samples contained ca. 25 µM DKP-insulin or analogues in 50 mM potassium phosphate (pH 7.4); samples were diluted to 5 µM for guanidine-induced denaturation studies at 25° C. To extract free energies of unfolding, denaturation transitions were fitted by non-linear least squares to a two-state model as described by Sosnick et al., *Methods Enzymol.* 317: 393-409. In brief, CD data θ(x), where x indicates the concentration of denaturant, were fitted by a nonlinear least-squares program according to $$\theta(x) = \frac{\theta_A + \theta_B e^{(-\Delta G^\circ_{H_2O} - mx)/RT}}{1 + e^{-(\Delta G^\circ_{H_2O} - mx)/RT}}$$

where x is the concentration of guanidine and where $\theta_A$ and $\theta_B$ are baseline values in the native and unfolded states. Baselines were approximated by pre- and post-transition lines $\theta_A(x) = \theta_A^{H_2O} + m_A x$ and $\theta_B(x) = \theta_B^{H_2O} + m_B x$. The m values obtained in fitting the variant unfolding transitions are lower than the m value obtained in fitting the wild-type unfolding curve. To test whether this difference and apparent change in $\Delta G_u$ result from an inability to measure the CD signal from the fully unfolded state, simulations were performed in which the data were extrapolated to plateau CD values at higher concentrations of guanidine; essentially identical estimates of $\Delta G_u$ and m were obtained.

Relative activity is defined as the ratio of the hormone-receptor dissociation constants of analogue to wild-type human insulin, as measured by a competitive displacement assay using $^{125}$I-human insulin. Microtiter strip plates (Nunc Maxisorb) were incubated overnight at 4° C. with AU5 IgG (100 al/well of 40 mg/ml in phosphate-buffered saline). Binding data were analyzed by a two-site sequential model. Data were corrected for nonspecific binding (amount of radioactivity remaining membrane associated in the presence of 1 µM human insulin. In all assays the percentage of tracer bound in the absence of competing ligand was less than 15% to avoid ligand-depletion artifacts. Representative data are provided in FIG. 11.

To assess hypoglycemic potencies of KP-insulin (or DKP-insulin) analogues relative to KP-insulin or wild-type insulin in vivo, male Lewis rats (mean body mass ~300 grams) were rendered diabetic by treatment with streptozotocin. (This model provides a probe of potency but not degree of acceleration of pharmacokinetics as (i) wild-type insulin, KP-insulin, and Asp$^{B28}$ insulin exhibit similar patterns of effects of blood glucose concentration and (ii) these patterns are unaffected by the presence of absence of zinc ions in the formulation at a stoichiometry sufficient to ensure assembly of insulin hexamers.) Protein solutions containing wild-type human insulin, insulin analogues, or buffer alone (protein-free sterile diluent obtained from Eli Lilly and Co.; composed of 16 mg glycerin, 1.6 mg meta-cresol, 0.65 mg phenol, and 3.8 mg sodium phosphate PH 7.4.) were injected subcutaneously, and resulting changes in blood glucose were monitored by serial measurements using a clinical glucometer (Hypoguard Advance Micro-Draw meter). To ensure uniformity of formulation, insulin analogues were each re-purified by reverse-phase high-performance liquid chromatography (rp-HPLC), dried to powder, dissolved in diluent at the same maximum protein concentration (300 µg/mL) and re-quantitative by analytical C4 rp-HPLC; dilutions were made using the above buffer. Rats were injected subcutaneously at time t=0 with 20 µg insulin in 100 al of buffer per 300 g rat. This dose corresponds to ca. 67 rig/kg body weight, which corresponds in international units (IU) to 2 IU/kg body weight. Dose-response studies of KP-insulin indicated that at this dose a near-maximal rate of glucose disposal during the first hour following injection was achieved. Five rats were studied in the group receiving Cha$^{B24}$-KP-insulin (SEQ ID NOS: 2 and 6), and five different rats were studied in the control group receiving KP-insulin (SEQ ID NOS: 2 and 20); these rats were randomly selected from a colony of 30 diabetic rats. The two groups exhibited similar mean blood glucose concentrations at the start of the experiment. Blood was obtained from clipped tip of the tail at time 0 and every 10 minutes up to 90 min. The efficacy of insulin action to reduce blood glucose concentration was calculated using the change in concentration over time (using least-mean squares and initial region of linear fall) divided by the concentration of insulin injected. The initial rate of change in blood glucose concentration in the group receiving KP-insulin was −127.1±24.6 mg/dl/h (mean±standard error of the mean); the initial rate of change in the group receiving Cha$^{B24}$-KP-insulin was −113.5±21.7 mg/dl/h. Any differences were not statistically significant. These data thus suggest that the biological potency of Cha$^{B24}$-KP-insulin is equivalent to that of KP-insulin in a zinc hexamer formulation.

The kinetic stability of insulin analogue hexamers was assessed at 25° C. relative to that of the wild-type human insulin hexamer as a cobalt ($Co^{2+}$) complex in the presence of 2.2 cobalt ions per hexamer and 50 mM phenol in a buffer consisting of 10 Tris-HCl (pH 7.4). The assay, a modification of the procedure of Beals et al. (Birnbaum, D. T., Kilcomons, M. A., DeFelippis, M. R., & Beals, J. M. Assembly and dissociation of human insulin and $Lys^{B28}$ $Pro^{B29}$-insulin hexamers: a comparison study. *Pharm Res.* 14, 25-36 (1997)), employs optical absorbance at 500-700 nm to monitor the $R_6$-hexamer-specific d-d transitions characteristic of tetrahedral cobalt ion coordination. Although the solution at equilibrium contains a predominance of cobalt insulin hexamers or cobalt insulin analogue hexamers, this equilibrium is characterized by opposing rates of insulin assembly and disassembly. To initiate the assay, the solution is made 2 mM in ethylene-diamine-tetra-acetic acid (EDTA) to sequester free cobalt ions. The time course of decay of the $R_6$-specific absorption band on addition of EDTA provides an estimate of the rate of hexamer disassembly. Whereas wild-type insulin (SEQ ID NOS: 2 and 3) exhibited a time constant of 419±51 seconds, KP-insulin (SEQ ID NOS: 2 and 20) exhibited a time constant of 114±13 seconds in accordance with its accelerated pharmacokinetics. Strikingly, the time constant for $Cha^{B24}$-KP-insulin (SEQ ID NOS: 2 and 6) was found to be 49±5 seconds, predicting a further acceleration of pharmacokinetics in human patients. Stated differently, $Cha^{B24}$-KP-insulin is almost as accelerated in its disassembly relative to KP-insulin, as KP-insulin is accelerated relative to wild type human insulin.

The far-ultraviolet circular dichroism (CD) spectrum of the $Cha^{B24}$ analogue is similar to those of the parent analogues. Modified B24 residues were introduced within the context of KP-insulin (SEQ ID NO: 6), DKP-insulin (SEQ ID NO: 21), and non-standard analogues of human insulin in which $Lys^{B29}$ was substituted by Ornithine or Norleucine (SEQ ID NO: 5). Activity values shown are based on ratio of hormone-receptor dissociation constants relative to human insulin; the activity of human insulin is thus 1.0 by definition. Standard errors in the activity values were in general less than 25%. Free energies of unfolding ($\Delta G_u$) at 25° C. were estimated based on a two-state model as extrapolated to zero denaturant concentration. Lag time indicates time (in days) required for initiation of protein fibrillation on gentle agitation at 30° C. in zinc-free phosphate-buffered saline (pH 7.4).

The baseline thermodynamic stability of KP-insulin, as inferred from a two-state model of denaturation at 25° C., is 3.0±0.1 kcal/mole. CD-detected guanidine denaturation studies indicate that the $Cha^{B24}$ substitution is associated with a small decrement in thermodynamic stability in the context of KP-insulin ($\Delta\Delta G_u$ 0.3±0.2 kcal/mole) and in the context of DKP-insulin ($\Delta\Delta G_u$ 0.4±0.2 kcal/mole). Nonetheless, the physical stability of the $Cha^{B24}$ KP analogue was found to be similar to or greater than that of KP-insulin as evaluated in triplicate during incubation in 300 μM phosphate-buffered saline (PBS) at pH 7.4 at 30° C. under gentle agitation. The samples were observed for 20 days or until signs of precipitation or frosting of the glass vial were observed. Whereas the three tubes of KP-insulin became cloudy in 10, 13, and 16 days, respectively, the three tubes of $Cha^{B24}$-KP-insulin became cloudy in 13, 15, and 20 days. These data exhibit a trend toward greater resistance to physical degradation by the $Cha^{B24}$ analogue.

Dissociation constants ($K_d$) were determined as described by Whittaker and Whittaker (2005. *J. Biol. Chem.* 280: 20932-20936), by a competitive displacement assay using $^{125}I$-$Tyr^{A14}$-insulin (kindly provided by Novo-Nordisk) and the purified and solubilized insulin receptor (isoform B or A) in a microtiter plate antibody capture assay with minor modification; transfected receptors were tagged at their C-terminus by a triple repeat of the FLAG epitope (DYKDDDDK; SEQ ID NO: 23) and microtiter plates were coated by anti-FLAG M2 monoclonal antibody (Sigma). The percentage of tracer bound in the absence of competing ligand was less than 15% to avoid ligand-depletion artifacts. Binding data were analyzed by non-linear regression using a heterologous competition model (Wang, 1995, *FEBS Lett.* 360: 111-114) to obtain dissociation constants. Results are provided in Table 1 ($Cha^{B24}$ KP-insulin analogue relative to KP-insulin) and Table 2 ($Cha^{B25}$-DKP-insulin relative to DKP-insulin); dissociation constants are provided in units of nanomolar. (The two studies were conducted on different dates with different preparations of insulin receptor (IR isoform B; IR-B) and IGF receptor (IGF-1R) and so are tabulated independently.) The $Cha^{B24}$ modification of KP-insulin reduces IR-B receptor-binding affinities by between twofold and threefold; such small reductions are typically associated with native or near-native hypoglycemic potencies in vivo as demonstrated herein in diabetic Lewis rats. No significant increase was observed in the cross-binding of $Cha^{B24}$-KP-insulin to IGF-1R. The $Cha^{B24}$ modification of DKP-insulin reduces IR-B receptor-binding affinities by less than twofold; a trend toward increased cross-binding to IGF-1R was observed near the limit of statistical significance. $Cha^{B24}$-DKP-insulin was not tested in rats. The affinity of $Cha^{B25}$-DKP-insulin for IR-B was markedly impaired (binding to IR-B decreased by more than tenfold) in accordance with classical structure-activity relationships in insulin. The distinct site-specific effects of a Phe-*Cha substitution (well tolerated at B24 but not at B25) presumably reflect the different structural roles of these aromatic side chains at the hormone-receptor interface.

TABLE 1

Binding of Insulin Analogues to Insulin Receptor and IGF Receptor

| Protein | IR-B binding | IGF-1R binding |
|---|---|---|
| insulin | 0.045 ± 0.007 nM | 5.1 ± 0.8 nM |
| KP-insulin | 0.093 ± 0.012 nM | 5.0 ± 0.6 nM |
| $Cha^{B24}$-KP-insulin | 0.171 ± 0.022 nM | 4.3 ± 0.7 nM |

IR-B, B isoform of the insulin receptor;
IGF-1R, Type 1 IGF receptor

TABLE 2

Binding of Insulin Analogues to Insulin Receptor and IGF Receptor

| Protein | IR-B binding | IGF-1R binding |
|---|---|---|
| DKP-insulin | 0.020 ± 0.003 nM | 3.1 ± 0.51 nM |
| $Cha^{B24}$-DKP-insulin | 0.032 ± 0.005 nM | 1.4 ± 0.22 nM |
| $Cha^{B25}$-DKP-insulin | 0.350 ± 0.050 nM | ND |

IR-B, B isoform of the insulin receptor.
ND, not determined.

The binding affinities of analogues containing the non-standard amino acids Ornithine or Norleucine at position B29 were similarly tested, both with and without a Cha substitution at B24. Results are provided in Table 3 as a percentage of the binding affinity of human insulin for human insulin receptor isoform A (hIR-A), human insulin receptor isoform B (hIR-B), and human IGF receptor (hIGF- 1R); asterisks indicate values indistinguishable from 100% (wild-type) given experimental error. Whereas Orn$^{B29}$ has similar binding affinities for each receptor as wild-type insulin (asterisks), Nle$^{B29}$ confers a small decrease in affinity for hIR-B and IGF-1R relative to wild type insulin. An analogue containing Orn$^{B29}$ in combination with Cha$^{B24}$, however, had decreased binding affinity for both isoforms of insulin receptor and slightly increased affinity for hIGF-1R (possibly non-significant given experimental error). The Cha$^{B24}$, Nle$^{B29}$ analogue had similar binding affinity for hIGF-1R as the Nle$^{B29}$ only analogue, but had decreased binding affinity for hIR-B. We highlight the modesty of these changes in affinity as the observed range of in vitro hIR affinities are in each case in accordance with expected in vivo hypoglycemic potencies similar to those of wild-type insulin (i.e., as tested in a rat model); similarly, the range of in vitro IGF-1R affinities are within the range of relative affinities exhibited by insulin analogs in current clinical use. These data provide evidence that substitutions Orn$^{B29}$ and Nle$^{B29}$ have utility in semi-synthetic insulin formulations intended for therapeutic use, either alone or in combination with second-site modifications such as Cha$^{B24}$.

TABLE 3

Relative Binding Affinity of
Insulin Analogues to Insulin Receptor and IGF Receptor

| Protein | hIR-A binding | hIR-B binding | hIGF-1R binding |
|---|---|---|---|
| Insulin | 100 | 100 | 100 |
| Cha$^{B24}$, Nle$^{B29}$ | 50 | 36 | 62 |
| Cha$^{B24}$, Orn$^{B29}$ | 58 | 53 | 134* |
| Nle$^{B29}$ | ND | 67 | 61 |
| Orn$^{B29}$ | 95* | 105* | 115* | hIR-A, A isoform of human insulin receptor;
hIR-B, B isoform of human insulin receptor;
hIGF-1R, human IGF receptor;
ND, not determined;
percent errors are in general less than 20% of the values given.
Asterisks indicate values whose 95% confidence intervals include 100 and so may be indistinguishable from wild-type.

Figure 12:
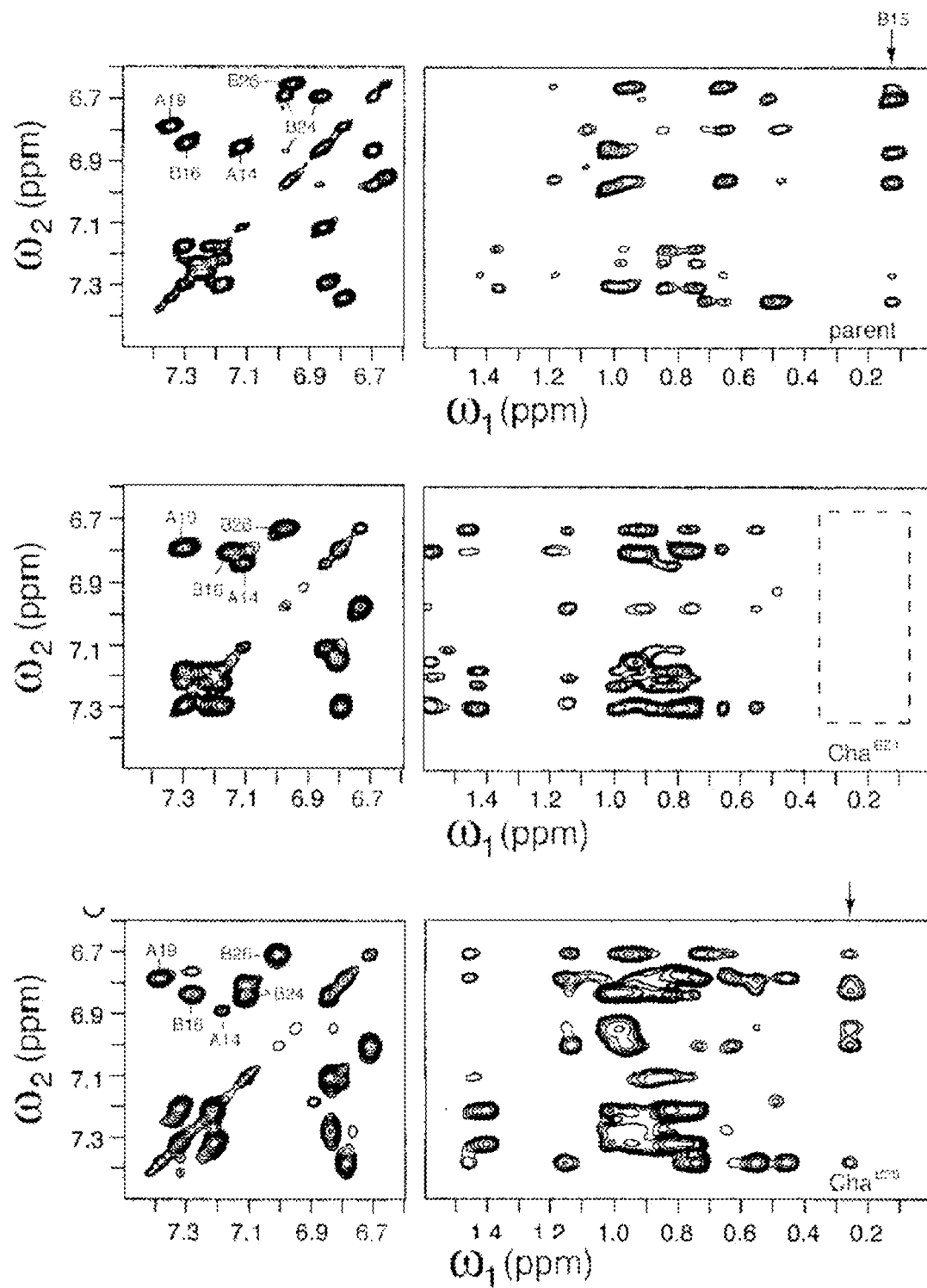
FIG. 12 provides 2D $^1$H-NMR NOESY spectra of DKP-insulin (FIG. 12A), $Cha^{B24}$-DKP-insulin (FIG. 12B), and $Cha^{B25}$-DKP-insulin (FIG. 12C), each recorded at 700 MHz at 32° C. and pD 7.0. (Left) TOCSY spectrum of aromatic region. Resonance assignments are as indicated. (Right) NOESY spectrum providing inter-proton contacts between aromatic protons (vertical axis) and aliphatic protons (horizontal axis). Empty box in FIG. 12B highlights absence of ring-current-shifted resonances due to non-aromatic nature of $Cha^{B24}$; arrows in FIG. 12A and FIG. 12C indicate characteristic upfield shift of $Leu^{B15}$ methyl resonance due to ring current of $Phe^{B24}$. The disorder of $Phe^{B25}$ on the surface of an insulin monomer by contrast attenuates its ring-current effects.

Two-dimensional $^1$H-NMR spectra have been obtained of Cha$^{B24}$ and Cha$^{B25}$ analogues of DKP-insulin (FIG. 12). Whereas the spectrum of Cha$^{B25}$-DKP-insulin is similar to that of DKP-insulin in accordance with past studies suggesting that the ensemble-averaged aromatic ring-current effects of Phe$^{B25}$ are negligible in an insulin monomer, aliphatic substitution of Phe$^{B24}$ leads to attenuation of Phe$^{B24}$-related ring current effects. Qualitative interpretation of these spectra is nonetheless suggestive of native-like structures. Further evidence for native-like packing of Cha$^{B24}$ was provided by the crystallization of [Cha$^{B24}$, Orn$^{B29}$]-insulin under conditions that routinely yields crystals of wild-type zinc insulin hexamers.

Figure 13A:
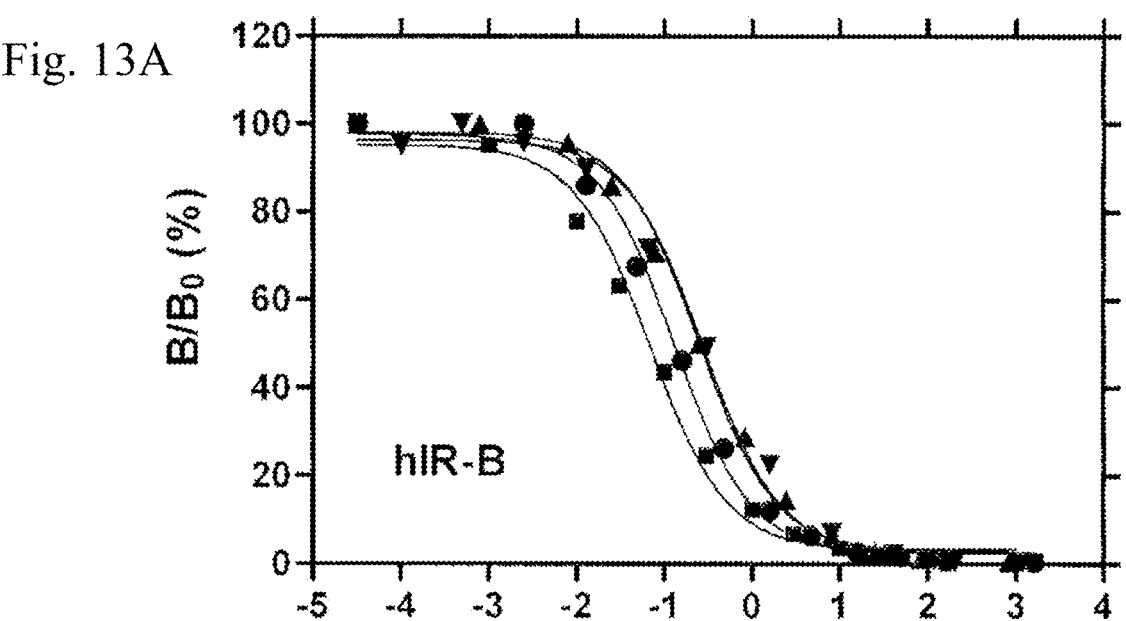
FIG. 13A is a graph showing the results of receptor-binding studies of wild type human insulin (■), KP-insulin (●), $Cha^{B24}$-KP-insulin (▲) or $Glu^{A8}$-$Cha^{B24}$-KP-insulin (▼) using isolated insulin receptor (isoform B).
Figure 13B:
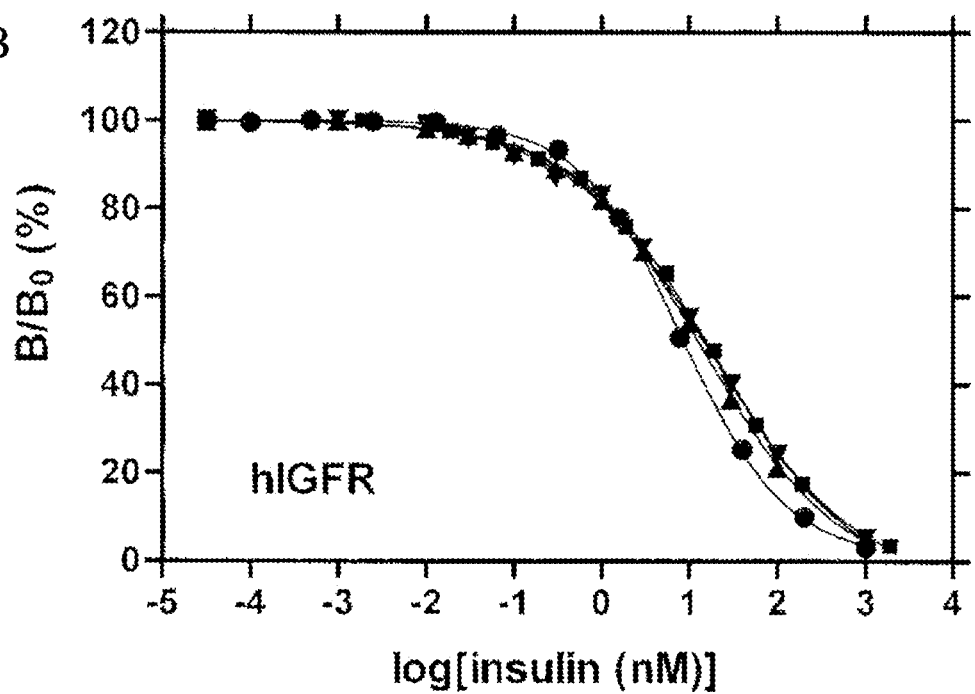
FIG. 13B is a graph showing the results of receptor-binding studies of wild type human insulin (■), KP-insulin (●), $Cha^{B24}$-KP-insulin (▲) or $Glu^{A8}$-$Cha^{B24}$-KP-insulin (▼) using human IGF-1 receptor.

Insulin analogues additionally containing a Cha$^{B24}$ substitution in a Lys$^{B28}$, Pro$^{B29}$ analogue (SEQ ID NO: 6) were created with either a wild type A-chain (SEQ ID NO: 2) or an A-chain containing a Glu$^{48}$ substitution (SEQ ID NO: 19). The results of competitive displacement assays using $^{125}$I-labeled insulin as a tracer assays for human insulin receptor isoform B and human type 1 insulin-like growth factor receptor (IGFR-1) are provided in FIGS. 13A and 13B, respectively. As shown in FIG. 13A, the affinities of Cha$^{B24}$-KP-insulin (▲) and Glu$^{48}$-Cha$^{B24}$-KP-insulin (▼) are similar to that of KP-insulin (●). Similarly, cross-binding of Cha$^{B24}$-KP-insulin and Glu$^{48}$-Cha$^{B24}$-KP-insulin to IGFR-1 is within the margin of error for that of KP insulin (FIG. 13B).

CD spectra of Cha$^{B24}$-KP-insulin and Glu$^{48}$-Cha$^{B24}$-KP-insulin resemble that of KP-insulin. 2D $^1$H-NMR spectra of Cha$^{B24}$-KP-insulin retain native-like long-range NOEs but differ in pattern of chemical shifts in accord with the loss of the Phe$^{B24}$ ring current. We measured the free energies of unfolding of Cha$^{B24}$-KP-insulin and Glu$^{48}$-Cha$^{B24}$-KP-insulin relative to KP-insulin in a zinc-free buffer at pH 7.4 and 25° C. (10 mM potassium phosphate and 50 mM KCl). This assay utilized CD detection of guanidine-induced denaturation as probed at 222 nm. Values of $\Delta G_u$ were estimated on the basis of a 2-state model. For Cha$^{B24}$-KP-insulin a possible slight decrease in stability was seen that was within experimental error ($\Delta\Delta G_u$ 0.1±0.2 kcal/mole); for Glu$^{48}$-Cha$^{B24}$-KP-insulin an increase was observed ($\Delta\Delta G_u$ 0.5±0.2 kcal/mole). This assay predicts resistance to chemical degradation similar to or greater than that of Humalog®.

The respective fibrillation lag times of KP-insulin, Cha$^{B24}$-KP-insulin and Glu$^4$-Cha$^{B24}$-KP-insulin under monomeric conditions at 45° C. were investigated. The proteins were made 60 μM in phosphate-buffered saline at pH 7.4 in the absence of zinc ions. Fibrillation was detected by enhancement of Thioflavin T (ThT) fluorescence and onset of cloudiness in the solution. Whereas KP-insulin (N=3 vials) formed fibrils within 2 days, Cha$^{B24}$-KP-insulin (N=3 vials) formed fibrils on day 4; solutions of Glu$^{48}$-Cha$^{B24}$-KP-insulin (N=2 vials) were formed fibrils on day 7. These data strongly suggest that the analogues provided by the claimed invention will exhibit physical stabilities at least as great as Humalog® or greater.

The EDTA sequestration assay described above was also used exploits these spectroscopic features as follows. At time t=0 a molar excess of EDTA is added to a solution of R$_6$ insulin hexamers or insulin analog hexamers. Although EDTA does not itself attack the hexamer to strip it of metal ions, any Co$^{2+}$ ions released in the course of transient hexamer disassembly become trapped by the chelator and thus unavailable for reassembly. The rate of disappearance of the blue color (the tetrahedral d-d optical transition at 574 nm of the R-specific insulin-bound Co$^{2+}$) thus provides an optical signature of the kinetics of hexamer disassembly.

Respective exponential dissociation curves yield half-lives of 419±51 sec (wild-type insulin), 113±13 sec (KP-insulin), and 49±5 sec (Cha$^{B24}$-KP-insulin). These differences are dramatic. Similar findings were observed in recent studies of Glu$^{48}$-Cha$^{B24}$-KP-insulin; indeed, its half life was 50% shorter than that of Cha$^{B24}$-KP-insulin, indicating that the stabilizing A-chain substitution Glu$^{48}$ (on the hexamer surface distant from the dimer interface) does not compromise, and may further accelerate, its rate of disassembly relative to Cha$^{B24}$-KP-insulin. Because diffusion of zinc ions from the subcutaneous depot is analogous to in vitro sequestration of cobalt ions in the assay, these findings predict that Cha$^{B24}$-KP-insulin and Glu$^{48}$-Cha$^{B24}$-KP-insulin will exhibit ultra-rapid PK/PD properties.

Cha$^{B24}$-KP-insulin was was tested in 2 pigs and exhibited similar potency (consistent with the rat studies) and a trend toward ultra-rapid PD. Late $t_{1/2max}$ values of 211±11 (Humalog®) and 172±13 min (Cha$^{B24}$-KP-insulin) were observed (p=0.20). Further, a 2-fold reduction was seen in the tail of insulin action (AUC above baseline infusion rate 4 mg/kg/min) between 3-5 hours post-injection which almost achieved statistical significance (p=0.07) despite the limited sample size.

An individual pig whose response to Humalog® was discovered to be unusually slow (initial time to half-maximal PD (initial $t_{1/2max}$) 81 min) was used to test the PD of the Cha$^{B24}$ analogues. Although a single individual, this pig was of potential interest as a model for the variability in PK/PD often observed among human patients in whom analogous half-maximal PD times as prolonged as 90 min have been documented. Remarkably, in this pig, Cha$^{B24}$-KP-insulin and Glu$^{A8}$-Cha$^{B24}$-KP-insulin exhibited initial initial $t_{1/2max}$ times of 62 and 49 min, respectively; the more rapid PD of Glu$^{A8}$-Cha$^{B24}$-KP-insulin is in accordance with the EDTA sequestration assay.

Synthetic genes encoding insulin analogues having altered Site-2 regions have been prepared in a subset of cases and cloned in *Pichia pastoris*. For production of two-chain insulin analogues, a 53-residue mini-proinsulin precursor was expressed, folded, and secreted by *P. pastoris* by means of an N-terminal signal peptide essentially as described (Kjeldsen T, Pettersson A F, Hach M. The role of leaders in intracellular transport and secretion of the insulin precursor in the yeast *Saccharomyces cerevisiae. J. Biotechnol.* 75, 195-208 (1999)). The codon encoding position A13 was altered by site-directed mutagenesis to encode Trp, Tyr, His, or Glu. Trp$^{A13}$ and Tyr$^{A13}$ analogues (SEQ. ID. NO:25) were selected for initial characterization.

Figure 14A:
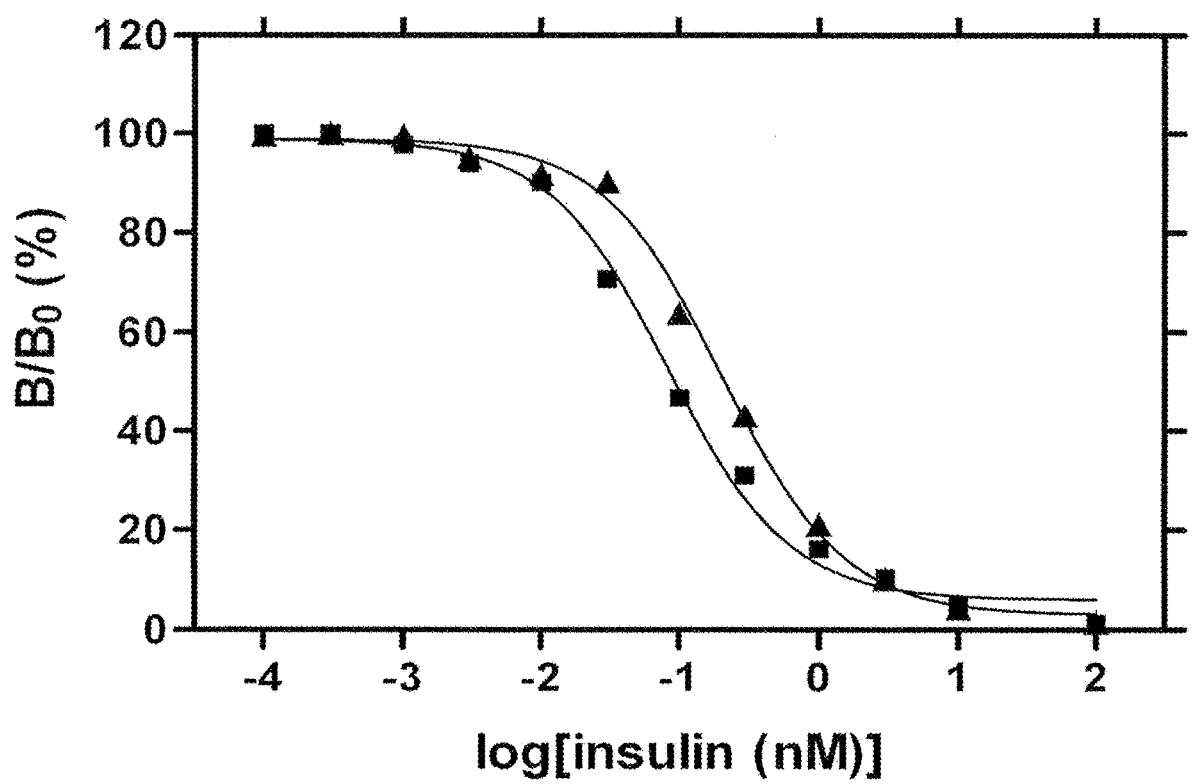
FIG. 14A is a graph of the results of competitive binding assays for $Trp^{A13}$-KP-insulin (triangles) and KP-insulin (squares) using immobilized lectin-purified isoform B of the human insulin receptor.
Figure 14B:
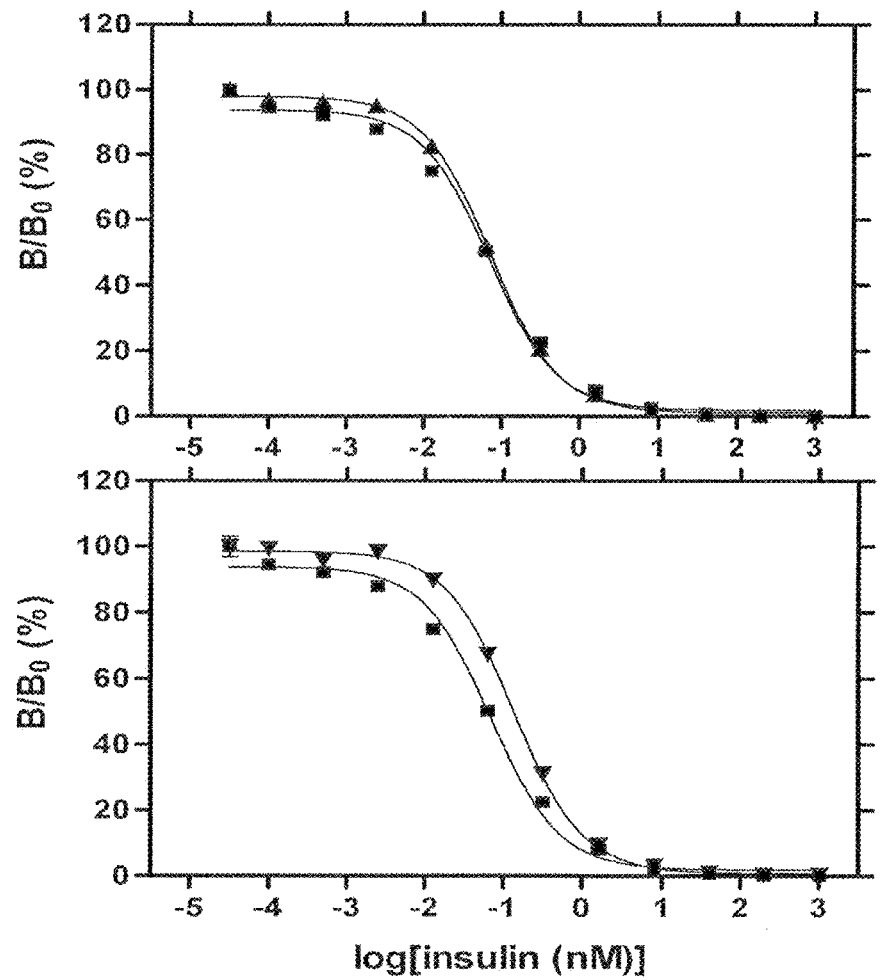
FIG. 14B is a pair of graphs of the results of competitive binding assays using immobilized lectin-purified isoform B of the human insulin receptor. The top panel shows a comparison of $Trp^{A13}$-KP-insulin (upright triangles) and wild type human insulin (squares). The bottom panel shows a comparison of 4-Cl-PheB24 derivative of TrpA13-KP-insulin (inverted triangles and wild type human insulin (squares).
Figure 15A:
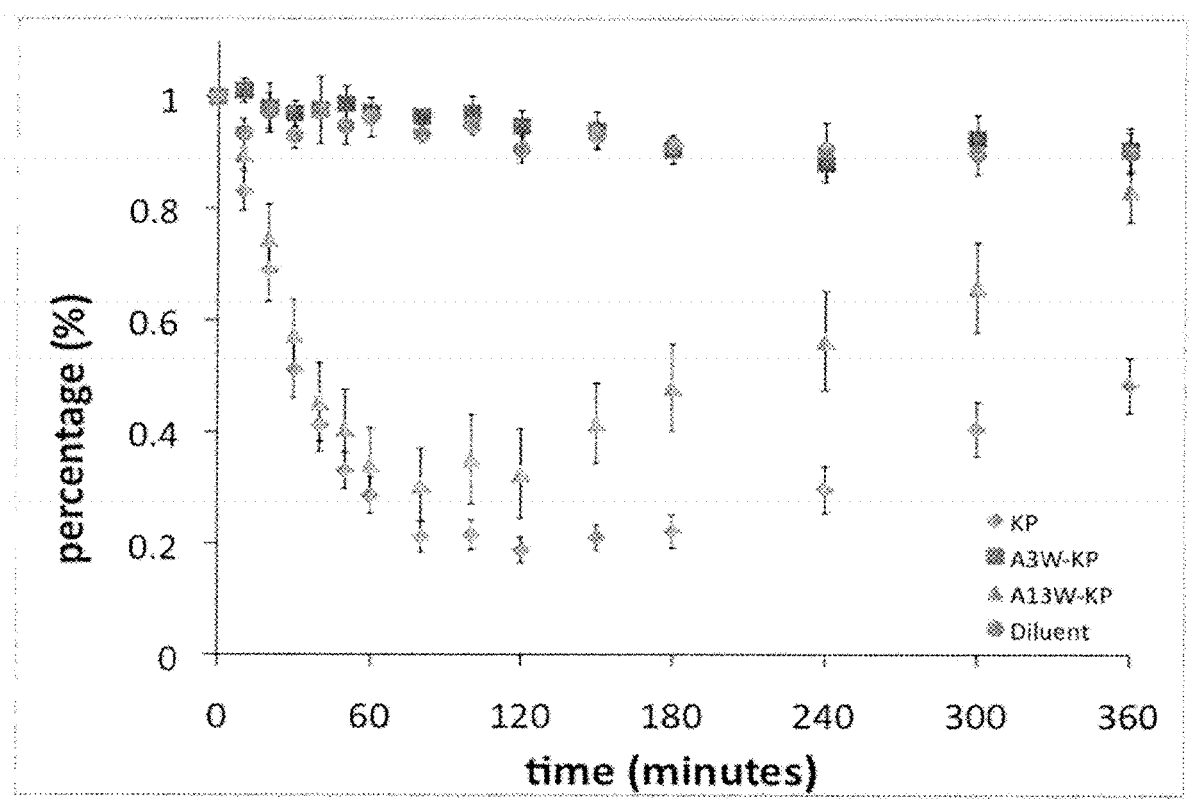
FIG. 15A is a graph showing the fall of blood glucose levels over time as a percentage relative to the mean initial value (ca. 400 mg/dl) for $Trp^{A13}$-KP-insulin (triangles, A13W-KP) and KP-insulin (diamonds, KP) in relation to inactive control samples: diluent alone (circles) and an analogue containing a mutation in the Site-1-related surface that impairs receptor binding by ca. 100-fold (Trp$^{43}$-KP-insulin; squares, A3W-KP). Doses were in each case 60 μg per rat.
Figure 15B:
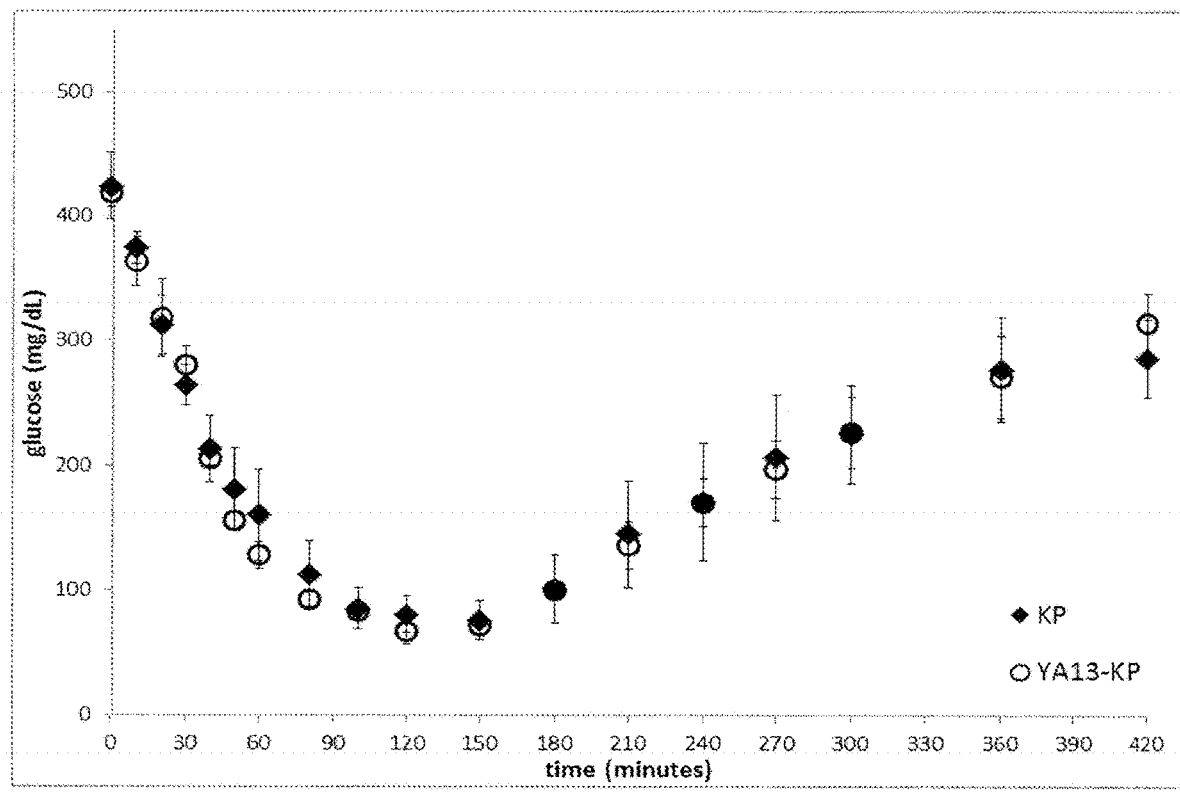
FIG. 15B is a graph showing mean blood glucose levels over time for KP-insulin (filled diamonds) and Tyr$^{413}$-KP-insulin (open circles, YA13-KP). Doses were in each case 60 μg per rat.
Figure 15C:
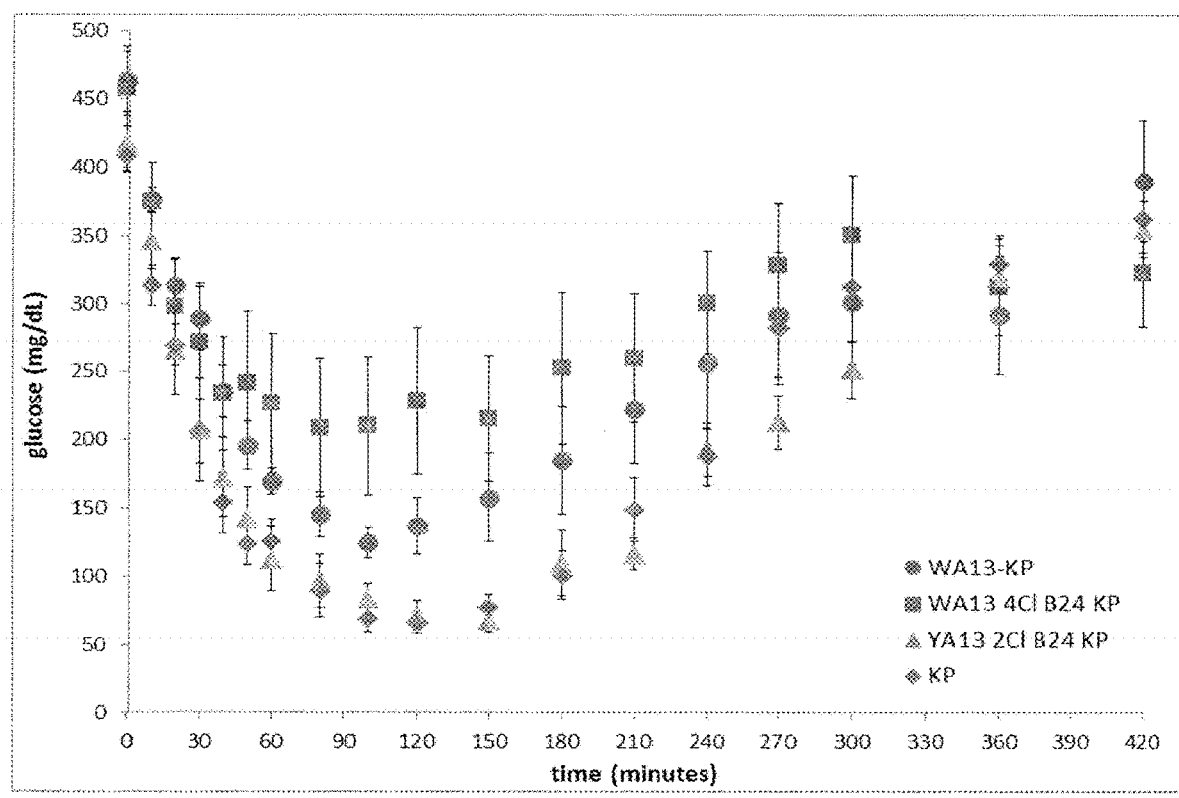
FIG. 15C is a graph showing mean blood glucose levels over time for 4-Cl-Phe$^{B24}$-Trp$^{413}$-KP-insulin (squares, WA13 4Cl B24 KP), Trp$^{413}$-KP-insulin (circles, WA13-KP), 2-Cl-Tyr$^{414}$-KP-insulin (triangles, YA13 2CL B24 KP), and KP-insulin (diamonds); no diluent control was employed. Doses were in each case 60 μg per rat.

We observed that Trp$^{A13}$ (SEQ ID NO: 39) in Site 2 impairs binding of KP-insulin to the IR by ca. twofold (Table 4 and FIG. 14A) whereas the effect of Tyr$^{A13}$ (SEQ ID NO: 42) on binding affinity is negligible (Table 4 and FIG. 14B, top). Thus, comparison of Trp$^{A13}$-KP-insulin to control analogue Tyr$^{A13}$-KP-insulin provided a test of the guiding hypothesis that modest perturbations to biochemical affinity by a Site-2 modification would lead to foreshortened duration of insulin action in vivo; i.e., the long-sought but unmet goal of a "fast-off" pharmacodynamics property. We therefore undertook to investigate the pharmacodynamics properties and relative potencies of these and related insulin analogues in a rat model of diabetes mellitus as described in detail below. These results were obtained as shown in FIGS. 14 and 15. The foreshortening of the pharmacodynamic (PD) properties of Trp$^{A13}$-KP-insulin was further enhanced by co-modification with 4-Cl-Phe$^{B24}$ (FIG. 11C; SEQ ID. NO: 37). Although this modification has negligible effect on the receptor-binding affinity (FIG. 14B, bottom relative to parent TrpA13-KP-insulin in FIG. 14A), synergistic improvement is observed in the extent of foreshortening. Such synergy between modifications at the Site-1-related surface and Site-2-related surface is desirable from the perspective of prandial insulin therapy and the robust and safe operation of closed-loop systems. The shorter the duration of action, the more quickly a closed-loop system can compensate for over-delivery events.

Analogs of KP-insulin containing Trp$^{A13}$ or Tyr$^{A13}$ were prepared by trypsin-catalyzed semi-synthesis. The essential idea was to use trypsin "in reverse" as a synthetic enzyme in an organic co-solvent. This protocol employs (i) a synthetic octapeptide representing residues (N)-GXFYTKPT "KP" substitutions (underlined) and (ii) truncated analog des-octapeptide[B23-B30]-insulin (DOI), Trp$^{A13}$-DOI, or Tyr$^{A13}$-DOI. Because the octapeptide differs from the wild-type B23-B30 sequence (GFFYTPKT), protection of the lysine ε-amino group is not required during trypsin treatment. The protocol was extended to enable co-modification of the A13 site with unnatural amino-acid substitutions at position B24 as contained in the synthetic octapeptide. Wild-type DOI was prepared from human or porcine insulin; the A13 analogues of DOI were generated by trypsin digestion of a 53-residue mini-proinsulin (MPI) precursor modified at the A13 codon as expressed and secreted by yeast strain *Pichia pastoris*. In each case the three native disulfide bridges are retained throughout the procedure.

In brief, des-octapeptide insulin (150 mg) and octapeptide (150 mg) were dissolved in a mixture of dimethylacetamide/1,4-butandiol/0.2 M Tris acetate (pH 8) containing 10 mM calcium acetate and 1 mM ethylene diamine tetra-acetic acid (EDTA) (35:35:30, v/v, 4 ml). The 5-fold molar excess of octapeptide over DOI ensured that the reverse reaction of trypsin (proteolysis) was prevented by substrate saturation. The final pH was adjusted to 7.0 with 0.1 ml of N-methylmorpholine. The solution was cooled to 12° C., and 15 mg of TPCK-trypsin were added and incubated for 2 days at 12° C. An additional 15 mg of trypsin were added after 24 hr. The reaction was then be acidified with 0.1% trifluoroacetic acid and purified by preparative reverse-phase HPLC (C4). The product was verified by mass spectrometry (MALDI-TOF-TOF; Applied Biosystems, Foster City, Calif.). KP-octapeptides containing Phe$^{B24}$, 2-Cl-Phe$^{B24}$, 4-Cl-Phe$^{B24}$, or Cha$^{B24}$ (each ca. 600 mg crude material) were provided by the CCF Peptide Core Facility.

DOI and DOI analogues were generated by trypsin digestion of human insulin, available in bulk quantity from insulin manufacturers. To generate DOI or DOI analogue, the insulin (300 mg) was added to a solution of 0.1 M ammonium bicarbonate (60 ml) containing IM urea. Trypsin (30 mg) was first dissolved in 1.0 ml of distilled deionized water and then added to the protein solution; cleavage proceeds for 48 hours. DOI or DOI analogue was purified from trypsin, unreacted insulin, and any other contaminants by preparative reverse-phase HPLC using a C4 column. Yields of at least 150 mg purified DOI were typically obtained. Analytical reverse-phase HPLC (C18) was used to follow the time course of semi-synthesis and assess the purity of polypeptide reagents and products by analytical HPLC and MALDI-TOF MS (below) for semi-quantitative estimation of products<1%.

Receptor-binding affinities for the Trp$^{A13}$ and Tyr$^{A13}$ derivatives of KP-insulin were determined by an in vivo competitive displacement assay as illustrated in FIGS. 14A and 14B. The protocol for assay of receptor-binding activities was as follows. Microtiter strip plates (Nunc Maxisorb) were incubated overnight at 4° C. with AU5 IgG (100 al/well of 40 mg/ml in phosphate-buffered saline). Binding data were analyzed by a two-site sequential model. Data were corrected for nonspecific binding (amount of radioactivity remaining membrane associated in the presence of 1 μM human insulin. In all assays the percentage of tracer bound in the absence of competing ligand was less than 15% to avoid ligand-depletion artifacts. Dissociation constants ($K_d$) were determined by fitting to a mathematic model as described by Whittaker and Whittaker (2005. *J. Biol. Chem.* 280, 20932-20936); the model employed non-linear regression with the assumption of heterologous competition (Wang, 1995, *FEBS Lett.* 360, 111-114). Results are summarized in Table 4. Whereas Tyr$^{A13}$ does not affect receptor binding of KP-insulin, Trp$^{A13}$ results in a reduction of binding affinity by ca. twofold. Modest changes were also observed with co-substitution of Cha$^{B24}$, 2-Cl-Phe$^{B24}$, or 4-Cl-Phe$^{B24}$ in accordance with previously disclosed studies.

TABLE 4

Properties of Insulin Analogues

| protein | receptor-binding affinity | thermodynamic stability (25° C.) |
|---|---|---|
| wt human insulin | 100% | 3.3(±0.1) kcal/mole |
| KP-insulin | 90-100 | 2.9(±0.1) kcal/mole |
| Trp$^{A13}$-KP-insulin | 50-60 | 2.6(±0.1) kcal/mole |

TABLE 4-continued

Properties of Insulin Analogues

| protein | receptor-binding affinity | thermodynamic stability (25° C.) |
|---|---|---|
| 4-Cl-Phe$^{B24}$-Trp$^{A13}$-KP-ins. | 45-55 | 2.5(±0.1) kcal/mole |
| Tyr$^{A13}$-KP-insulin | 90-110 | 2.8(±0.1) kcal/mole |
| 4-Cl-Phe$^{B24}$-Tyr$^{A13}$-KP-ins. | ND | 2.5(±0.1) kcal/mole |
| Cha$^{B24}$-Trp$^{A13}$-KP-ins. | ND | 2.1(±0.1) kcal/mole |

Circular dichroism (CD) spectra were obtained at 25° C. using an Aviv spectropolarimeter (Weiss et al., *Biochemistry* 39, 15429-15440) as shown in FIG. 12. The CD pattern is in each case consistent with a predominance of alpha-helix; variations are observed that may reflect small perturbations in the stability of secondary structure or may represent superimposed CD bands arising from the additional or modified aromatic side chains. Samples contained ca. 60 µM KP-insulin or analogues in 50 mM potassium phosphate (pH 7.4); samples were diluted to 5 µM for guanidine-induced denaturation studies at 25° C. Representative guanidine titrations are shown in FIG. 13. To extract free energies of unfolding, denaturation transitions were fitted by non-linear least squares to a two-state model as described by Sosnick et al., *Methods Enzymol.* 317, 393-409. Estimates of free energies of unfolding, as obtained from application of this two-state model, are provided in Table 4.

Figure 11:
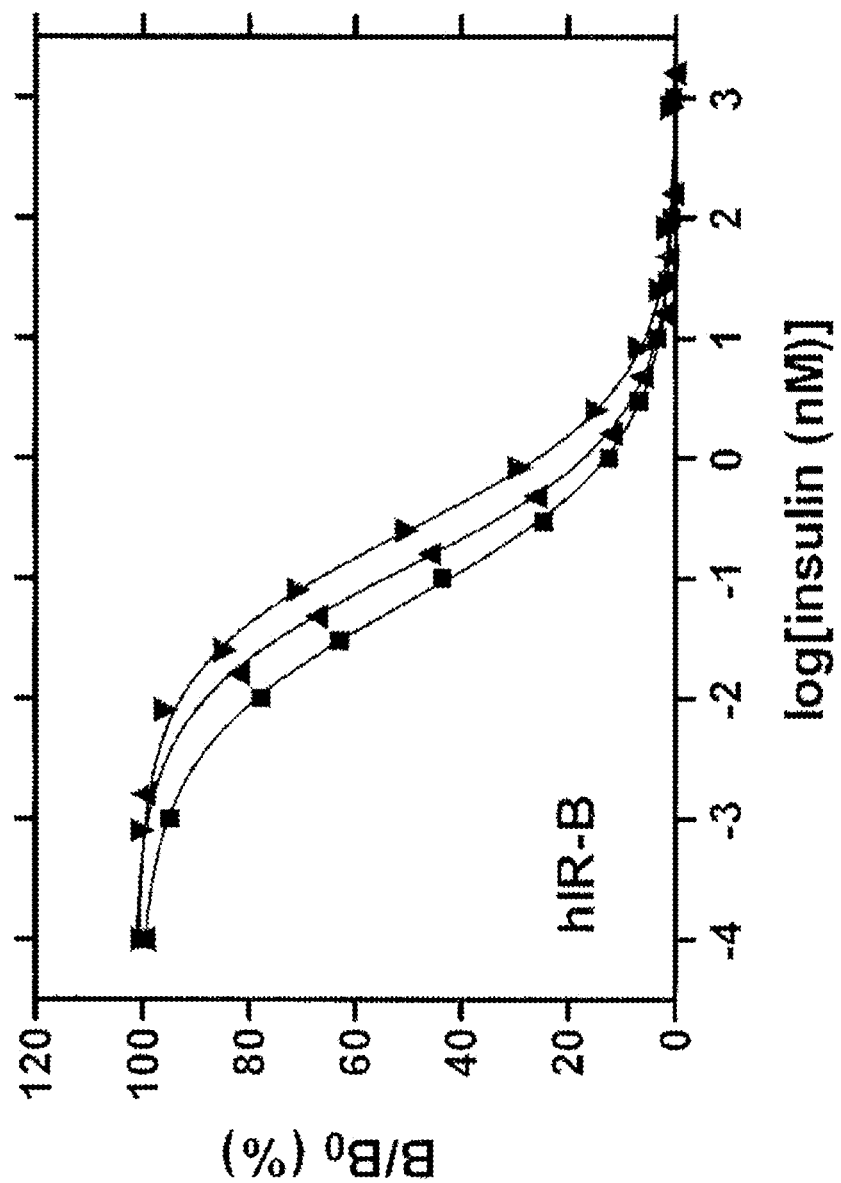
FIG. 11 is a graph showing the results of receptor-binding studies of insulin analogues. Relative activities for the B isoform of the insulin receptor (IR-B) are determined by competitive binding assay in which receptor-bound $^{125}$I-labeled human insulin is displaced by increasing concentrations of human insulin (●) or its analogues: KP-insulin (▲) and $Cha^{B24}$-KP-insulin (▼).

To evaluate the biological activity and potency of the analogues in an animal model, male Sprague-Dawley rats (mean body mass ~300 grams) were rendered diabetic by treatment with streptozotocin (STZ). Protein solutions containing KP-insulin (insulin Lispro, the active component of Humalog®), wild-type human insulin, and/or a two-chain or single-chain insulin of the present invention. A control was provided by injection of protein-free Lilly diluent (obtained from Eli Lilly and Co.) composed of 16 mg glycerin, 1.6 mg meta-cresol, 0.65 mg phenol, and 3.8 mg sodium phosphate pH 7.4. The activity of the insulin analogues was evaluated in relation to that of Humalog® (U-100 strength taken from an unexpired commercial vial). 20 or 60 micrograms of each of these formulations were injected subcutaneously, and resulting changes in blood glucose concentration were monitored by serial measurements using a clinical glucometer (Hypoguard Advance Micro-Draw meter). Rats were injected subcutaneously at time t=0 in groups of five (N=4-6). Blood was obtained from the clipped tip of the tail at time 0 and every 10 minutes up to 360 min. Representative two-chain analogues of the present invention, Trp$^{A14}$-KP-insulin of the present invention were found, under conditions of formulation similar to that of Humalog®, to retain a substantial proportion of the biological activity of insulin and with duration of action foreshortend with respect to Humalog®. Representative pharmacodynamic data are shown in FIG. 11. Various analogues according to the claimed invention are provided in Table 5.

TABLE 5

| Analogue | Sequences |
|---|---|
| GluA13 LysB28 ProB29 | A-chain GIVEQCCTSICSEYQLENYCN (SEQ ID NO: 35)<br>B-chain FVNQHLCGSHLVEALYLVCGERGFFYTKPT (SEQ ID NO: 36) |
| GluA13 para-chloro-PheB24 LysB28 ProB29 | A-chain GIVEQCCTSICSEYQLENYCN (SEQ ID NO: 35)<br>B-chain FVNQHLCGSHLVEALYLVCGERGXFYTKPT,<br>X = para-chloro-phenylalanine (SEQ ID NO: 37) |
| HisA13 LysB28 ProB29 | A-chain GIVEQCCTSICSHYQLENYCN (SEQ ID NO: 38)<br>B-chain FVNQHLCGSHLVEALYLVCGERGFFYTKPT (SEQ ID NO: 36) |
| HisA13 para-chloro-PheB24 LysB28 ProB29 | A-chain GIVEQCCTSICSHYQLENYCN (SEQ ID NO: 38)<br>B-chain FVNQHLCGSHLVEALYLVCGERGXFYTKPT,<br>X = para-chloro-phenylalanine (SEQ ID NO: 37) |
| TrpA13 LysB28 ProB29 | A-chain GIVEQCCTSICSWYQLENYCN (SEQ ID NO: 39)<br>B-chain FVNQHLCGSHLVEALYLVCGERGFFYTKPT (SEQ ID NO: 36) |
| TrpA13 para-chloro-PheB24 LysB28 ProB29 | A-chain GIVEQCCTSICSWYQLENYCN (SEQ ID NO: 39)<br>B-chain FVNQHLCGSHLVEALYLVCGERGXFYTKPT,<br>X = para-chloro-phenylalanine (SEQ ID NO: 37) |
| TrpA13 AspB10 ortho-fluoro-PheB24 LysB28 ProB29 | A-chain GIVEQCCTSICSWYQLENYCN (SEQ ID NO: 39)<br>B-chain FVNQHLCGSDLVEALYLVCGERGXFYTKPT,<br>X = ortho-fluoro-phenylalanine (SEQ ID NO: 40) |
| GlnA8 TrpA13 LysB28 ProB29 | A-chain GIVEQCCQSICSWYQLENYCN (SEQ ID NO: 41)<br>B-chain FVNQHLCGSHLVEALYLVCGERGFFYTKPT (SEQ ID NO: 36) |
| GlnA8 TrpA13 para-chloro-PheB24 LysB28 ProB29 | A-chain GIVEQCCQSICSWYQLENYCN (SEQ ID NO: 41)<br>B-chain FVNQHLCGSHLVEALYLVCGERGXFYTKPT,<br>X = para-chloro-phenylalanine (SEQ ID NO: 37) |
| TyrA13 LysB28 ProB29 | A-chain GIVEQCCTSICSYYQLENYCN (SEQ ID NO: 42)<br>B-chain FVNQHLCGSHLVEALYLVCGERGFFYTKPT (SEQ ID NO: 36) |

TABLE 5-continued

| Analogue | Sequences |
|---|---|
| TyrA13 para-chloro-PheB24 LysB28 ProB29 | A-chain GIVEQCCTSICSYYQLENYCN (SEQ ID NO: 42)<br>B-chain FVNQHLCGSHLVEALYLVCGERGXFYTKPT,<br>X = para-chloro-phenylalanine (SEQ ID NO: 37) |
| TyrA13 ortho-chloro-PheB24 LysB28 ProB29 | A-chain GIVEQCCTSICSYYQLENYCN (SEQ ID NO: 42)<br>B-chain FVNQHLCGSHLVEALYLVCGERGXFYTKPT,<br>X = ortho-chloro-phenylalanine (SEQ ID NO: 43) |
| TyrA13 cyclohexylalanine-B24 LysB28 ProB29 | A-chain GIVEQCCTSICSYYQLENYCN (SEQ ID NO: 42)<br>B-chain FVNQHLCGSHLVEALYLVCGERGXFYTKPT,<br>X = cyclohexanylalanine (SEQ ID NO: 44) |
| AlaA13 LysB28 ProB29 | A-chain GIVEQCCTSICSAYQLENYCN (SEQ ID NO: 45)<br>B-chain FVNQHLCGSHLVEALYLVCGERGFFYTKPT<br>(SEQ ID NO: 36) |
| GluB17 LysB28 ProB29 | A-chain GIVEQCCTSICSLYQLENYCN (SEQ ID NO: 2)<br>B-chain FVNQHLCGSHLVEALYEVCGERGFFYTKPT<br>(SEQ ID NO: 46) |
| PheA13 LysB28 ProB29 | A-chain GIVEQCCTSICSFYQLENYCN (SEQ ID NO: 47)<br>B-chain FVNQHLCGSHLVEALYLVCGERGFFYTKPT<br>(SEQ ID NO: 36) |
| PheB17 LysB28 ProB29 | A-chain GIVEQCCTSICSLYQLENYCN (SEQ ID NO: 2)<br>B-chain FVNQHLCGSHLVEALYFVCGERGFFYTKPT<br>(SEQ ID NO: 36) |
| GlnA8 TrpA13 GlnB13 para-chloro-PheB24 LysB28 ProB29 | A-chain GIVEQCCQSICSWYQLENYCN (SEQ ID NO: 48)<br>B-chain FVNQHLCGSHLVQALYLVCGERGXFYTKPT,<br>X = para-chloro-phenylalanine (SEQ ID NO: 49) |

Receptor binding by the various analogues of the claimed invention was analyzed as follows. In vitro activity assays employed epitope-tagged holoreceptor of either human insulin receptor isoform B (hIR-B) and/or isoform A (hIR-A) and/or the homologous human type 1 insulin-like growth factor receptor (hIGFR) immobilized on 96 well plates. Relative activity is defined as the ratio of specific dissociation constants as determined by competitive displacement of bound $^{125}$I-TyrA14 human insulin (in the case of IR) or $^{125}$I-Tyr31 human IGF-I (in the case of IGFR). Dissociation constants ($K_d$) were determined by fitting to a mathematic model as described by Whittaker and Whittaker (2005. *J. Biol. Chem.* 280, 20932-20936); the model employed non-linear regression with the assumption of heterologous competition (Wang, 1995, *FEBS Lett.* 360, 111-114). Results listed in Table 6 (Assay: hIR-A, hIR-B) are consistent with native in vivo potency. Corresponding studies of cross-binding to the mitogenic IGF receptor (Assay: hIGFR) demonstrated affinities similar to native insulin.

TABLE 6

| | In Vitro Data | | | | | | |
|---|---|---|---|---|---|---|---|
| | hIR-A | | hIR-B | | IGFR | | ΔGU |
| Analogue | Kd | error | Kd | error | Kd | error | kcal/mol |
| GluA13 LysB28 ProB29 | 0.14 | 0.02 | 0.23 | 0.03 | 9.03 | 1.48 | ND |
| GluA13 para-chloro-PheB24 LysB28 ProB29 | 0.23 | 0.03 | 0.31 | 0.04 | 27.8 | 5.30 | ND |
| HisA13 LysB28 ProB29 | 0.04 | 0.01 | 0.07 | 0.01 | 2.87 | 0.45 | ND |
| TrpA13 LysB28 ProB29 | ND | | 0.11 | 0.02 | ND | | 2.6 ± 0.1 |
| TrpA13 para-chloro-PheB24 LysB28 ProB29 | ND | | 0.07 | 0.01 | ND | | 2.5 ± 0.1 |
| GlnA8 TrpA13 LysB28 ProB29 | 0.03 | 0.01 | 0.07 | 0.01 | 4.64 | 0.71 | ND |
| GlnA8 TrpA13 para-chloro-PheB24 LysB28 ProB29 | ND | | 0.04 | 0.01 | ND | | ND |
| TryA13 LysB28 ProB29 | ND | | 15.4 | 2.7 | ND | | 2.8 ± 0.1 |
| TyrA13 para-chloro-PheB24 LysB28 ProB29 | ND | | 0.03 | 0.01 | ND | | 2.5 ± 0.1 |
| TyrA13 ortho-chloro-PheB24 LysB28 ProB29 | ND | | 0.06 | 0.01 | ND | | 2.1 + 0.1 |
| TyrA13 cyclohexanylalanine-B24 LysB28 ProB29 | ND | | 0.22 | 0.03 | ND | | ND |

TABLE 6-continued

|  | In Vitro Data | | | | | | |
|---|---|---|---|---|---|---|---|
|  | hIR-A | | hIR-B | | IGFR | | ΔGU |
| Analogue | Kd | error | Kd | error | Kd | error | kcal/mol |
| AlaA13 LysB28 ProB29 | 0.05 | 0.01 | 0.17 | 0.03 | 9.7 | 1.6 | ND |
| GluB17 LysB28 ProB29 | 0.06 | 0.01 | 0.11 | 0.02 | 2.64 | 0.42 | ND |
| PheA13 LysB28 ProB29 | 0.05 | 0.01 | 0.07 | 0.01 | 3.12 | 0.51 | ND |
| PheB17 LysB28 ProB29 | 0.07 | 0.01 | 0.07 | 0.01 | 3.03 | 0.48 | ND |

ND: Not done

To evaluate the biological activity (potency and duration of action) of the analogues in an animal model, male Sprague-Dawley rats were rendered diabetic by treatment with streptozotocin (STZ). The activity of the insulin analogues was evaluated in relation to that of Humalog® (U-100 strength taken from an unexpired commercial vial). 5, 20 or 60 micrograms of each of the analogue formulations were injected subcutaneously and resulting changes in blood glucose concentration were monitored by serial measurements using a clinical glucometer (Hypoguard Advance Micro-Draw meter). Rats were injected subcutaneously at time t=0 in groups of five (N=4-6). Blood was obtained from the clipped tip of the tail at time 0 and every 10 minutes up to 360 min to determine the drop in blood glucose as Δ/min and Δ/hr over the 1st hour. Representative analogues of the present invention were found, under conditions of formulation similar to that of Humalog®, to retain a substantial proportion of the biological activity of insulin and with duration of action foreshortened with respect to Humalog® as shown in Table 7

TABLE 7

|  | Small Animal Activity (rat) | |
|---|---|---|
| Analogues (substitutions as indicated, all other positions are wild-type human insulin) | Δ Blood Glucose (60 ug dose) | error |
| GluA13 LysB28 ProB29 | −303.34 Δ/hr | 8.86 |
|  | −5.16 Δ/min | 0.15 |
| GluA13 para-chloro-PheB24 LysB28 ProB29 | −310.54 Δ/hr | 8.5 |
|  | −5.18 Δ/min | 0.14 |
| TrpA13 LysB28 ProB29 | −256.03* Δ/hr | 17.91 |
|  | −4.26* Δ/min | 0.3 |
| TrpA13 para-chloro-PheB24 LysB28 ProB29 | −218.89 Δ/hr | 35.61 |
|  | −3.65 Δ/min | 0.61 |
| GlnA8 TrpA13 LysB28 ProB29 | −206.36 Δ/hr | 29.8 |
|  | −3.44 Δ/min | 0.5 |
| GlnA8 TrpA13 para-chloro-PheB24 LysB28 ProB29 | −287.96 Δ/hr | 24.87 |
|  | −4.80 Δ/min | 0.41 |
| TryA13 LysB28 ProB29 | −300.38 Δ/hr | 28.53 |
|  | −5.01 Δ/min | 0.48 |
| TyrA13 para-chloro-PheB24 LysB28 ProB29 | −239.66 Δ/hr | 20.21 |
|  | −3.99 Δ/min | 0.34 |
| TyrA13 ortho-chloro-PheB24 LysB28 ProB29 | −303.75 Δ/hr | 23.82 |
|  | −5.06 Δ/min | 0.4 |
| TyrA13 cyclohexanylalanine-B24 LysB28 ProB29 | −263.84 Δ/hr | 5.92 |
|  | −4.40 Δ/min | 0.1 |
| AlaA13 LysB28 ProB29 | −272.06 Δ/hr | 19.53 |
|  | −4.93 Δ/min | 0.33 |
| GluB17 LysB28 ProB29 | −296.83 Δ/hr | 14.87 |
|  | −4.95 Δ/min | 0.25 |
| PheA13 LysB28 ProB29 | −300.26 Δ/hr | 33 |
|  | −5.00 Δ/min | 0.55 |
| PheB17 LysB28 ProB29 | −259.14 Δ/hr | 6.22 |
|  | −4.32 Δ/min | 0.1 |

Non-diabetic anesthetized Sinclair pigs whose pancreatic β- and α-cell function has been suppressed by IV octreotide acetate were used to assess large animal in vivo effects and pharmacodynamics. Approximately 30 minutes after initiating octreotide acetate infusion, baseline euglycemia was established with 10% dextrose infusion. Once in a euglycemic state, 0.1-0.2 U/kg insulin was administered intravenously through a vascular access port at. In order to quantify peripheral insulin-mediated glucose uptake, blood glucose was measured every 5 minutes while a variable rate glucose infusion maintained a blood glucose level of approximately 85 mg/dL. This glucose infusion was maintained until the endogenous blood glucose returned to baseline (pre-insulin infusion) levels. Pharmacodynamic (PD) effects were measured as time to half-maximal effect ($T_{1/2}$ early), time to half-maximal effect ($T_{1/2}$ late), and time to maximal effect ($T_{max}$). For each of these analyses, the 20-minute moving mean curve fit was employed. Representative analogues of the present invention demonstrated large animal biological effects comparable to native insulin as shown in Table 8.

TABLE 8

| Analogues (substitutions as indicated, all other positions are wild-type human insulin) | Large Animal Activity (pig) |
|---|---|
|  | 0.1-0.2 U/kg dose |
| TrpA13 para-chloro-PheB24 LysB28 ProB29 | 10.0 min T½ early |
|  | 56.0 min T½ late |
| TyrA13 para-chloro-PheB24 LysB28 ProB29 | 12.0 min T½ early |
|  | 54.0 min T½ late |
| TyrA13 cyclohexanylalanine-B24 LysB28 ProB29 | 8.0 min T½ early |
|  | 58.0 min T½ late |

A method for treating a patient with diabetes mellitus comprises administering an insulin analogue as described herein. It is another aspect of the present invention that insulin analogues may be prepared either in yeast (*Pichia pastoris*) or subject to total chemical synthesis by native fragment ligation. We further envision the analogues of the present invention providing a method for the treatment of diabetes mellitus or the metabolic syndrome. The route of delivery of the insulin analogue is by subcutaneous injection through the use of a syringe or pen device.

An insulin analogue of the present invention may also contain other modifications, such as a halogen atom at positions B24, B25, or B26 as described more fully in U.S. Pat. No. 8,921,313, the disclosure of which is incorporated by reference herein. An insulin analogue of the present invention may also contain a foreshortened B-chain due to deletion of residues B1-B3.

A pharmaceutical composition may comprise such insulin analogues and which may optionally include zinc. Zinc ions may be included at varying zinc ion:protein ratios, ranging from 2.2 zinc atoms per insulin analogue hexamer to 3 zinc atoms per insulin analogue hexamer. The pH of the formulation is in the range pH 6.8-8.0. In such a formulation, the concentration of the insulin analogue would typically be between about 0.6-5.0 mM; concentrations up to 5 mM may be used in vial or pen; the more concentrated formulations (U-200 or higher) may be of particular benefit in patients with marked insulin resistance. Excipients may include glycerol, glycine, arginine, Tris, other buffers and salts, and anti-microbial preservatives such as phenol and meta-cresol; the latter preservatives are known to enhance the stability of the insulin hexamer. Single-chain insulin analogues may be formulated in the presence of zinc ions or in their absence. Such a pharmaceutical composition as described above may be used to treat a patient having diabetes mellitus or other medical condition by administering a physiologically effective amount of the composition to the patient.

In a further example of the present invention, an insulin analogue combines a modification in the Site-1-binding surface of insulin (that is, replacement of Phe by cyclohexanylalanine at B24) with a modification in its Site-2-binding surface (substitution of Leu$^{413}$ by Trp). A third substitution (Thr$^{48}$→Glu) was included to mitigate the decrease in protein stability caused by the first two substitutions. As provided more fully below, the Site-1-related and Site-2-related substitutions to reduce the residence time of the hormone-receptor complex, as supported by the analogue's lower affinities for the A- and B isoforms of the insulin receptor (by five- and 13-fold, respectively). It is notable that the ratio of receptor isoform binding is skewed to IR-B receptor and away from the mitogenic IR-A receptor. The data provided below demonstrate that the insulin analogue with a relative preference for IR-B, exhibits a change in relative organ selectivity. A relative decrease in hepatic insulin signaling could be of clinical interests in patients with the fatty liver syndrome, for example.

Normal male Sprague-Dawley rats (~320-350 g) with chronically implanted catheters underwent a hyperinsulinemic-euglycemic clamp with either lispro insulin (KP; SEQ ID NOS: 2 and 36) or EA$^8$,WA$^{13}$,B$^{24}$CHA analog (CHA; SEQ ID NOS: 50 and 51). Pilot experiments helped to establish insulin doses to provide equivalent glucose infusion (GINF) during the clamp. A primed infusion of glucose was administered followed by a continuous dosage. To compare equipotent doses, a primed infusion for KP insulin was provided at 120 pmol/kg with a continuous infusion provided at 24 pmol/kg-min, and for CHA the primed infusion was provided at 200 pmol/kg and the continuous infusion was provided at 40 pmol/kg-min. A bolus of 2-deoxyglucose (DOC) was given during the final 30' to measure tissue specific glucose uptake.

Glucose appearance and disposal was determined by calculating the difference between glucose infused and glucose present in the plasma as determined by glucometer. Plasma levels of plasma nonesterified fatty acids (NEFA) are determined using a colorimeteric assay such as the assay kit available from Fujifilm Wako Diagnostics (Mountain View, Calif.). Phosphorylation relative to basal level was measured using Western blot analysis of samples harvested from liver, gastrocnemius and epididymal white adipose tissue (eWAT), and immunoblotted using anti-phosphotyrosine antibody (Cell Signaling Technologies, Inc., Danvers, Mass., Phospho-IGF-I Receptor β (Tyr1135) Rabbit monoclonal antibody #3918). Similarly Akt phosphorylation was similarly tested using Cell Signaling Technology, Inc. (Danvers, Mass.) antibody No. 9271 as primary antibody and horse radish peroxidase (HRP)-linked Anti-rabbit IgG antibody No. 7074 (Cell Signaling Technology, Inc., Danvers, Mass.).

Figure 16C:
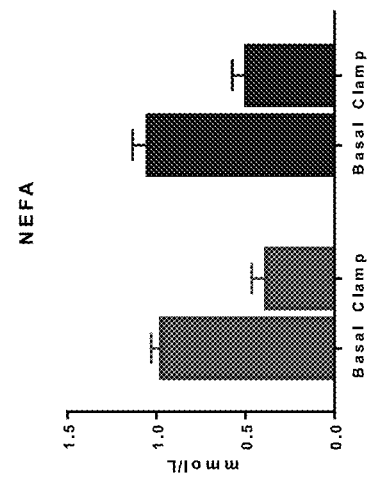
FIG. 16C is a bar graph showing plasma nonesterified fatty acids (NEFA) concentration for lispro insulin (KP) or EA$^8$WA$^{13}$B$^{24}$CHA analogue (CHA).
Figure 16B:
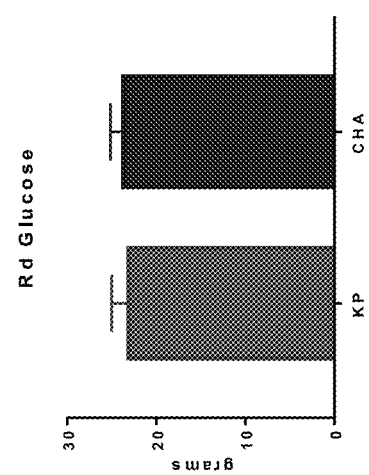
FIG. 16B is a bar graph showing insulin stimulated whole body glucose disposal (Rd) for lispro insulin (KP) or EA$^8$WA$^{13}$B$^{24}$CHA analogue (CHA) (22.9±1.7 vs. 21.1±1.4 mg·kg$^{-1}$·min$^{-1}$) during hyperinsulinemic-euglycemic clamp.
Figure 16A:
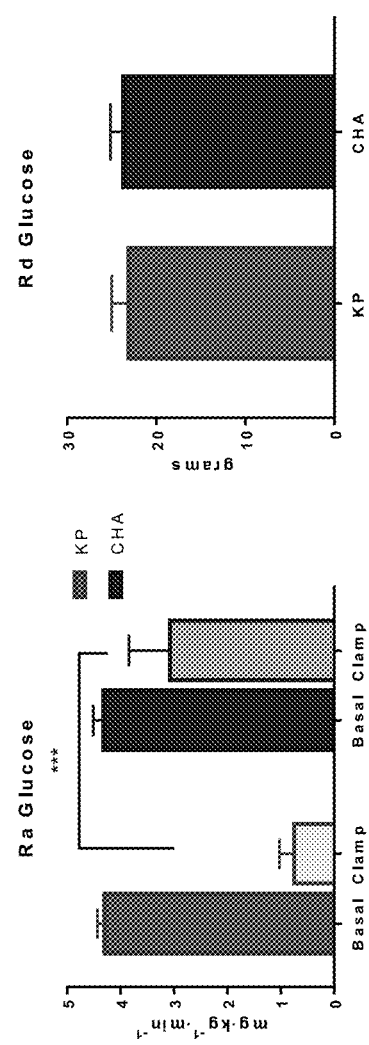
FIG. 16A is bar graph showing basal and clamped plasma glucose concentration (115±2.8 (n=9) vs. 111.1±5.1 mg/dL (n=8) for lispro insulin (KP) or EA$^8$WA$^{13}$B$^{24}$CHA analogue (CHA), respectively.

During the clamp, plasma glucose concentration (115±2.8 (n=9) vs. 111.1±5.1 mg/dL (n=8) for KP and CHA, respectively) and GINF (22.9±1.7 vs. 21.1±1.4 mg·kg$^{-1}$·min$^{-1}$) were both matched. There was no statistical difference in the basal rate of glucose appearance (Ra, FIG. 16A). However, under hyperinsulinemic conditions, KP suppressed endogenous glucose production (EGP) more than CHA (81.6±5.7 vs. 28.2±16.7%, p=0.001). In contrast, both KP and CHA increased insulin stimulated whole body glucose disposal (Rd) and suppressed plasma nonesterified fatty acids (NEFA) to a similar degree (FIGS. 16B and 16C). This discordance suggests that CHA was more active at peripheral sites (skeletal muscle and adipose tissue) and less active at the liver.

Figure 16F:
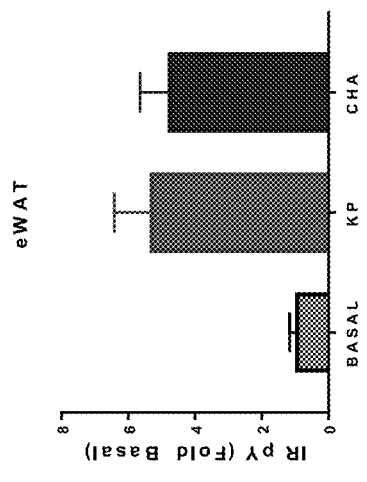
FIG. 16F is a bar graph showing insulin receptor tyrosine phosphorylation levels at tyrosine 1135 (IR pY) in epididymal white adipose tissue (eWAT).
Figure 16E:
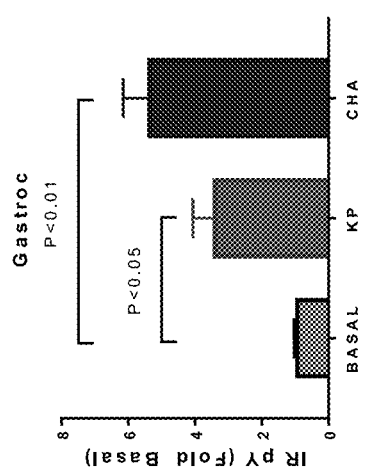
FIG. 16E is a bar graph showing insulin receptor tyrosine phosphorylation levels at tyrosine 1135 (IR pY) in gastrocnemius.
Figure 16D:
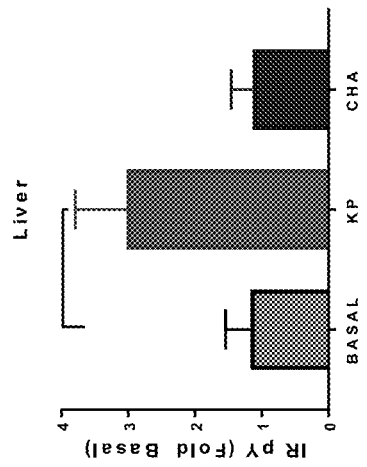
FIG. 16D is a bar graph showing insulin receptor tyrosine phosphorylation levels at tyrosine 1135 (IR pY) in liver.

Consistent with these differences in glucose metabolism, CHA had less activation of hepatic insulin signaling with a decrease in insulin receptor tyrosine phosphorylation at tyrosine 1152 (IRKpY, FIG. 16D) while activating IRKpY to a similar degree in gastrocnemius muscle and epididymal white adipose tissue (eWAT, FIGS. 16E and 16F). A similar pattern was seen at Akt phosphorylation. (Data not shown.) Finally, both KP and CHA increased 2-deoxyglucose uptake in gastrocnemius (18.7±1.6 vs 18.6±2.5 mg glucose·kg tissue$^{-1}$·min$^{-1}$) and eWAT (0.9±0.1 vs. 0.72±0.1 mg glucose·kg tissue$^{-1}$·min$^{-1}$).

Previous studies have shown lower doses of insulin suppress EGP while higher doses are needed to maximally stimulate whole body glucose metabolism. Thus, suppression of EGP (largely reflecting liver insulin action) is thought to be more sensitive to insulin. In contrast, CHA uniquely demonstrates less action at the liver than KP while stimulating insulin action at skeletal muscle and adipose tissue to a similar degree as KP. These data suggest that CHA has some tissue selectivity: it preferentially activates muscle and white adipose tissue insulin signaling compared to liver insulin signaling.

A method for treating a patient comprises administering an insulin analogue containing a Cha-substituted Phe or additional amino-acid substitutions in the A or B chain as known in the art or described herein. In one example, the Cha-substituted insulin analogue is an insulin analogue containing Cha at position B24 in the context of KP-insulin, that is, Lys$^{B28}$ and Pro$^{B29}$ substitutions. In another example, Cha$^{B24}$ is substituted within human insulin analogues containing non-standard modifications at position B29 (Ornithine or Norleucine). It is yet another aspect of the present invention that use of non-standard amino-acid substitutions enables a rapid and efficient method of preparation of insulin analogues by trypsin-mediated semi-synthesis using unprotected octapeptides.

In still another example, the insulin analogue is administered by an external or implantable insulin pump. An insulin analogue of the present invention may also contain other modifications, such as a tether between the C-terminus of the B-chain and the N-terminus of the A-chain as described more fully in U.S. Pat. No. 8,192,957, the disclosure of which is incorporated by reference herein.

A pharmaceutical composition may comprise such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin® (Eli Lilly and Co.), Humalog® (Eli Lilly and Co.), Novalin® (Novo-Nordisk), and Novalog® (Novo-Nordisk) and other rapid-acting insulin formulations currently approved for human use, (b) "NPH" formulations of the above and other insulin analogues, and (c) mixtures of such formulations.

Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

A nucleic acid comprising a sequence that encodes a polypeptide encoding an insulin analogue containing a sequence encoding at least a B-chain of insulin with a Cyclohexanylalanine at position B24 is also envisioned. This can be accomplished through the introduction of a stop codon (such as the amber codon, TAG) at position B24 in conjunction with a suppressor tRNA (an amber suppressor when an amber codon is used) and a corresponding tRNA synthetase, which incorporates a non-standard amino acid into a polypeptide in response to the stop codon, as previously described (Furter, 1998, *Protein Sci.* 7:419-426; Xie et al., 2005, *Methods*. 36: 227-238). The particular sequence may depend on the preferred codon usage of a species in which the nucleic-acid sequence will be introduced. The nucleic acid may also encode other modifications of wild-type insulin. The nucleic-acid sequence may encode a modified A- or B-chain sequence containing an unrelated substitution or extension elsewhere in the polypeptide or modified proinsulin analogues. For example, an A-chain containing a Glu$^{48}$ substitution may be utilized. The nucleic acid may also be a portion of an expression vector, and that vector may be inserted into a host cell such as a prokaryotic host cell like an *E. coli* cell line, or a eukaryotic cell line such as *S. cereviciae* or *Pischia pastoris* strain or cell line.

For example, it is envisioned that synthetic genes may be synthesized to direct the expression of a B-chain polypeptide in yeast *Piscia pastoris* and other microorganisms. The nucleotide sequence of a B-chain polypeptide utilizing a stop codon at position B24 for the purpose of incorporating a Cyclohexanylalanine at that position may be either of the following or variants thereof:

(a) with Human Codon Preferences:

```
                                          (SEQ ID NO: 15)
TTTGTGAACCAACACCTGTGCGGCTCACACCTGGTGGAAGCTCTCTA

CCTAGTGTGCGGGAACGAGGCTAGTTCTACACACCCAAGACC
```

(b) with *Pichia* Codon Preferences:

```
                                          (SEQ ID NO: 16)
TTTGTTAACCAACATTTGTGTGGTTCTCATTTGGTTGAAGCTTTGTA

CTTGGTTTGTGGTGAAAGAGGTTAGTTTTACACTCCAAAGACT
```

Similarly, a full length pro-insulin cDNA having human codon preferences and utilizing a stop codon at position B24 for the purpose of incorporating Cyclohexanylalanine at that position may have the sequence of SEQ. ID NO. 17.

```
                                          (SEQ ID NO: 17)
TTTGTGAACC AACACCTGTG CGGCTCACAC CTGGTGGAAG

CTCTCTACCT AGTGTGCGGG AACGAGGCT AGTTCTACAC
```

```
ACCCAAGACC CGCCGGGAGG CAGAGGACCT GCAGGTGGGG

CAGGTGGAGC TGGGCGGCGG CCCTGGTGCA GGCAGCCTGC

AGCCCTTGGC CCTGGAGGGG TCCCTGCAGA AGCGTGGCAT

TGTGGAACAA TGCTGTACCA GCATCTGCTC CCTCTACCAG

CTGGAGAACT ACTGCAACTA G
```

Likewise, a full-length human pro-insulin cDNA utilizing a stop codon at position B24 for the purpose of incorporating a Cyclohexanylalanine at that position and having codons preferred by *P. pastoris* may have the sequence of SEQ ID NO: 18.

```
                                          (SEQ ID NO: 18)
TTTGTTAACC AACATTTGTG TGGTTCTCAT TTGGTTGAAG

CTTTGTACTT GGTTTGTGGT GAAAGAGGTT AGTTTTACAC

TCCAAAGACT AGAAGAGAAG CTGAAGATTT GCAAGTTGGT

CAAGTTGAAT TGGGTGGTGG TCCAGGTGCT GGTTCTTTGC

AACCATTGGC TTTGGAAGGT TCTTTGCAAA AGAGAGGTAT

TGTTGAACAA TGTTGTACTT CTATTTGTTC TTTGTACCAA

TTGGAAAACT ACTGTAACTA A
```

Other variants of these sequences, encoding the same polypeptide sequence, are possible, given the synonyms in the genetic code.

Based upon the foregoing disclosure, it should now be apparent that insulin analogues provided will carry out the objects set forth hereinabove. Namely, these insulin analogues exhibit target organ specificity while maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Furter, R., 1998. Expansion of the genetic code: Site-directed p-fluoro-phenylalanine incorporation in *Escherichia coli. Protein Sci.* 7:419-426.

Glendorf, T., Knudsen, L., Stidsen, C. E., Hansen, B. F., Hegelund, A. C., Sørensen, A. R., Nishimura, E., & Kjeldsen, T. 2012. Systematic evaluation of the metabolic to mitogenic potency ratio for B10-substituted insulin analogues. *PLoS One* 7(2), e29198.

Hohsaka, T., & Sisido, M. 2012. Incorporation of non-natural amino acids into proteins. *Curr. Opin. Chem. Biol.* 6, 809-15.

Hua, Q. X., Nakagawa, S. H., Jia, W., Huang, K., Phillips, N. B., Hu, S. & Weiss, M. A. (2008) Design of an active ultrastable single-chain insulin analog: synthesis, structure, and therapeutic implications. *J. Biol. Chem.* 283, 14703-14716.

Kristensen, C., Andersen, A. S., Hach, M., Wiberg, F. C., Schäffer, L., & Kjeldsen, T. 1995. A single-chain insulin-like growth factor I/insulin hybrid binds with high affinity to the insulin receptor. *Biochem. J.* 305, 981-6.

Lee, H. C., Kim, S. J., Kim, K. S., Shin, H. C., & Yoon, J. W. 2000. Remission in models of type 1 diabetes by gene therapy using a single-chain insulin analogue. *Nature* 408, 483-8. Retraction in: Lee H C, Kim K S, Shin H C. 2009. *Nature* 458, 600.

Merrifield, R. B., Vizioli, L. D., and Boman, H. G. 1982. Synthesis of the antibacterial peptide cecropin A (1-33). Biochemistry 21: 5020-5031.

Mirmira, R. G., and Tager, H. S. 1989. Role of the phenylalanine B24 side chain in directing insulin interaction with its receptor: Importance of main chain conformation. J. Biol. Chem. 264: 6349-6354.

Phillips, N. B., Whittaker, J., Ismail-Beigi, F., & Weiss, M. A. (2012) Insulin fibrillation and protein design: topological resistance of single-chain analogues to thermal degradation with application to a pump reservoir. *J. Diabetes Sci. Technol.* 6, 277-288.

Sciacca, L., Cassarino, M. F., Genua, M., Pandini, G., Le Moli, R., Squatrito, S., & Vigneri, R. 2010. Insulin analogues differently activate insulin receptor isoforms and post-receptor signalling. *Diabetologia* 53, 1743-53.

Sosnick, T. R., Fang, X., and Shelton, V. M. 2000. Application of circular dichroism to study RNA folding transitions. *Methods Enzymol.* 317: 393-409.

Wang, Z. X. 1995. An exact mathematical expression for describing competitive biding of two different ligands to a protein molecule *FEBS Lett.* 360: 111-114.

Weiss, M. A., Hua, Q. X., Jia, W., Chu, Y. C., Wang, R. Y., and Katsoyannis, P. G. 2000. Hierarchical protein "undesign": insulin's intrachain disulfide bridge tethers a recognition α-helix. Biochemistry 39: 15429-15440.

Whittaker, J., and Whittaker, L. 2005. Characterization of the functional insulin binding epitopes of the full length insulin receptor. J. Biol. Chem. 280: 20932-20936.

Xie, J. and Schultz, P. G. 2005. An expanding genetic code. Methods. 36: 227-238.

Sequences

```
(human proinsulin)
                                   SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn (human A chain)
                                   SEQ ID NO: 2
Gly-Ile-Val-Glu-Gln-Cys-Cys-Thr-Ser-Ile-Cys-Ser- Leu-Tyr-Gln-Leu-Glu-Asn-Tyr-Cys-Asn (human B chain)
                                   SEQ ID NO: 3
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr (B10, Cha B24, B28, B29)
                                   SEQ ID NO: 4
Phe-Val-Asn-Gln-His-Leu-Cys-Gly-Ser-Xaa4-Leu- Val-Glu-Ala-Leu-Tyr-Leu-Val-Cys-Gly-Glu-Arg- Gly-Xaa1-Phe-Tyr-Thr-Xaa2-Xaa3-Thr

[Xaa1 is Cha; Xaa2 is Asp, Pro, Lys, or Arg;
Xaa3 is Lys, Pro, or Ala; and Xaa4 is His or Asp]

Substitution of a Cha at position B24 may
optionally be combined with non-standard
substitutions at position B29 as provided in
SEQ. ID. NO 5.

(B10, Cha B24, B29)
                                   SEQ ID NO: 5
Phe-Val-Asn-Gln-His-Leu-Cys-Gly-Ser-Xaa3-Leu-Val-

Glu-Ala-Leu-Tyr-Leu-Val-Cys-Gly-Glu-Arg-Gly-Xaa1-

Phe-Tyr-Thr-Pro-Xaa2-Thr

[Xaa1 is Cha; Xaa2 is Asp, Pro; Xaa2 is
Ornithine, Diaminobutyric acid, Diaminoproprionic
acid, Norleucine, Aminobutric acid, or
Aminoproprionic acid; and Xaa3 is His or Asp]

(Cha B24, KP)
                                   SEQ ID NO: 6
Phe-Val-Asn-Gln-His-Leu-Cys-Gly-Ser-His-Leu-Val-

Glu-Ala-Leu-Tyr-Leu-Val-Cys-Gly-Glu-Arg-Gly-

Xaa1-Phe-Tyr-Thr-Lys-Pro-Thr [Xaa1 is Cha]

(Cha B24, AspB28)
                                   SEQ ID NO: 7
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa1-

Phe-Tyr-Thr-Asp-Lys-Thr [Xaa1 is Cha]

(SCI, B1, Cha B24, B26, B28, B29)
                                   SEQ ID NO: 8
Xaa1-Val-Asn-Gln-His-Leu-Cys-Gly-Ser-His-Leu-Val-

Glu-Ala-Leu-Tyr-Leu-Val-Cys-Gly-Glu-Arg-Gly-Xaa8-

Phe-Xaa2-Thr-Xaa3-Xaa4-Thr-Xaa5-Gly-Ile-Val-Xaa6-

Gln-Cys-Cys-Xaa7-Ser-Ile-Cys-Ser-Leu-Tyr-Gln-Leu-

Glu-Asn-Tyr-Cys-Asn;
```

[Xaa$_1$ is His or Phe; wherein Xaa$_2$ is Tyr or Phe, Xaa$_3$ is Pro, Lys, or Asp; wherein Xaa$_4$ is Lys or Pro; Xaa$_6$ is His or Glu; Xaa$_7$ is His or Thr; Xaa$_5$ is 0-35 of any amino acid or a break in the amino-acid chain; and Xaa$_8$ is Cha; and further wherein at least one substitution selected from the group of the following amino-acid substitutions is present:

Xaa$_1$ is His; and

Xaa$_7$ is His; and

Xaa$_6$ and Xaa$_7$ together are His.]

(Lys B3, Cha B24, Glu B29)

SEQ ID NO: 9

Phe-Val-Lys-Gln-His-Leu-Cys-Gly-Ser-His-Leu-Val-Glu-Ala-Leu-Tyr-Leu-Val-
Cys-Gly-Glu-Arg-Gly-Xaa₁-Phe-Tyr-Thr-Pro-Glu-Thr.

[Xaa₁ is Cyclohexanylalanine].

SEQ ID NO: 10

Phe Val Asn Gln His Leu Cys Gly Ser Xaa Leu Val Glu Ala Leu Tyr
Leu Val Cys Gly Glu Arg

Xaa is His or Asp

SEQ ID NO: 11

Gly Phe Phe Tyr Thr Pro Lys Thr

SEQ ID NO: 12

Gly Xaa₁ Phe Tyr Thr Xaa₂ Xaa₃ Thr

Xaa₁ is Phe or Cyclohexanylalanine
Xaa₂ is Pro or Lys
Xaa₃ is Pro or Lys

SEQ ID NO: 13

Gly Xaa₁ Phe Tyr Thr Pro Xaa₂ Thr

Xaa₁ is Phe or Cyclohexanylalanine; Xaa₂ is Ornithine

SEQ ID NO: 14

Gly Xaa₁ Phe Tyr Thr Pro Xaa₂ Thr

Xaa₁ is Phe or Cyclohexanylalanine; Xaa₂ is Norleucine

SEQ ID NO: 15 tttgtgaacc aacacctgtg cggctcacac ctggtggaag ctctctacct agtgtgcggg
gaacgaggct agttctacac acccaagacc

SEQ ID NO: 16 tttgttaacc aacatttgtg tggttctcat ttggttgaag ctttgtactt ggtttgtggt
gaaagaggtt agttttacac tccaaagact

SEQ ID NO: 17 tttgtgaacc aacacctgtg cggctcacac ctggtggaag ctctctacct agtgtgcggg
gaacgaggct agttctacac acccaagacc cgccgggagg cagaggacct gcaggtgggg
caggtggagc tgggcggcgg ccctggtgca ggcagcctgc agcccttggc cctgaggggg
tccctgcaga gcgtggcat tgtggaacaa tgctgtacca gcatctgctc cctctaccag
ctggagaact actgcaacta g

SEQ ID NO: 18 tttgttaacc aacatttgtg tggttctcat ttggttgaag ctttgtactt ggtttgtggt
gaaagaggtt agttttacac tccaaagact agaagagaag ctgaagattt gcaagttggt
caagttgaat tgggtggtgg tccaggtgct ggttctttgc aaccattggc tttgaaggt
tctttgcaaa agagaggtat tgttgaacaa tgttgtactt ctatttgttc tttgtaccaa
ttggaaaact actgtaacta a

SEQ ID NO: 19

Gly Ile Val Glu Gln Cys Cys Glu Ser Ile Cys Ser Leu Tyr Gln Leu
Glu Asn Tyr Cys Asn

SEQ ID NO: 20

Phe Val Asn Gln His Leu Cys Gly Ser His Leu Val Glu Ala Leu Tyr
Leu Val Cys Gly Glu Arg Gly Phe Phe Tyr Thr Lys Pro Thr

```
                                                                SEQ ID NO: 21
Phe Val Asn Gln His Leu Cys Gly Ser Asp Leu Val Glu Ala Leu Tyr

Leu Val Cys Gly Glu Arg Gly Xaa Phe Tyr Thr Lys Pro Thr

Xaa is Cyclohexanylalanine

SEQ ID NO: 22
Phe Val Asn Gln His Leu Cys Gly Ser Asp Leu Val Glu Ala Leu Tyr

Leu Val Cys Gly Glu Arg Gly Phe Xaa Tyr Thr Lys Pro Thr

Xaa is Cyclohexanylalanine

SEQ ID NO: 23
Asp Tyr Lys Asp Asp Asp Asp Lys (variant human A chain, A12)
                                                                SEQ ID NO: 24
Gly-Ile-Val-Glu-Gln-Cys-Cys-Thr-Ser-Ile-Cys-Xaa-Leu-Tyr-Gln-Leu-Glu-Asn-Tyr-Cys-Asn Where Xaa indicates Ala, Thr, Asp, Asn, Glu, Gln, His or Tyr.

(variant human A chain, A13)
                                                                SEQ ID NO: 25
Gly-Ile-Val-Glu-Gln-Cys-Cys-Thr-Ser-Ile-Cys-Ser-Xaa-Tyr-Gln-Leu-Glu-Asn-Tyr-Cys-Asn Where Xaa indicates Ala, Glu, Gln, His, Tyr or Trp.

(variant human A chain, A17)
                                                                SEQ ID NO: 26
Gly-Ile-Val-Glu-Gln-Cys-Cys-Thr-Ser-Ile-Cys-Ser-Leu-Tyr-Gln-Leu-Xaa-Asn-Tyr-Cys-Asn Where Xaa indicates Ala, Gln, His, Trp, or Tyr.

(variant human A chain, A12, A13, and/or A17)
                                                                SEQ ID NO: 27
Gly-Ile-Val-Glu-Gln-Cys-Cys-Thr-Ser-Ile-Cys-Xaa$_1$-Xaa$_2$-Tyr-Gln-Leu-Xaa$_3$-Asn-Tyr-Cys-Asn
```

Where at least one of the Xaa sites contains a substitution relative to wild-type human insulin and wherein Xaa$_1$ indicates Ser, Ala, Thr, Asp, Asn, Glu, Gln, His or Tyr; where Xaa$_2$ indicates Leu, Ala, Glu, Gln, His, or Trp; and where Xaa$_3$ indicates Glu, Ala, Gln, His, Trp, or Tyr.

```
(variant human A chain, A8, A12, A13, and/or A17)
                                                                SEQ ID NO: 28
Gly-Ile-Val-Glu-Gln-Cys-Cys-Xaa$_1$-Ser-Ile-Cys-Xaa$_2$-Xaa$_3$-Tyr-Gln-Leu-Xaa$_4$-Asn-Tyr-Cys-Asn
```

Where at least one of the Site-2-related sites (A12, A13, and A17) contains a substitution relative to wild-type human insulin and wherein Xaa$_2$ indicates Ser, Ala, Thr, Asp, Asn, Glu, Gln, His or Tyr; where Xaa$_3$ indicates Leu, Ala, Glu, Gln, His, or Trp; and where Xaa$_4$ indicates Glu, Ala, Gln, His, Trp, or Tyr; and where Xaa$_1$ indicates His, Glu, Gln, Arg, or Lys.

```
(variant human B chain, B13)
                                                                SEQ ID NO: 29
Phe-Val-Asn-Gln-His-Leu-Cys-Gly-Ser-His-Leu-
Val-Xaa$_3$-Ala-Leu-Tyr-Leu-Val-Cys-Gly-Glu-
Arg-Gly-Phe-Phe-Tyr-Thr-Xaa$_1$-Xaa$_2$-Thr
```

Where Xaa$_3$ indicates Ala, Asp, His, or Leu; where Xaa$_1$ indicates any amino acid excluding Glycine, Tryptophan, Phenylalanine, Tyrosine, and Cysteine; and where Xaa$_2$ indicates Pro, Glu or Lys.

```
(variant human B chain, B17)
                                                                SEQ ID NO: 30
Phe-Val-Asn-Gln-His-Leu-Cys-Gly-Ser-His-Leu-Val-
Glu-Ala-Leu-Tyr-Xaa$_3$-Val-Cys-Gly-Glu-Arg-Gly-
Phe-Phe-Tyr-Thr-Xaa$_1$-Xaa$_2$-Thr
```

Where Xaa$_3$ indicates Glu, Gln, Ala, His, Trp, or Tyr; where Xaa$_1$ indicates any amino acid excluding Glycine, Tryptophan, Phenylalanine, Tyrosine, and Cysteine; and where Xaa$_2$ indicates Pro, Glu, or Lys.

```
(variant human B chain, B13 and B17)
                                                                SEQ ID NO: 31
Phe-Val-Asn-Gln-His-Leu-Cys-Gly-Ser-His-Leu-Val-
Xaa$_1$-Ala-Leu-Tyr-Xaa$_2$-Val-Cys-Gly-Glu-Arg-Gly-Phe-
Phe-Tyr-Thr-Xaa$_3$-Xaa$_4$-Thr
```

Where Xaa$_1$ indicates Ala, Asp, His, or Leu; where Xaa$_2$ indicates Gln, Glu, Ala, His, Trp, or Tyr; where Xaa$_3$ indicates any amino acid excluding Glycine, Tryptophan, Phenylalanine, Tyrosine, and Cysteine; and where Xaa$_4$ indicates Pro, Glu, or Lys.

```
                                                                SEQ ID NO: 32
Phe-Val-Asn-Gln-His-Leu-Cys-Gly-Ser-Xaa$_{10}$-Leu-Val-
Xaa$_1$-Ala-Leu-Tyr-Xaa$_2$-Val-Cys-Gly-Glu-Arg-Gly-Phe-
```

```
                              -continued
Phe-Tyr-Thr-Xaa₆-Xaa₇-Thr-Gly-Z-Arg-Arg-Gly-Ile- Val-Glu-Gln-Cys-Cys-Xaa₈-Ser-Ile-Cys-Xaa₃-Xaa₄-

Xaa₉-Gln-Leu-Xaa₅-Asn-Tyr-Cys-Asn
```

Where at least one of the Site-2-related sites (B13, B17, A12, A13, and A17) contains a substitution relative to wild-type human insulin wherein Xaa₁ indicates Glu, Ala, Asp, His, or Leu; where Xaa₂ indicates Leu, Glu, Gln, Ala, His, Trp, or Tyr; where Xaa₃ indicates Ser, Ala, Thr, Asp, Asn,

What is claimed is:

1. An insulin analogue comprising (i) the insulin A-chain polypeptide and (ii) the insulin B-chain polypeptide, wherein the insulin A-chain polypeptide contains a Glu substitution at a position corresponding to position A8 relative to wild type insulin, and an Ala, Glu, Gln, His, Tyr, Phe or Trp substitution at a position corresponding to A13 relative to wild type insulin, and wherein the insulin B-chain polypeptide contains a Cyclohexanylalanine substitution at a position corresponding to position B24 relative to wild type insulin, and further wherein the insulin analogue is formulated as a pharmaceutical composition containing zinc ions at a molar ratio of 2.2 to 3.0 zinc ions per hexamer of insulin analogue.

2. The insulin analogue of claim 1, wherein the substitution at the position corresponding to position A13 is Trp.

3. The insulin analogue of claim 2, wherein the insulin A-chain sequence comprises SEQ ID NO: 50.

4. The insulin analogue of claim 2, wherein the B-chain sequence comprises SEQ ID NO: 51.

5. The insulin analogue of claim 2, wherein the insulin B-chain polypeptide additionally comprises a Lys substitution at a position corresponding to position B28 relative to wild type insulin and a Pro substitution at a position corresponding to position B29 relative to wild type insulin.

6. The insulin analogue of claim 3, wherein the B-chain sequence comprises SEQ ID NO: 51.

7. A method of lowering the blood sugar concentration of a patient, the method comprising administering a physiologically effective amount of an insulin analogue or a physiologically acceptable salt thereof to the patient, wherein the insulin analogue comprises (i) the insulin A-chain polypeptide and (ii) the insulin B-chain polypeptide, and wherein the insulin A-chain polypeptide contains a Glu substitution at a position corresponding to position A8 relative to wild type insulin, and an Ala, Glu, Gln, His, Tyr, Phe or Trp substitution at a position corresponding to A13 relative to wild type insulin, and wherein the insulin B-chain polypeptide contains a Cyclohexanylalanine substitution at a position corresponding to position B24 relative to wild type insulin, and further wherein the insulin analogue is formulated as a pharmaceutical composition containing zinc ions at a molar ratio of 2.2 to 3.0 zinc ions per hexamer of insulin analogue.

8. The method of claim 7, wherein the substitution at the position corresponding to position A13 is Trp.

9. The method of claim 8, wherein the insulin A-chain sequence comprises SEQ ID NO: 50.

10. The method of claim 8, wherein the insulin B-chain sequence comprises SEQ ID NO: 51.

11. The method of claim 8, wherein the insulin B-chain sequence additionally comprises a Lys substitution at a position corresponding to position B28 relative to wild type insulin and a Pro substitution at a position corresponding to position B29 relative to wild type insulin.

12. The method of claim 9, wherein the insulin B-chain sequence comprises SEQ ID NO: 51.

* * * * *